(12) United States Patent
Keller et al.

(10) Patent No.: US 11,460,382 B2
(45) Date of Patent: Oct. 4, 2022

(54) TISSUE COLLECTION AND PROCESSING CASSETTE

(71) Applicant: Devicor Medical Products, Inc., Cincinnati, OH (US)

(72) Inventors: Bryan R. Keller, Loveland, OH (US); Adam Walter, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 765 days.

(21) Appl. No.: 16/223,370

(22) Filed: Dec. 18, 2018

(65) Prior Publication Data

US 2019/0195754 A1 Jun. 27, 2019

Related U.S. Application Data

(60) Provisional application No. 62/607,544, filed on Dec. 19, 2017.

(51) Int. Cl.
*G01N 1/31* (2006.01)
*A61B 10/02* (2006.01)
(Continued)

(52) U.S. Cl.
CPC ......... *G01N 1/312* (2013.01); *A61B 10/0096* (2013.01); *A61B 10/0266* (2013.01);
(Continued)

(58) Field of Classification Search
CPC ............ A61B 10/0096; A61B 10/0283; A61B 10/0266; A61B 10/0275; A61B 2010/0225; G01N 1/286; G01N 2001/2873
See application file for complete search history.

(56) References Cited

U.S. PATENT DOCUMENTS 5,817,032 A 10/1998 Williamson, IV et al.
7,715,523 B2 5/2010 Lafferty
(Continued)

FOREIGN PATENT DOCUMENTS

EP 0 751 744 A1 1/1997
WO WO 95/25465 A2 9/1995
(Continued)

OTHER PUBLICATIONS

U.S. Appl. No. 62/607,544, filed Dec. 19, 2017.
International Search Report and Written Opinion dated May 9, 2019 for Application No. PCT/US2018/066237, 17 pgs.

*Primary Examiner* — Sean P Dougherty
(74) *Attorney, Agent, or Firm* — Frost Brown Todd LLC

(57) ABSTRACT

A sample collection and processing apparatus includes a tissue processing cassette and a biopsy device. The tissue processing cassette is sized to be used in a pathology laboratory for purposes of dehydrating, embedding and sectioning. The tissue processing cassette has at least one distal opening through which tissue samples are received and has a floor with a plurality of openings. The biopsy device has a cassette holder adapted to receive the tissue processing cassette. The cassette holder has a fluid path adapted to be coupled to a vacuum source and in fluid communication with the interior of the tissue processing cassette through the openings of the floor such that vacuum from the vacuum source facilitates the transfer of the cut tissue samples into the received tissue processing cassette.

16 Claims, 63 Drawing Sheets

(51) Int. Cl.
*G01N 1/28* (2006.01)
*A61B 10/00* (2006.01)

(52) U.S. Cl.
CPC ......... *A61B 10/0283* (2013.01); *G01N 1/286* (2013.01); *A61B 10/0275* (2013.01); *A61B 2010/0225* (2013.01); *G01N 2001/2873* (2013.01)

(56) References Cited

U.S. PATENT DOCUMENTS

| | | | | |
|---|---|---|---|---|
| 7,846,107 B2* | 12/2010 | Hoffman | ................ | A61B 10/06 600/561 |
| 7,858,038 B2* | 12/2010 | Andreyko | .............. | A61B 90/30 700/266 |
| 7,985,239 B2 | 7/2011 | Suzuki | | |
| 8,118,755 B2* | 2/2012 | Hibner | ............... | A61B 10/0266 600/564 |
| 8,485,987 B2 | 7/2013 | Videbaek et al. | | |
| 8,503,602 B2 | 8/2013 | Lafferty | | |
| 8,802,034 B2 | 8/2014 | Bartfeld et al. | | |
| 9,056,317 B2 | 6/2015 | Bartfeld et al. | | |
| 9,389,153 B2* | 7/2016 | Newby | ................... | B01L 3/508 |
| 9,409,164 B2* | 8/2016 | Tawfik | ................... | B01L 3/502 |
| 9,877,706 B2 | 1/2018 | Speeg et al. | | |
| 9,955,955 B2 | 5/2018 | Fiebig et al. | | |
| 9,999,406 B2* | 6/2018 | Hibner | ............... | A61B 10/0275 |
| 10,314,563 B2* | 6/2019 | Leimbach | .......... | A61B 10/0266 |
| 10,729,856 B1* | 8/2020 | Nock | ................. | A61B 10/0096 |
| 2014/0039343 A1 | 2/2014 | Mescher et al. | | |
| 2014/0121560 A1* | 5/2014 | Parks | ................. | A61B 10/0283 600/562 |
| 2014/0275999 A1* | 9/2014 | Speeg | ................ | A61B 10/0096 600/424 |
| 2015/0065913 A1* | 3/2015 | Keller | ................ | A61B 10/0283 600/566 |
| 2017/0311935 A1* | 11/2017 | Choung | ............ | A61B 10/0096 |
| 2018/0000463 A1* | 1/2018 | Keller | ................ | B01L 3/50853 |
| 2018/0004918 A1 | 1/2018 | Walter et al. | | |
| 2018/0098755 A1* | 4/2018 | Keller | ................ | A61B 10/0096 |

FOREIGN PATENT DOCUMENTS

| | | |
|---|---|---|
| WO | WO 2013/192606 A1 | 12/2013 |
| WO | WO 2013/192607 A1 | 12/2013 |
| WO | WO 2014/151603 A1 | 9/2014 |

* cited by examiner

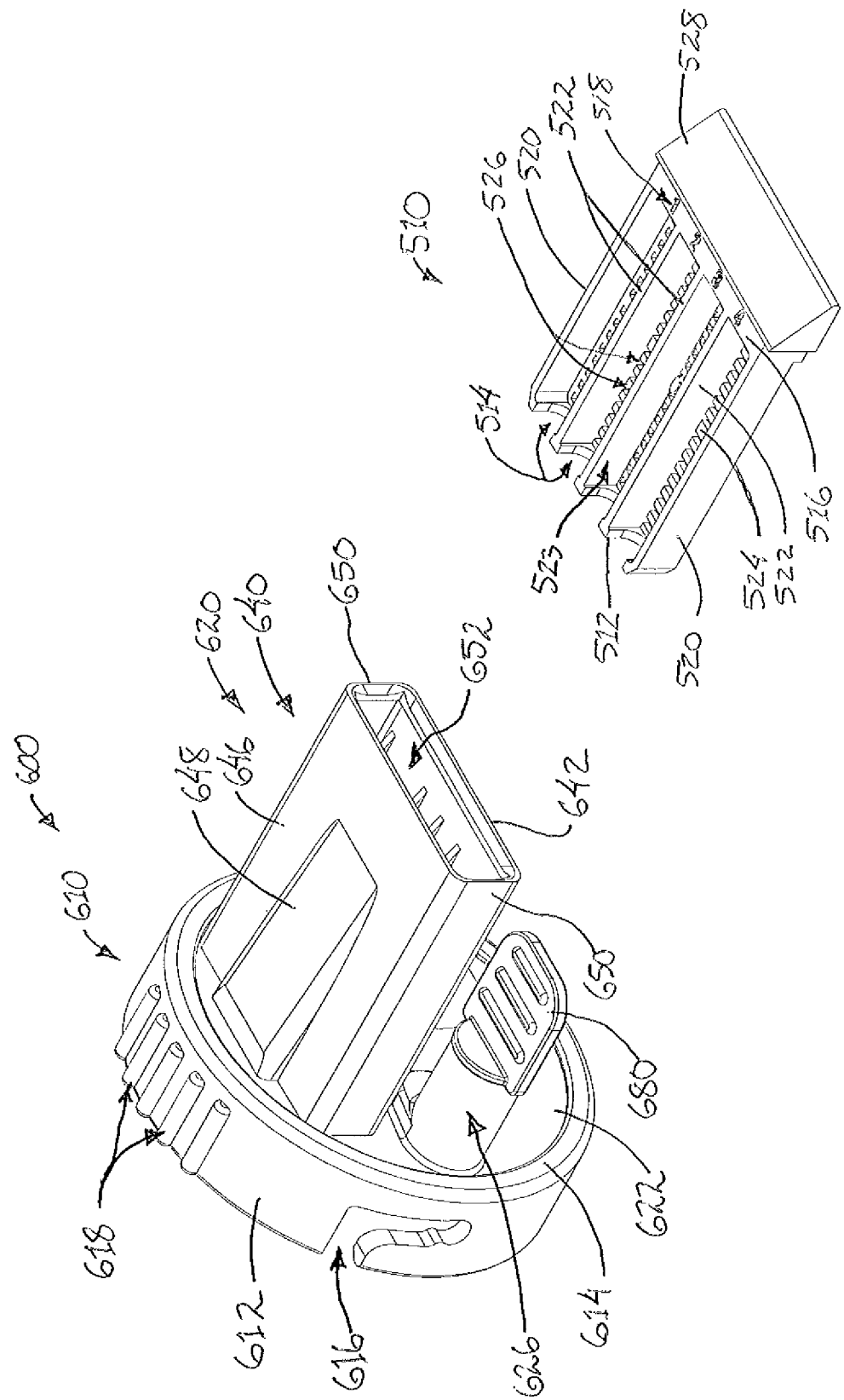

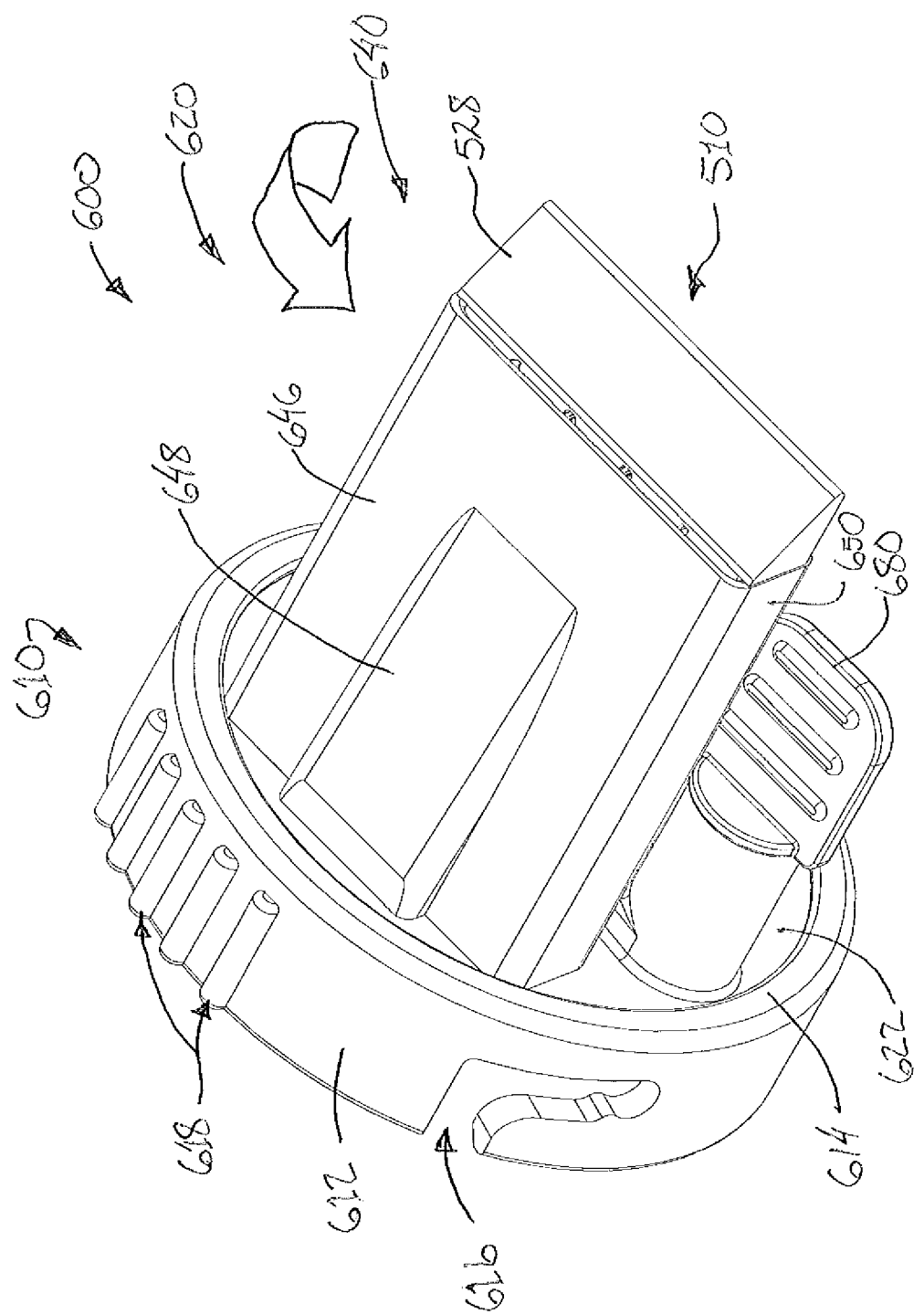

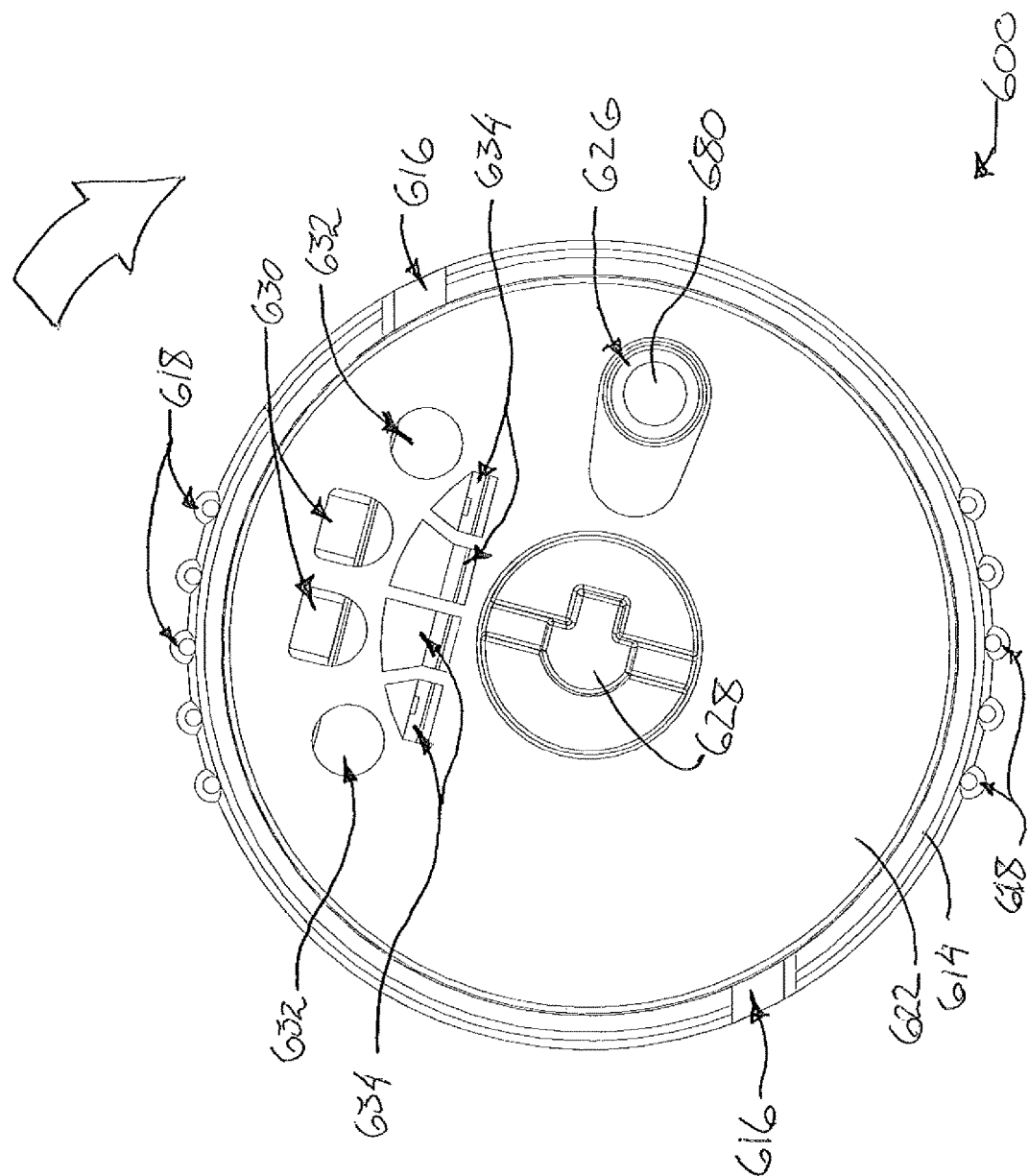

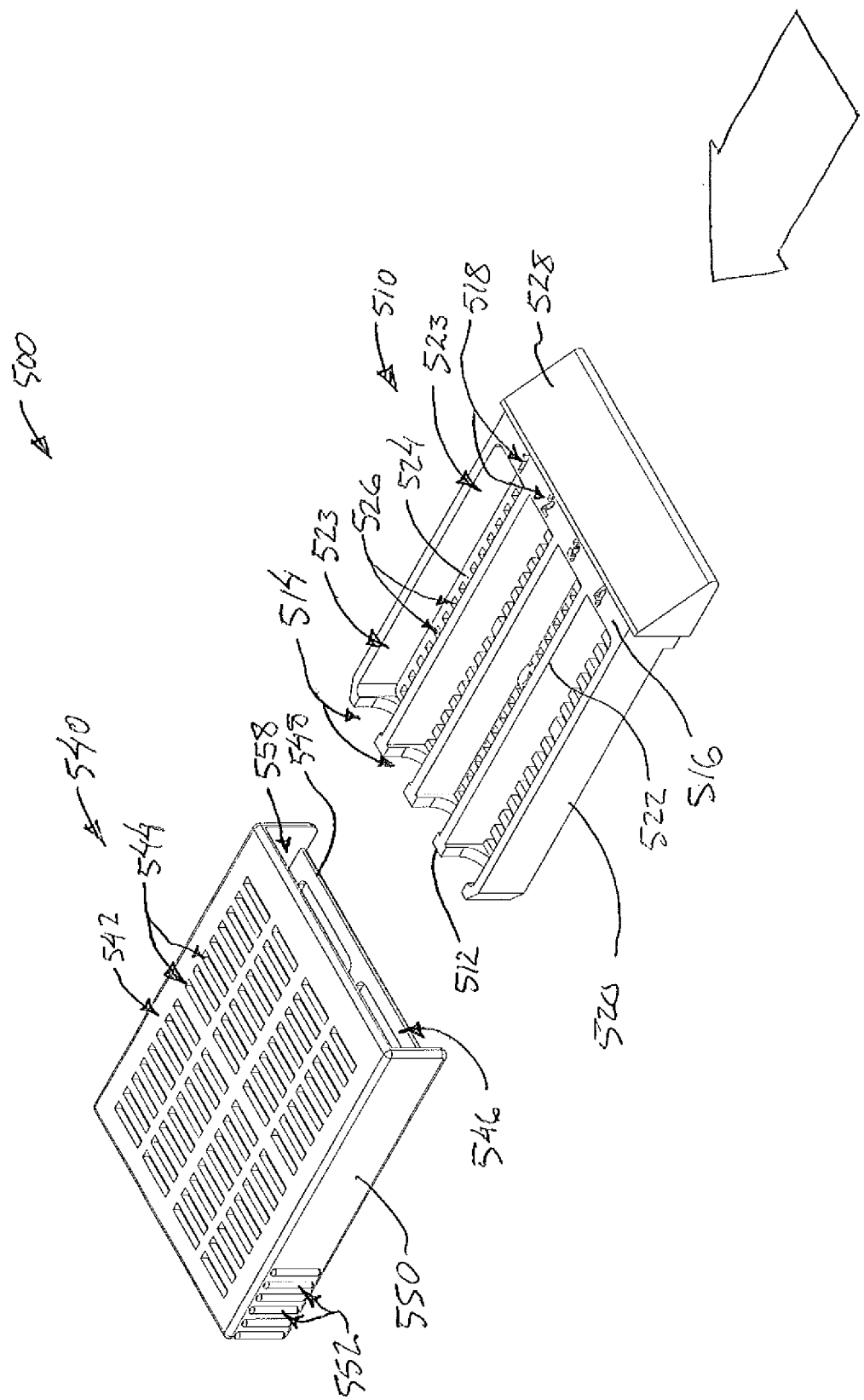

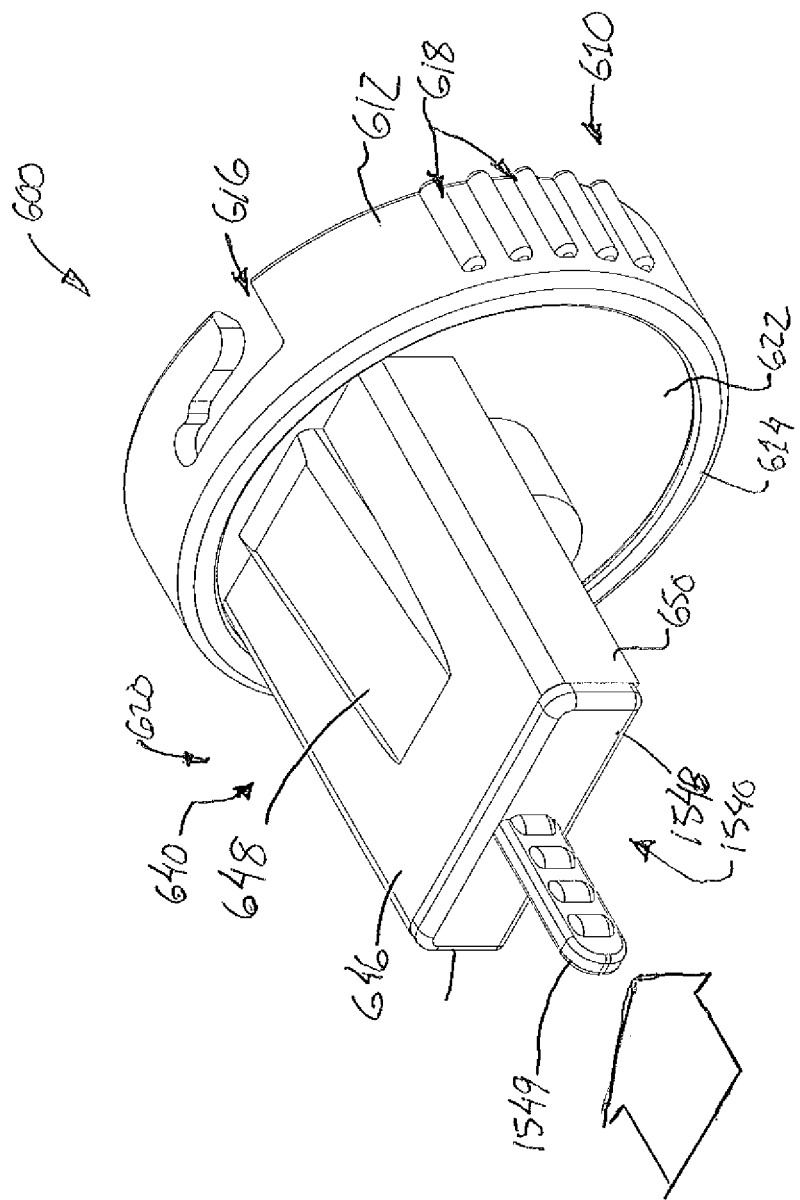

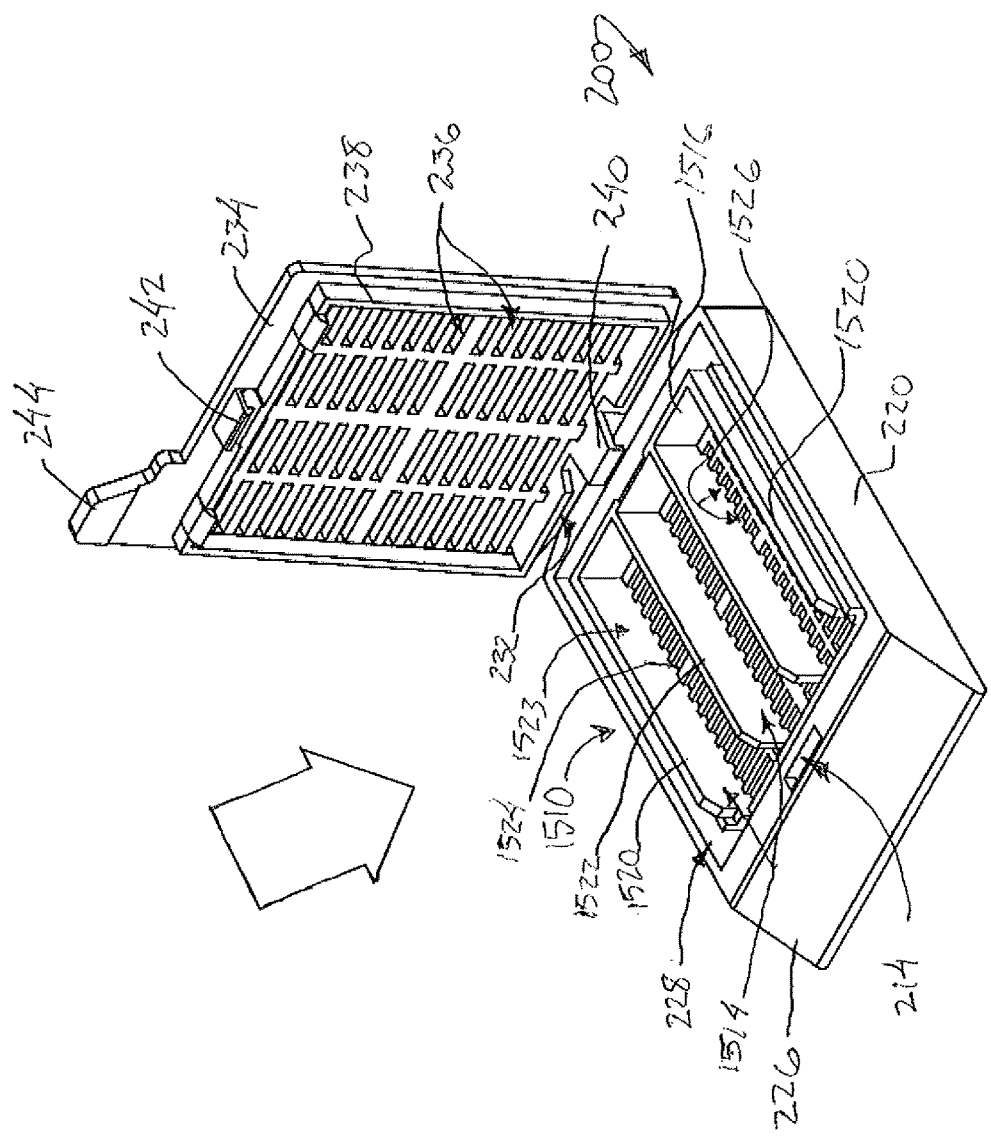

TISSUE COLLECTION AND PROCESSING CASSETTE

PRIORITY

This application claims priority to U.S. Provisional Patent App. No. 62/607,544 entitled "Tissue Collection and Processing Cassette," filed Dec. 19, 2017, the disclosure of which is incorporated by reference herein.

BACKGROUND

A biopsy is the removal of a tissue sample to examine tissue for signs of cancer or other disorders. Tissue samples are obtained in a variety of ways using various medical procedures involving a variety of the sample collection devices. For example, biopsies may be open (surgically removing tissue) or percutaneous (e.g. by fine needle aspiration, core needle biopsy or vacuum assisted biopsy). After the tissue sample is collected, the tissue sample is analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, Positron Emission Mammography ("PEM" guidance), Breast-Specific Gamma Imaging ("BSGI") guidance or otherwise.

At several steps during tissue processing using conventional techniques and instruments, it may be necessary to manually manipulate the tissue. This manual manipulation takes time and introduces the possibility of human error causing mistakes during the processing of tissue. Any human error during the processing of tissue can make the pathological examination of the tissue much more problematic to achieve the desired goal of having an accurate diagnosis. Thus, it is understood that a desired goal of modern tissue processing is the reduction of the requirement that tissue be manually manipulated.

Various devices and techniques for tissue handling are disclosed in International Pat. Pub. No. WO 2013/192606, entitled "Biopsy Tissue Sample Transport Device and Method of Using Thereof," published on Dec. 27, 2013; International Pat. Pub. No. WO 2013/192607, entitled "Tissue Sample Container and Methods," published on Dec. 27, 2013; International Pat. Pub. No. WO 2014/151603, entitled "Biopsy Device," published on Sep. 25, 2014; U.S. Pat. No. 7,715,523, entitled "System and Apparatus for Rapid Stereotactic Breast Biopsy Analysis," issued on May 11, 2010; U.S. Pat. No. 8,503,602, entitled "System and Apparatus for Rapid Stereotactic Breast Biopsy Analysis," issued on Aug. 6, 2013; U.S. Pat. No. 8,485,987, entitled "Tissue Handling System with Reduced Operator Exposure," issued Jul. 16, 2016; U.S. Pat. No. 8,802,034, "Tissue Container for Molecular and Histology Diagnostics Incorporating a Breakable Membrane," issued on Aug. 12, 2014; and U.S. Pat. No. 9,056,317, "Tissue Container for Molecular and Histology Diagnostics Incorporating a Breakable Membrane," issued on Jun. 16, 2016. The disclosure of each of the above-cited U.S. Patents is incorporated by reference herein.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 15B depicts another side cross-sectional view of the cassette assembly of

FIG. 8, with the cassette tray of FIG. 11 intermediately inserted into the cover of FIG. 13;

FIG. 19 depicts a perspective cross-sectional view of the rotatable member of

FIG. 18, the cross-section taken along line 19-19 of FIG. 18;

FIG. 20A depicts a perspective view of the tissue sample holder assembly of FIG. 16, with the cassette tray of FIG. 11 positioned for insertion into the tissue sample holder assembly;

FIG. 22D depicts yet another perspective view of the tissue sample holder assembly of FIG. 16, with the rotatable member of FIG. 18 in a fourth sample receiving position;

FIG. 23C depicts still another front elevational view of the tissue sample holder assembly of FIG. 16, with the rotatable member of FIG. 18 in the third sample receiving position;

FIG. 24 depicts a perspective view of the cassette assembly of FIG. 8, with the cassette tray of FIG. 11 being inserted into the cover of FIG. 13;

FIG. 30 depicts a detailed top plan view of a portion of the cassette tray of FIG. 29;

FIG. 53B depicts another perspective view of the tissue sample holder assembly of FIG. 16, with the cassette adaptor of FIG. 51 prepared for insertion into the tissue sample holder assembly;

FIG. 53C depicts another perspective view of the tissue sample holder assembly of FIG. 16, with the cassette adaptor of FIG. 51 inserted into the tissue sample holder assembly;

FIG. 54B depicts another perspective view of the cassette of FIG. 6, with the adaptor tray of FIG. 54A received within the cassette.

Figure 1:
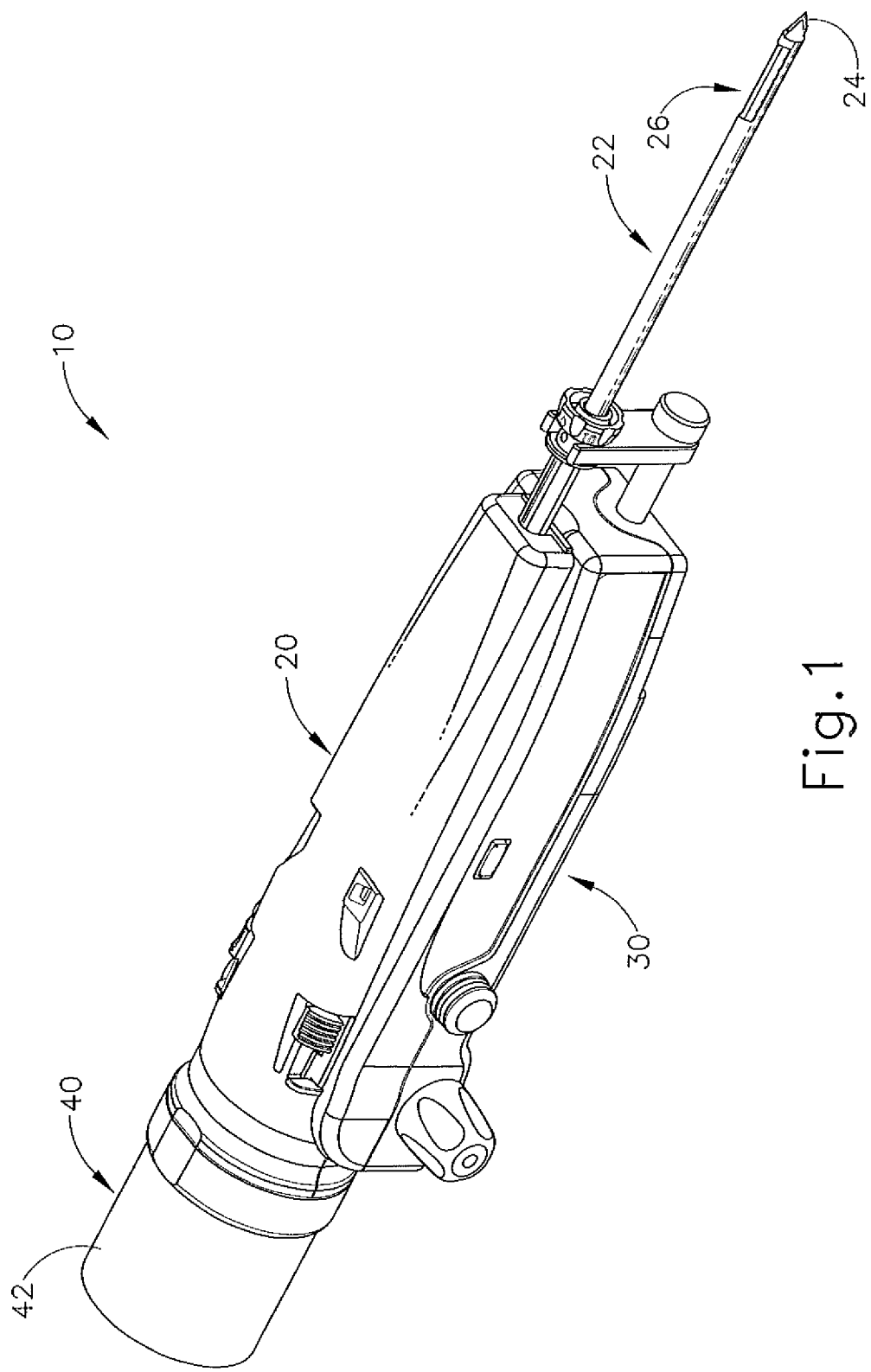
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Biopsy Device

FIG. 1 depicts an exemplary biopsy device (10) that can be used to acquire tissue samples from a patient. Biopsy device (10) comprises a probe assembly (20), a holster assembly (30), and a tissue sample holder assembly (40). Probe assembly (20) includes a distally projecting needle (22) that has a tissue piercing tip (24) and a lateral aperture (26) that is located proximal to tip (24). A tubular cutter (not shown) is slidably disposed in needle (22) and is operable to sever tissue that is protruding through lateral aperture (26). The severed tissue samples are communicated proximally through the lumen of the cutter to tissue sample holder assembly (40), as described below. In some versions, probe assembly (20) is coupled with a control module that is operable to provide communication of vacuum, saline, and/or atmospheric air to probe assembly (20).

Holster assembly (30) includes features that are operable to drive the cutter, features that are operable to fire needle (22) distally into tissue, and features that are operable to rotate needle (22) about a longitudinal axis of needle (22). In some versions, holster assembly (30) is coupled with a control module via a cable that is operable to provide electrical power and/or other electrical signals to holster assembly (30). In addition, or in the alternative, holster assembly (30) may receive a pressurized medium (e.g., air, hydraulic fluid, etc.) in order to provide motive force to drive the cutter of probe assembly (20).

In the present example, probe assembly (20) and holster assembly (30) are configured for use in a stereotactic image guided biopsy procedure. By way of example only, probe assembly (20) and holster assembly (30) may be constructed and operable in accordance with at least some of the teachings of U.S. Pub. No. 2014/0039343, entitled "Biopsy System," published Feb. 6, 2014, the disclosure of which is incorporated by reference herein. Alternatively, probe assembly (20) and holster assembly (30) may be configured for use in (or otherwise be used in) an ultrasound image guided biopsy procedure and/or an MRI guided biopsy procedure. By way of further example only, probe assembly (20) and holster assembly (30) may be constructed and operable in accordance with at least some of the teachings of U.S. Pub. No. 2013/0150751, entitled "Biopsy Device with Slide-In Probe," published Jun. 13, 2013, the disclosure of which is incorporated by reference herein. Alternatively, probe assembly (20) and holster assembly (30) may be constructed and operable in any other suitable fashion.

Figure 2:
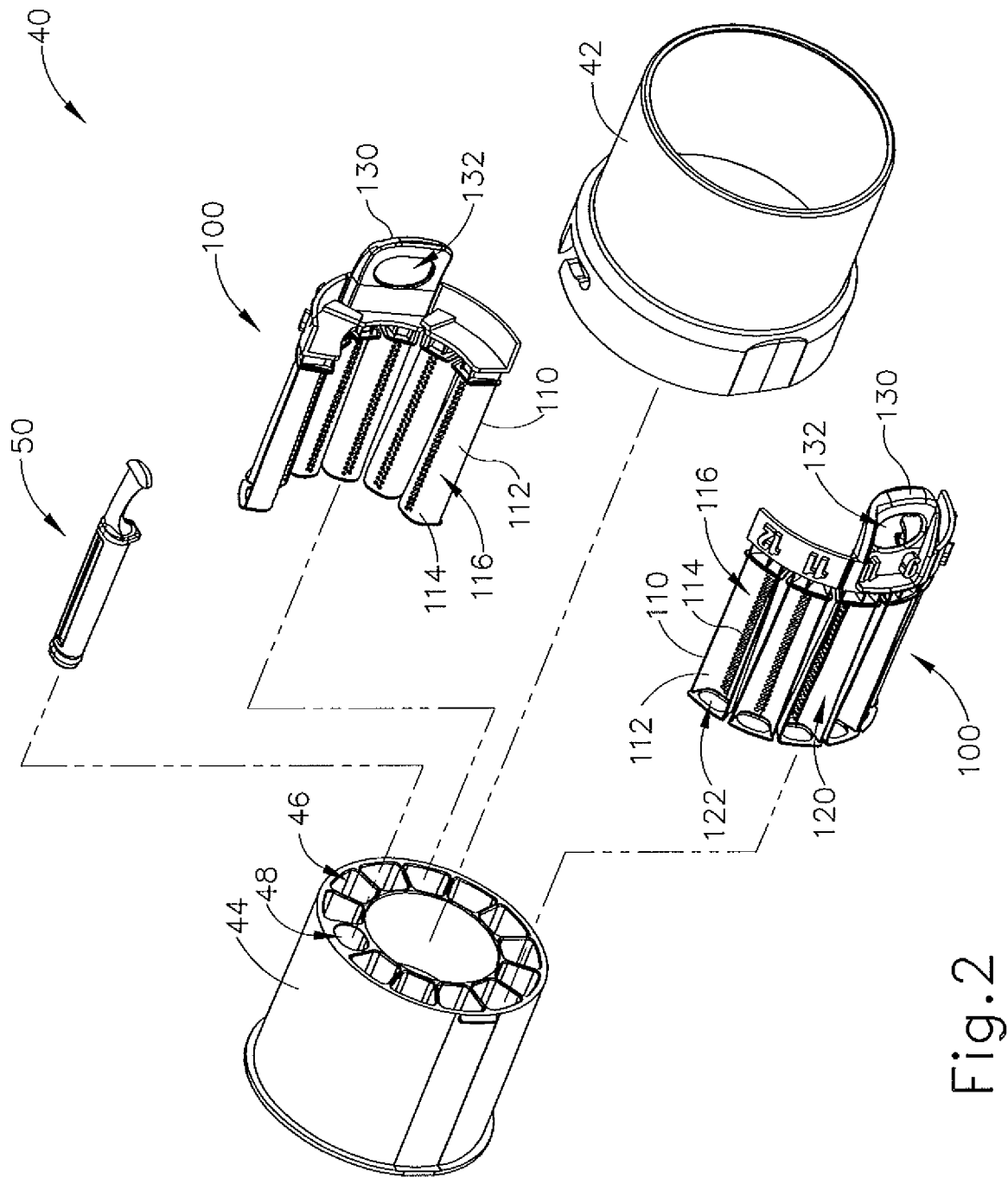
FIG. 2 depicts an exploded perspective view of a tissue sample holder assembly of the biopsy device of FIG. 1.

As noted above, tissue sample holder assembly (40) is configured to receive tissue samples that are severed by the cutter from tissue protruding through lateral aperture (26). As shown in FIG. 2, tissue sample holder assembly (40) of this example comprises a cylindraceous outer cover (42) that is removably coupled with probe assembly (20). A rotatable (44) member is rotatably positioned within cover (42). Rotatable member (44) defines an angularly spaced array of strip receiving chambers (46) and a plug chamber (48), such that chambers (46, 48) together an annular arrangement. Rotatable member (44) is rotatable relative to probe assembly (20) to selectively index chambers (46, 48) relative to the cutter. In some versions, drive components in holster assembly (30) drive rotation of rotatable member (44). In some other versions, rotatable member (44) is driven manually by the operator manually grasping some portion of tissue sample holder assembly (40).

As also shown in FIG. 2, tissue sample holder assembly (40) further includes a pair of tissue sample trays (100). Each tissue sample tray (100) comprises a set of distally projecting tissue sample strips (110). Each tissue sample strip (110) is configured for removable insertion into a corresponding strip receiving chamber (46) of rotatable member (44). Each tissue sample strip (110) comprises a set of strip sidewalls (112) joined by a floor (114). Strip sidewalls (112) and floor (114) cooperate to define a tissue receiving chamber (120), such that each tissue sample strip (110) is configured to receive a corresponding tissue sample. Floor (114) defines a plurality of openings (116) that are sized to provide communication of suction and fluids therethrough, while preventing communication of tissue samples therethrough. It should be understood that suction may be communicated through strip receiving chambers (46) to reach tissue receiving chambers (120) via openings (116). Each tissue sample strip (110) of the present example also includes a distal opening (122). Distal opening (122) is sized and configured to enable a severed tissue sample to pass therethrough in order for the tissue sample to be deposited into tissue receiving chamber (120).

Figure 3:
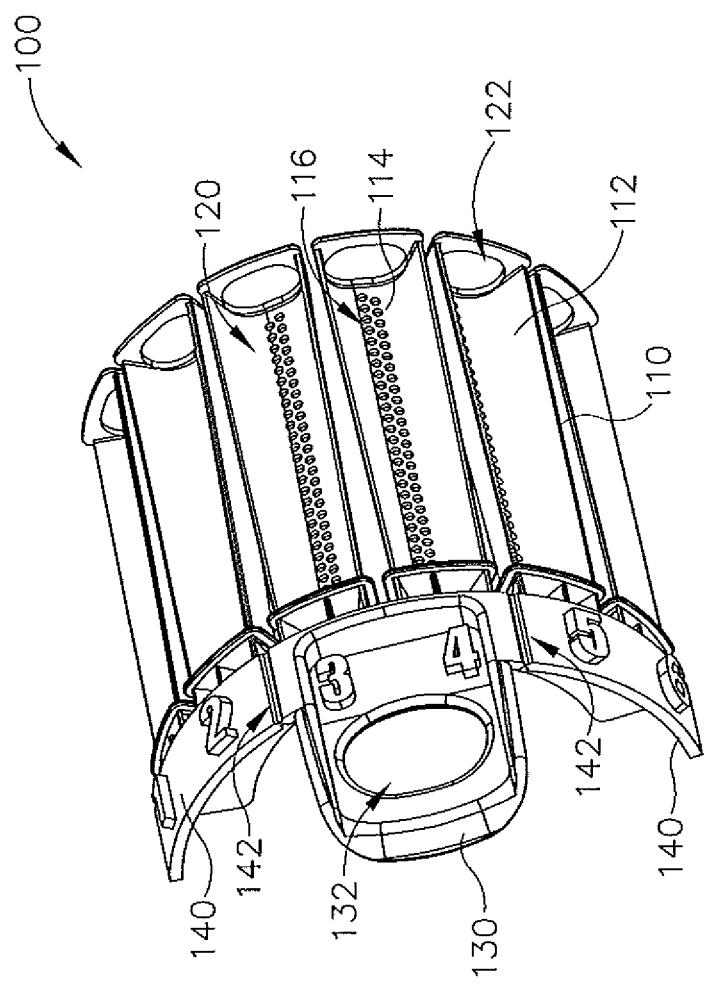
FIG. 3 depicts a perspective view of a tissue sample tray of the tissue sample holder assembly of FIG. 2, with the tissue sample tray in an arcuate configuration.
Figure 4:
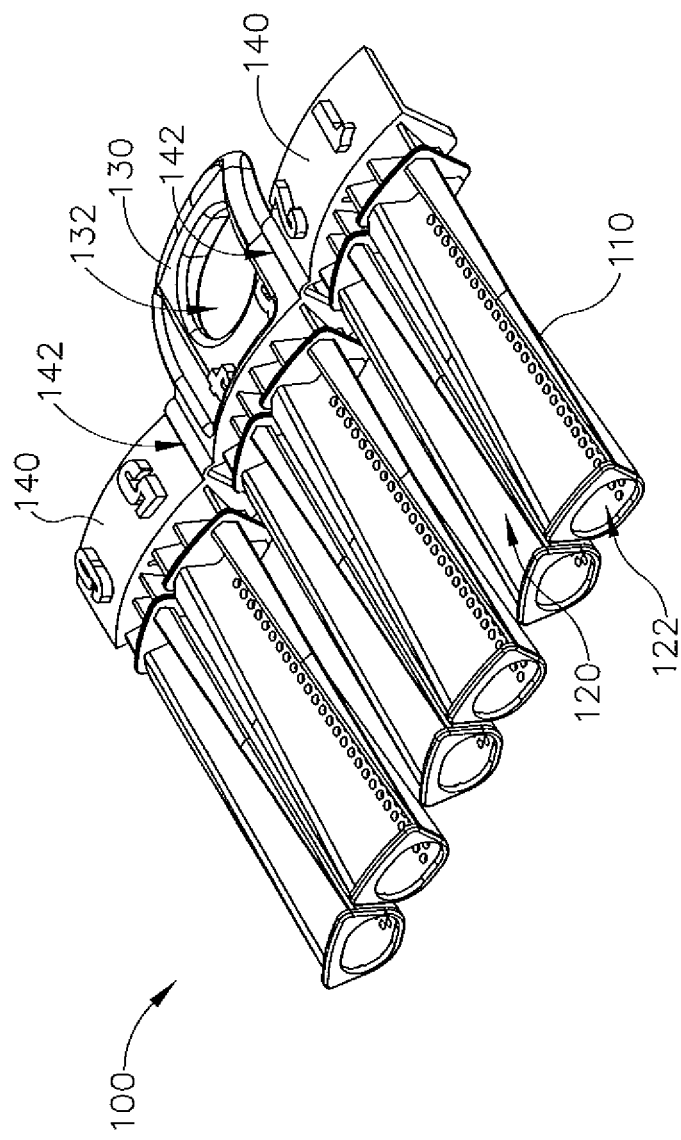
FIG. 4 depicts a perspective view of the tissue sample tray of FIG. 3 in a flattened configuration.

As best seen in FIGS. 3-4, each tissue sample tray (100) further includes a proximally projecting pull tab (130) that defines a tab opening (132). Pull tab (130) is configured to facilitate grasping of tissue sample tray (100) by an operator. Tissue sample tray (100) also includes a set of proximal panels (140). In the present example, two tissue sample strips (110) project distally relative to a corresponding panel (140) of the set of panels (140). Pull tab (130) projects proximally from the centrally positioned panel (140). Panels (140) are flexibly joined together by living hinges (142). Living hinges (142) enable tissue sample tray (100) to transition between the arcuate configuration shown in FIG. 3 and the flattened configuration shown in FIG. 4. In the arcuate configuration, tissue sample tray (100) is configured to fit in rotatable member (44). In the flattened configuration, tissue sample tray (100) is configured to fit in a container (200) as will be described in greater detail below.

As noted above, rotatable member (44) is rotatable relative to probe assembly (20) to selectively index strip receiving chambers (46) relative to the cutter, to thereby selectively index tissue receiving chambers (120) of tissue sample strips (110) relative to the cutter. Rotatable member (44) is also operable to index plug receiving chamber (48) relative to the cutter. When rotatable member (44) is angularly positioned to index plug receiving chamber (48) relative to the cutter, plug (50) may be removed from plug receiving chamber (48) to enable insertion of a biopsy site marker applier instrument (or some other kind of instrument) through the cutter and needle assembly (22), thereby providing an access path to the biopsy site via lateral aperture (26). Otherwise, plug (50) may be left in plug receiving chamber (48) during operation of biopsy device (10), thereby sealing plug receiving chamber (48).

By way of example only, tissue sample holder (40) may be configured and operable in accordance with at least some of the teachings of U.S. Pub. No. 2014/0039343, entitled "Biopsy System," published Feb. 6, 2014, the disclosure of which is incorporated by reference herein and/or U.S. Pub. No. 2014/0275999, entitled "Biopsy Device," published Sep. 18, 2014, the disclosure of which is incorporated by reference herein.

Figure 5:
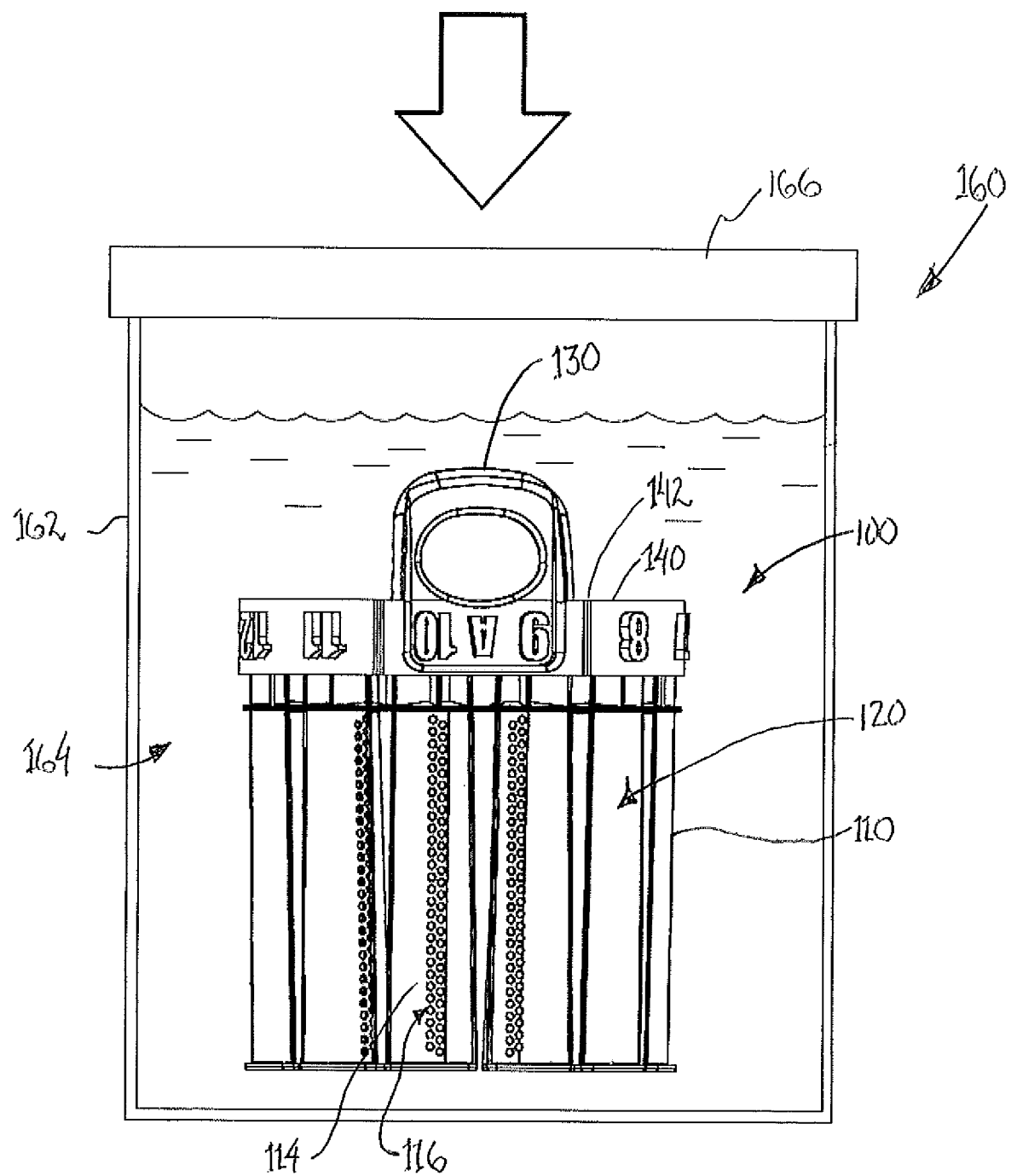
FIG. 5 depicts a front elevational view of the tissue sample tray of FIG. 3 disposed within a jar.

In some instances it may be desirable to insert tissue sample tray (100) in a preservative or other protective medium after collecting tissue samples within each tissue receiving chamber (120) of tissue sample tray (100). As seen in FIG. 5, in some examples tissue sample tray (100) may be used in connection with jar (160). Jar (160) is generally configured to receive one or more tissue sample trays (100) after collection of tissue samples using biopsy device (10). As will be described in greater detail below, jar (160) may be used to transport or store tissue samples once one or more tissue sample trays (100) are deposited therein.

In the present example, jar (160) includes a cup (162) and a lid (166). Cup (162) defines a reservoir (164), which can be used to contain fluid within cup (162). Cup (162) defines a generally cylindrical shape that is sized to receive one or more tissue sample trays (100). Lid (166) generally corresponds to the cylindrical shape of cup (162). Lid (166) is further configured to be selectively fastened onto a top portion of cup (162). In the present example, lid (166) includes seals or other features configured to seal cup (162) relative to the exterior of cup (162). As described above, reservoir (164) is generally configured to hold fluid. Thus, lid (166) is corresponding configured to hold the fluid within cup (162).

As described above, jar (160) is generally filled with fluid. Thus, when tissue sample tray (100) is disposed within jar (160), tissue sample tray (100) is generally at least partially submerged in fluid. In the present example, fluid is generally configured to act as a preservative of tissue samples contained within tissue sample tray (100). By way of example only, one suitable preservative may include formalin. However, it should be understood that in other examples numerous alternative fluids as will be apparent to those of ordinary skill in the art in view of the teachings herein.

II. Exemplary Tissue Processing Cassette

Once tissue samples have been collected using biopsy device (10) or other similar devices described herein, it may be desirable to subject such tissue samples to further pathological analysis. To facilitate such analysis, such tissue samples may be subjected to a variety of processing steps described in greater detail below. During these processing steps, it may be desirable to dispose the collected tissue samples within a container or other device to help segregate and track the collected tissue samples relative to other tissue sample collected from the same or other patients as well as the same or other biopsy procedures.

Figure 6:
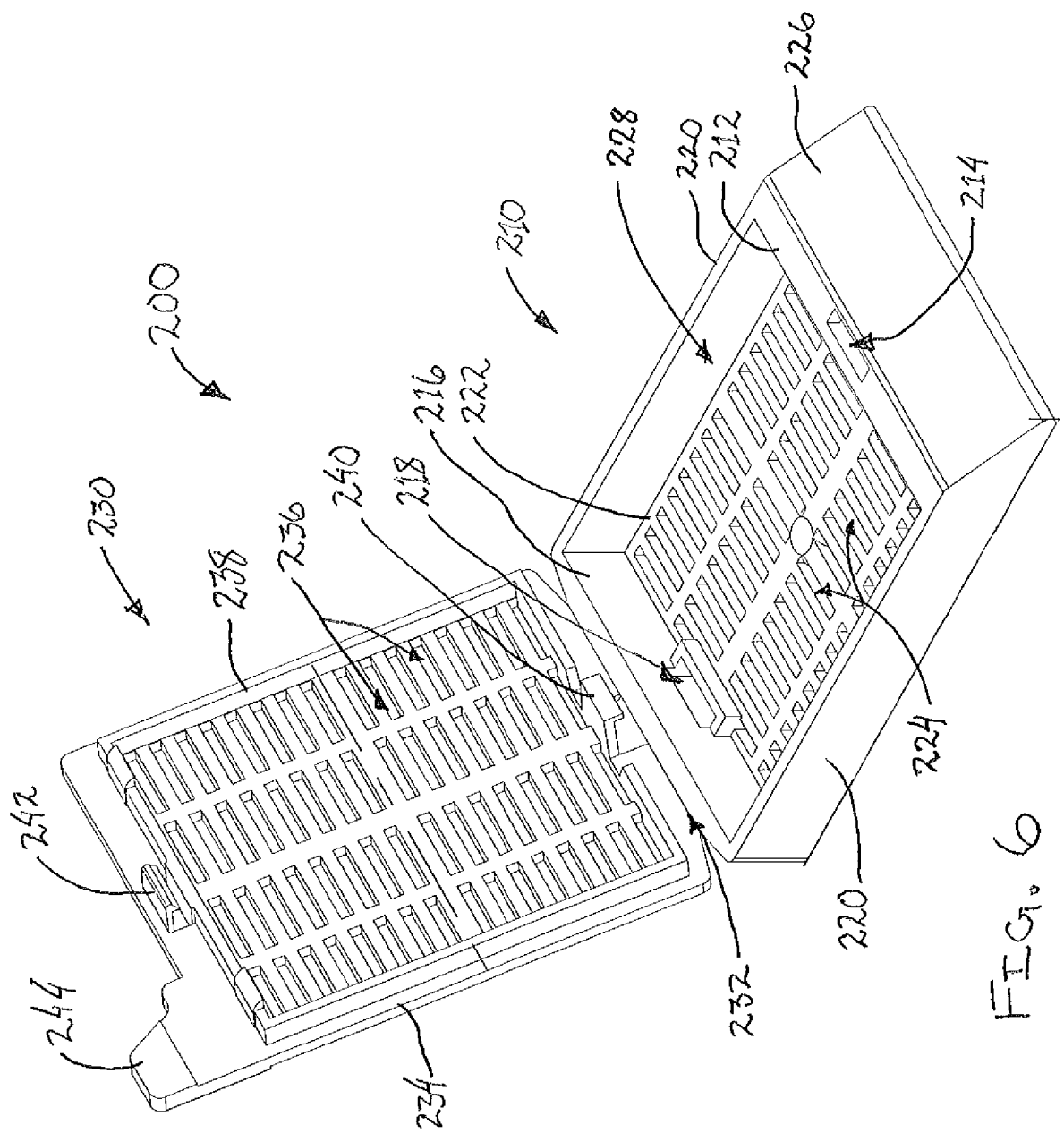
FIG. 6 depicts a perspective view of an exemplary sample cassette for use in processing tissue samples collected with the biopsy device of FIG. 1.

FIG. 6 shows an exemplary tissue processing cassette (200) that may be used in connection with biopsy device (10) to store and track tissue samples after collection via biopsy device (10). Tissue processing cassette (200) is generally configured to receive and enclose a plurality of tissue samples therein. As can be seen, tissue processing cassette (200) comprises a base (210) and a lid (230). Base (210) comprises a distal wall (212), a proximal wall (216), a pair of sidewalls (220), and a floor (222). Base (210) further includes a labeling surface (226) extending distally from distal wall (212).

Walls (212, 216, 220) are generally connected to form a rectangular pattern around floor (422). Each wall is generally solid, thereby forming a sample chamber (228) therein. As will be described in greater detail below, sample chamber (228) is generally configured to contain tissue samples within tissue processing cassette (200) when lid (230) is closed relative to base (210).

Distal wall (212) and proximal wall (216) each include a lid receiver (214, 218). Each lid receiver (214, 218) is generally configured to receive at least a portion of lid (230) to thereby selectively secure lid (230) to base (210). Although not shown, it should be understood that each lid receiver (214, 218) can include certain fastening features to facilitate securing lid (230) to base (210). As will be described in greater detail below, these fastening features generally facilitate a snap fit coupling mechanism. However, it should be understood that in other examples alternative coupling mechanisms may be used such as compression fit mechanisms, or any other suitable coupling mechanism as will be apparent to those of ordinary skill in the art in view of the teachings herein.

As described above, labeling surface (226) protrudes distally from distal wall (212).

Labeling surface (226) is generally configured to receive a label to provide information to an operator related to the samples contained within tissue processing cassette (200). Although labeling surface (226) of the present example can receive a label (e.g., a pre-printed self-adhering label), it should be understood labeling surface (226) is also configured to permit direct printing of a label onto labeling surface (226). For instance, in some examples labels are laser etched onto labeling surface (226) using a printer configured to receive tissue processing cassette (200) and thereby print directly onto labeling surface (226). To facilitate such printing, it should be understood that labeling surface (226) can also be equipped with a colored coating that can be etched away by the printer described above.

Floor (222) includes a plurality of vents (224) arranged in an array across the surface of floor (222). Vents (224) are generally configured to promote the flow of fluid through floor (222), yet maintain tissue samples within sample chamber (228). To facilitate this configuration, vents (224)

have a narrow rectangular form. In other examples, vents (224) can be configured with a variety of alternative shapes such as round, oval-shaped, square, and/or etc. Although vents (224) in the present example are arranged to uniformly occupy the entire surface of floor (222), it should be understood that in other examples vents (224) can be arranged in a variety of other ways. For instance, vents (224) can be isolated to a specific region or multiple regions of floor (222). Of course, other alternative arrangements for vents (224) will be apparent to those of ordinary skill in the art in view of the teachings herein.

Lid (230) comprises a cover portion (234) that is generally configured to engage base (210) to hold tissue samples within sample chamber (228) of base (210). Lid (230) further includes a lip (238) protruding from cover portion (234). Lip (238) extends around the perimeter of cover portion (234) defining a rectangular shape that corresponds to the rectangular shape defined by walls (212, 216, 220) of base (210). As will be understood, lip (238) is generally configured to fit within sample chamber (228) adjacent to each wall (212, 216, 220) to laterally secure and locate cover portion (234) relative to base (210) when lid (230) is in a closed position relative to base (210).

Like with floor (222) described above, cover portion (234) likewise includes a plurality of vents (236) arranged in an array across the surface of cover portion (234). Like vents (224) described above, vents (236) are generally configured to promote the flow of fluid through cover portion (234), yet maintain tissue samples within sample chamber (228). To facilitate this configuration, vents (236) have a narrow rectangular form. In other examples, vents (236) can be configured with a variety of alternative shapes such as round, oval-shaped, square, and/or etc. Although vents (236) in the present example are arranged to uniformly occupy the entire surface of cover portion (234), it should be understood that in other examples vents (236) can be arranged in a variety of other ways. For instance, vents (236) can be isolated to a specific region or multiple regions of cover portion (234). Of course, other alternative arrangements for vents (234) will be apparent to those of ordinary skill in the art in view of the teachings herein.

Lid (230) further comprises a proximal fastener (240) and distal fastener (242). Proximal fastener (240) is configured to engage lid receiver (218) of proximal wall (216), while distal fastener (242) is configured to engage lid receiver (214) of distal wall (212). Each fastener (240, 242) includes a tooth, lip, or other engagement feature that mates with a corresponding feature of each lid receiver (214, 218). As described above, this generally provides a snap fit coupling between each fastener (240, 242) and each lid receiver (216, 218) to selectively maintain lid (230) in the closed position.

Lid (230) is secured to proximal wall (216) of base (210) with an integral living hinge (232). Living hinge (232) permits pivoting of lid (230) relative to base (210) such that lid (230) may move between an open position (e.g., FIG. 6) and the closed position. This configuration permits tissue samples to be loaded into sample chamber (228) when lid (230) is in the open position. Lid (230) can then be pivoted to the closed position to secure the loaded tissue samples within sample chamber (228). To assist pivoting of lid (230), lid (230) further includes a manipulator (244) or thumb snap. Manipulator (244) generally protrudes distally from cover portion (234) to provide a gripping feature when lid (230) is in the closed position. This facilitates moving lid (230) from the closed position to the open position by providing a surface for an operator to grasp.

Figure 7:
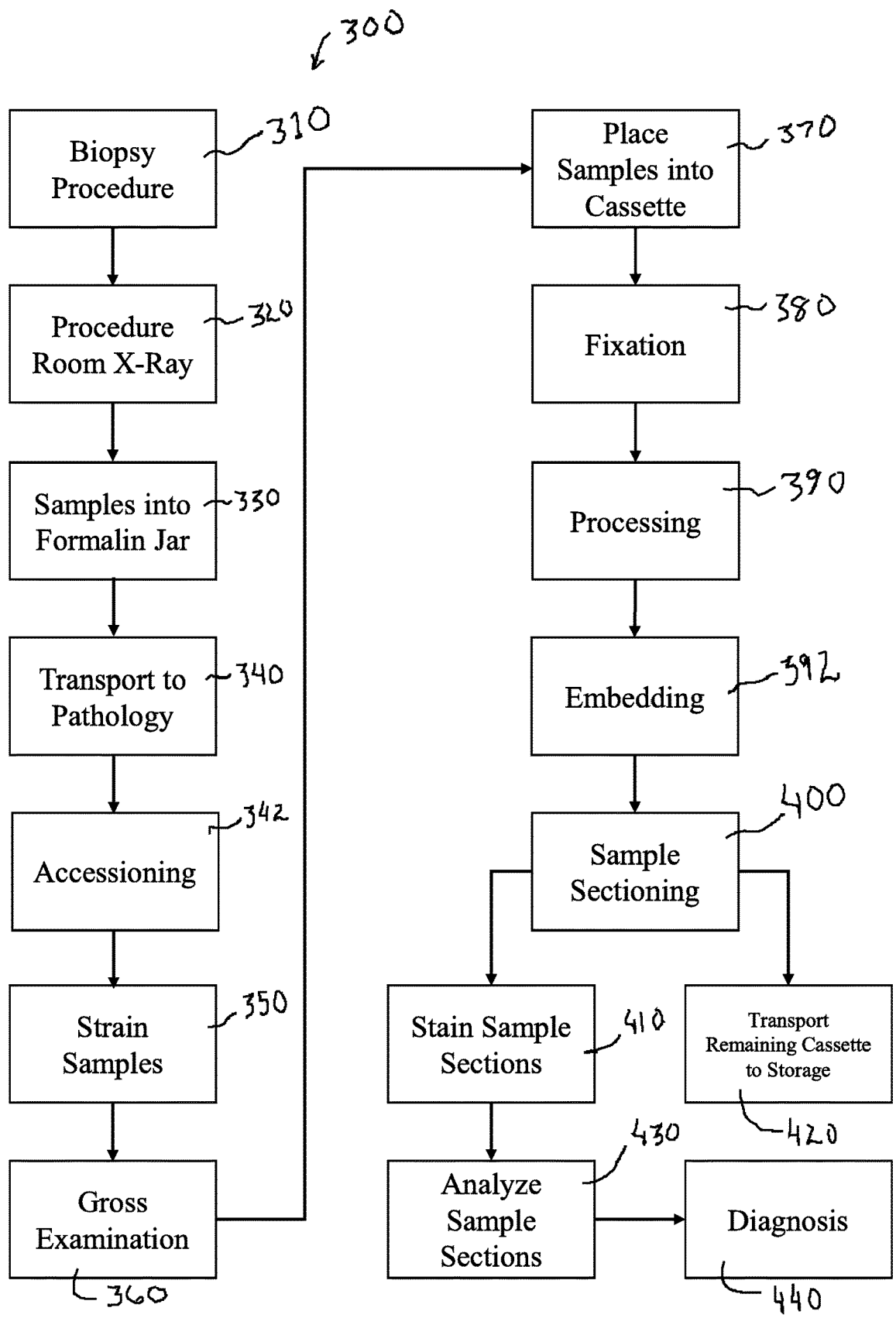
FIG. 7 depicts a flowchart of an exemplary tissue collection and analysis work flow for use with the biopsy device of FIG. 1 and the sample cassette of FIG. 6.
Figure 8:
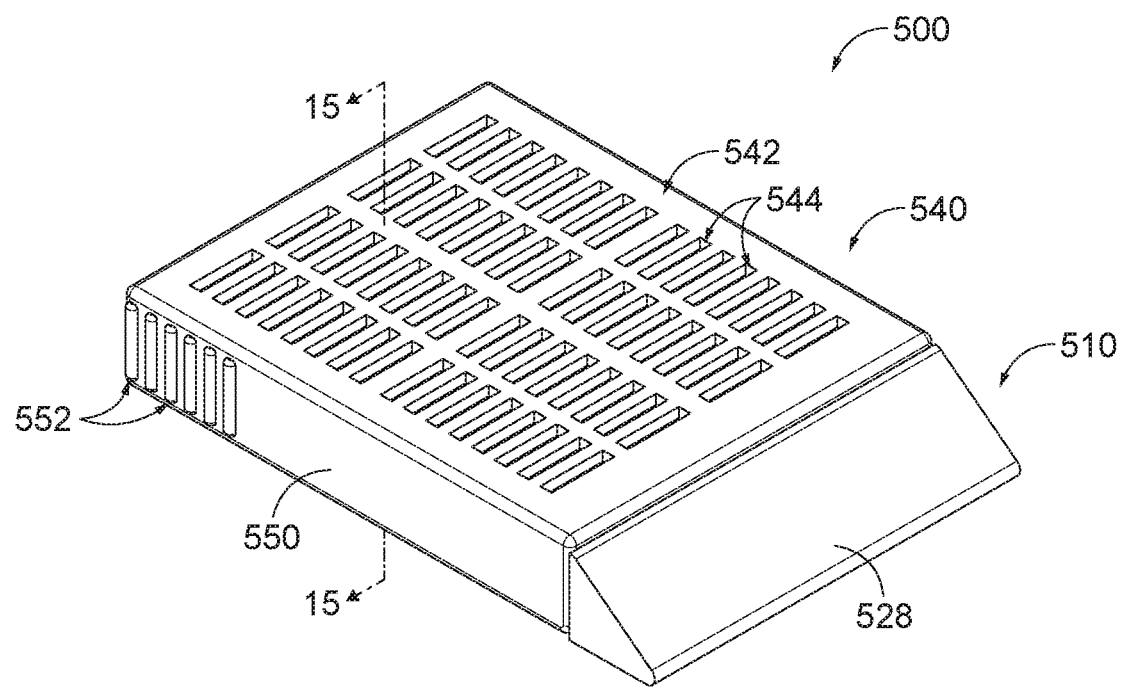
FIG. 8 depicts a perspective view of an exemplary cassette assembly that may be readily used with the biopsy device of FIG. 1 in lieu of the tissue sample tray of FIG. 3 and/or the sample cassette of FIG. 6.
Figure 9:
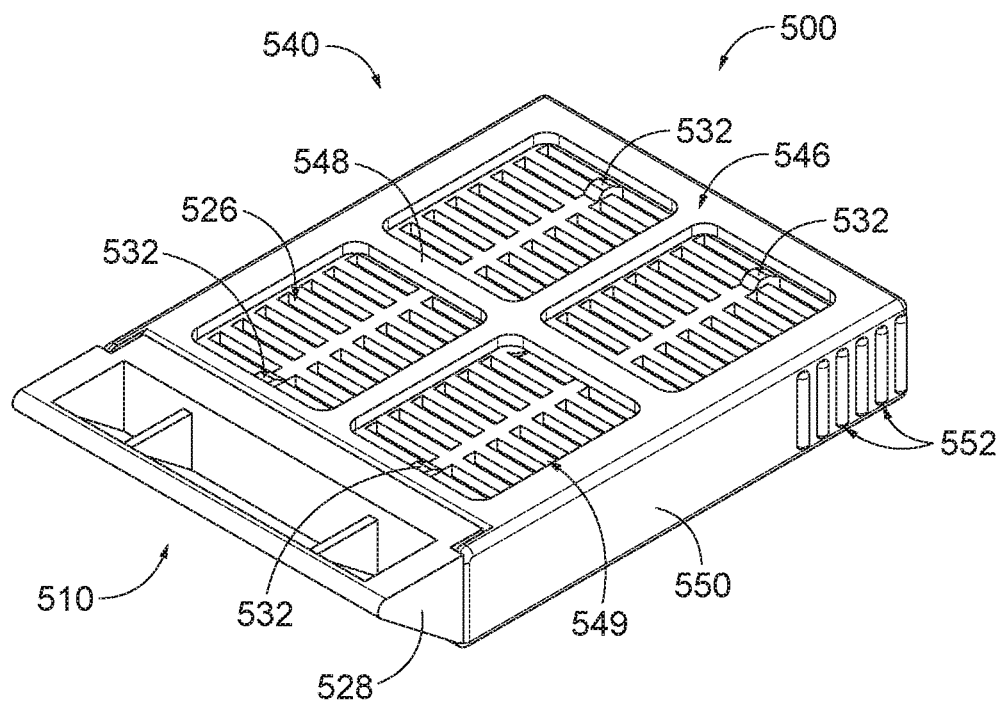
FIG. 9 depict another perspective view of the cassette assembly of FIG. 8.

As described above, tissue samples may be subjected to various processing and or analysis steps after the tissue samples are collected with biopsy device (10) or other suitable devices. During such steps, tissue processing cassette (200) can be used to facilitate transport, tracking, and storage of the collected tissue samples. In particular, FIG. 7 shows a generally workflow associated with biopsy device (10) and tissue processing cassette (200) described above. It should be understood that the workflow (300) shown in FIG. 7 and the description herein is only exemplary and that various alternative procedural steps may be used in addition and/or in the alternative to the steps shown in FIG. 7. For instance, in some examples biopsy device (10) and/or tissue processing cassette (200) may be used in accordance with one or more of the teachings of U.S. patrent application Ser. No. 15/638,843, entitled "Integrated Workflow for Processing Tissue Samples from Breast Biopsy Procedures," filed on Jun. 30, 2017, the disclosure of which is incorporated by reference herein.

In the workflow (300) shown in FIG. 7, tissue samples are collected during a biopsy procedure represented by box (310). During the biopsy procedure in box (310), biopsy device (10) may be used to collect a plurality of tissue samples into one or more tissue sample trays (100). Although the description above is primarily related to collection of tissue samples using a stereotactic biopsy procedure, it should be understood that various alternative procedures can be used such as ultrasonically guided procedures, Mill guided procedures, and/or etc. In addition, although the description above is primarily related to tissue sample collection using a multi-chamber-style tissue sample holder similar to tissue sample holder assembly (40), it should be understood that various alternative tissue sample collection devices may be used such as basket-style tissue sample holders. Alternatively, tissue samples can be collected without a tissue sample holder and may be merely plucked from a sample surface on a device similar to biopsy device (10).

Regardless of the particular process for collecting tissue samples, once tissue samples are collected, they may be subjected to procedure room x-ray as shown in box (320). During procedure room x-ray, an operator uses x-ray imaging in the procedure room to perform preliminary analysis on the collected tissue samples. During this stage, the collected tissue samples are primarily analyzed using x-ray imaging to determine if any one or more of the collected tissue samples include calcifications or other suspicious features identifiable via x-ray. After this preliminary analysis, more tissue samples can be acquired, if an operator is not satisfied with the preliminary analysis. Alternatively, an operator may be satisfied with the originally collected tissue samples and move to the next step in the procedure.

After an operator is satisfied with preliminary procedure room x-ray analysis, the operator may insert tissue sample tray (100) or just the tissue samples into jar (160). As described above, jar (160) may be filled with formalin or other fluids to preserve the collected tissue samples for storage and/or transport as represented by box (330). Jar (160) is then transported to a pathology laboratory so that the tissue samples can be subjected to further analysis as represented by box (340).

Once jar (160) is received by the pathology laboratory, the samples can be subjected to accessioning as represented by box (342). Accessioning (342) used herein refers to the process of documenting the chain of custody of the collected tissue samples. It should be understood that this may include a variety of steps. For instance, in some examples, jar (160)

can include a label that can be used to store, present, display, or otherwise provide patient information. This label can be printed during or after the biopsy procedure described above and represented by box (310). The label can then be adhered to jar (160) prior to transport to pathology as represented by box (340). Once jar (160) is received by pathology, an operator can record, scan, or otherwise collect information from the label to track the chain of custody of the collected tissue samples contained within jar (160).

Once accessioning is complete, the collected tissue samples are strained from the fluid contained within jar (160) as represented by box (350). The collected tissue samples then undergo gross examination by an operator as represented by box (360). Gross examination can include visual inspection of the collected tissue samples, palpitation of the collected tissue samples, and/or manipulating the collected tissue samples into a desired position. Preliminary observations can then be documented in a written record by an operator. Such written records can then be associated with the label described above with respect to accessioning and box (342).

After gross examination or during gross examination, the collected tissue samples are inserted into one or more tissue sample processing cassettes similar to tissue processing cassette (200) described above as represented by box (370). For instance, in the context of tissue processing cassette (200), each collected tissue sample is generally laid on floor (222) of base (210) longitudinally between distal wall (212) and proximal wall (216). Lid (230) is then pivoted to the closed position to enclose the collected tissue samples within sample chamber (228) of base (210). To promote tracking of the collected tissue samples, the tissue processing cassette can be labeled at this stage by either direct printing or adhering a self-adhering label to a structure similar to labeling surface (226) described above. This label can include certain patient information corresponding to the label described above with respect to accessioning and box (342).

Once the collected tissue samples are disposed within a tissue processing cassette similar to tissue processing cassette (200), the collected tissue samples are subjected to fixation as represented by box (380). The term fixation used herein refers to the process of using a fixative to preserve specimen integrity and to maintain the shape of cells. Generally, this process involves submerging the collected tissue samples within a fixative. One common fixative is 10% neutral buffered formalin, although other fixatives can be used. The collected tissue samples can be maintained within the fixative for a predetermined period of time. Suitable periods of time can vary according to a variety of factors. However, under many circumstances, a suitable period of time can be approximately 6 hours. This period is generally sufficient to provide stabilization of the proteins in the collected tissue samples to substantially prevent degeneration of the collected tissue samples.

After fixation is complete, the collected tissue samples are subjected to various chemical solutions during the processing step represented by box (390). During this process, multiple tissue processing cassettes may be loaded into a basket for bulk processing. Various chemicals are then applied, which may enter each tissue processing cassette via vents similar to vents (224, 236) described above. Various chemicals may be used during this process such as alcohols of various concertation levels. For instance, when alcohol is used, moisture is removed from each collected tissue sample rendering each collected tissue sample hard in texture and generally dehydrated.

Once processing is complete, the collected tissue samples are subjected to an embedding process represented by box (392). During the embedding process, the collected tissue samples are surrounded by a histological wax. In one merely exemplary embedding process, the tissue samples are removed from the tissue processing cassette and placed into a metal tray or container. Prior to placement of the tissue samples within the metal tray, the metal tray can be partially filled with an initial amount of molten wax. Once the samples are placed in the metal tray, the metal tray is then filled with molten wax. The tissue processing cassette is then placed on the top of the metal tray with the underside of the cassette facing the tissue samples. Additional molten wax is then added through the cassette to bond with wax in the metal tray. During this process, the metal tray can be placed on a cold plate or other cold surface to provide relatively quick solidification of the wax. Once solidification is complete, the collected tissue samples and cassette can be removed from the metal tray. It should be understood that once the tissue samples are prepared in this manner, the tissue samples are generally preserved for indefinite storage at room temperature.

After the embedding process is complete, thin slices of each collected tissue sample are acquired as represented by box (400). Sample sectioning may be performed using a microtome machine. Such a machine uses precision blades to slice thin samples longitudinally from each collected tissue sample. The thin sections are then placed on slides for viewing under suitable visualization means such as optical microscopes.

Once the tissue sample sections are placed on a slide, the sections are subjected to staining as represented by box (410). The portion of the collected tissue samples that remain in the tissue processing cassette are transported to storage as represented by box (420). During the staining process, various chemical compounds are applied to the tissue sample sections. Each chemical compound may be configured to react to different tissue cells. For instance, some compounds may be configured to specifically react with cancer cells, thereby staining cancer cells with a distinctive color relative to other cells. Although not represented in FIG. 7, it should be understood that in some examples the staining process can include multiple stages of staining. For instance, in some examples staining can include primary staining followed by advanced staining.

Once staining is complete, the stained sample sections are analyzed by an operator using a microscope or other visualization means as represented by box (430). Based on this analysis a diagnosis may be generated as represented by box (440).

III. Exemplary Integrated Tissue Collection and Processing System

In some instances, it may be desirable to combine certain elements of the tissue sample holder assembly (40) described above with the tissue analysis cassette (200) described above. For instance, manipulation of tissue samples generally risks degrading the quality of the tissue samples each time the tissue samples are manipulated due to the fragility of the tissue. Transferring tissue samples between elements like tissue sample tray (100) described above and tissue processing cassette (200) described above often result in at least some manipulation of the tissue samples being transferred. Thus, transferring tissue samples between various elements may be undesirable in certain circumstances because this can lead to degradation of tissue sample quality. It is therefore desirable to reduce the number of containers used to deposit tissue samples during the workflow (300) described above.

In addition to manipulation of tissue samples being generally undesirable, transferring tissue samples between different containers (e.g., tissue sample tray (100), tissue processing cassette (200)) can lead to mislabeling or tacking errors associated with tissue samples as the tissue samples progress through the workflow (300) described above. For instance, when tissue sample are transferred from tissue sample tray (100) to tissue processing cassette (200), incorrect patient information might be printed on tissue processing cassette (200). Another possibility is that an incorrect label may be placed on tissue processing cassette (200). Thus, transferring tissue samples between different containers also includes the risk of generating errors in tissue sample tracking. Accordingly, it is desirable to reduce the number of containers used in the workflow (300) described above to generally improve tissue sample integrity and reduce operator error.

Although various devices and methods are described below for reducing the number of containers used in the workflow (300) described above are described herein, it should be understood that various alternative configurations will be apparent to those of ordinary skill in the art in view of the teachings herein. For instance, some suitable alternative configurations may combine various features of one embodiment described below with various features of another alternative embodiment. Still other suitable alternative configurations may omit various features of one or more embodiments. Of course, other suitable configurations will be apparent to those of ordinary skill in the art in view of the teachings herein.

A. Exemplary Cassette Assembly

FIGS. 8-14 show and exemplary cassette assembly (500) that may be used with biopsy device (10) described above. As will be understood, cassette assembly (500) is generally configured to receive tissue samples during a biopsy procedure and then continue to contain the tissue samples after the biopsy procedure and through various sample analysis procedures. In other words, cassette assembly (500) can be used in lieu at least tissue processing cassette (200) described above. In addition, cassette assembly (500) may also be used in lieu of tissue sample tray (100), as will be described in greater detail below. However, in some uses, cassette assembly (500) may merely be supplementary to tissue sample tray (100) or other analogous features (e.g., a bulk sample basket).

Figure 10:
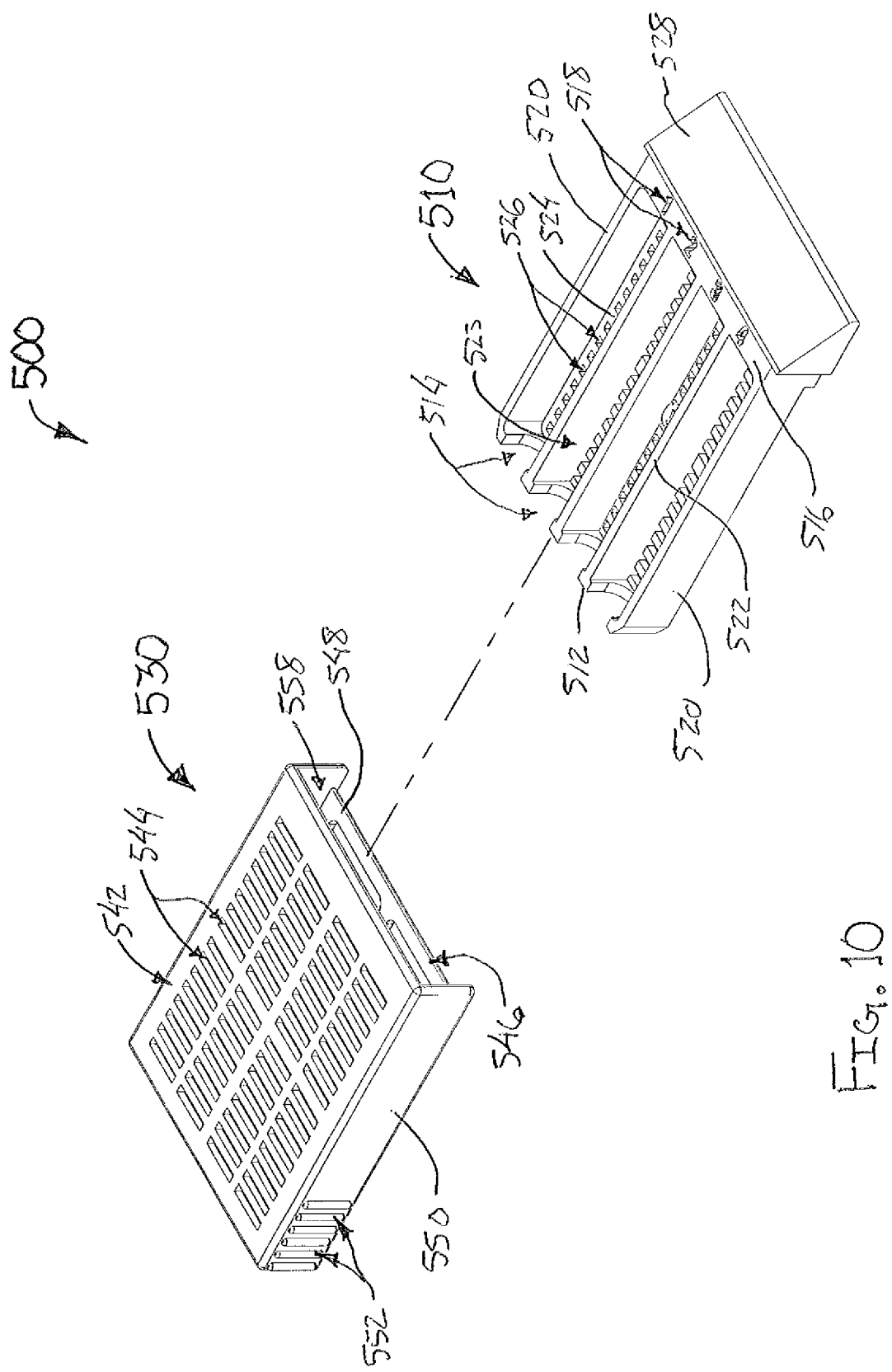
FIG. 10 depicts an exploded perspective view of the cassette assembly of FIG. 8.

As best seen in FIG. 10, cassette assembly (500) includes a cassette tray (510) and a cover (540). Cassette tray (510) comprises a distal wall (512), a proximal wall (516), a pair of sidewalls (520) extending between distal wall (512) and proximal wall (516), and a floor (524) positioned below walls (512, 516, 520). Distal wall (512) includes a plurality of openings (514) evenly spaced laterally across the face of distal wall (512). As will be described in greater detail below, each opening (514) is generally configured to receive a tissue sample. Proximal wall (516), by contrast, is solid. However, unlike distal wall (512), proximal wall (516) includes a plurality of indicia (518) on the upper surface of proximal wall (516). In the present example, indicia (518) form a plurality of unique numerical identifiers. In other examples, indicia (518) may take a variety of forms such as letters or discrete shapes or symbols.

Walls (512, 516, 520) are interconnected to form the outer perimeter of cassette tray (510). Internally, cassette tray (510) includes a plurality of inner divider walls (522) extending longitudinally from distal wall (512) to proximal wall (516). Each inner divider wall (522) is positioned parallel relative to sidewalls (520) an equal distance apart to define a plurality of discrete sample chambers (523). Each sample chamber (523) is generally configured to hold a single tissue sample severed by biopsy device (10). Although the present example includes four discrete sample chambers (523), it should be understood that in other examples any other suitable number of sample chambers (523) can be used. In such examples, it should be understood that each sample chamber (523) can be configured for receiving more than a single tissue sample as with sample chambers (523) in the present example.

Floor (524) is positioned below walls (512, 516, 520, 522). In the present example, each wall (512, 516, 520, 522) is integral with each wall. However, in other examples one or more of each wall (512, 516, 520, 522) can be separate from floor (524) and attached with adhesive or some form of mechanical fastening. Floor (524) includes a plurality of vents (526) or openings. Vents (526) are generally configured to promote the flow of fluid through floor (524), yet maintain tissue samples within each sample chamber (523). To facilitate this configuration, vents (526) have a narrow rectangular form. In other examples, vents (526) can be configured with a variety of alternative shapes such as round, oval-shaped, square, and/or etc. Although vents (526) in the present example are arranged to uniformly occupy the entire surface of floor (524), it should be understood that in other examples vents (526) can be arranged in a variety of other ways. For instance, vents (526) can be isolated to a specific region or multiple regions of floor (524). Of course, other alternative arrangements for vents (526) will be apparent to those of ordinary skill in the art in view of the teachings herein.

Floor (524) is opposite to an open space above each sample chamber (523). Thus, the upper portion of cassette tray (510) is generally open. Because of this, tissue samples may be deposited into each sample chamber (523) through openings (514) in distal wall (512) or through the open upper portion of cassette tray (510). As will be described in greater detail below, tissue samples are generally contained within each sample chamber (523) once cassette tray (510) is received within cover (540).

Cassette tray (510) further includes a labeling portion (528) protruding proximally from proximal wall (516). Labeling portion (528) generally defines a triangular or wedge shape that provides a flat smooth surface for printing or otherwise adhering a label to the surface of labeling portion (528). As similarly described above with respect to labeling surface (226) of tissue processing cassette (200), labeling portion (528) is generally configured to provide readily accessible patient information to an operator to aid with tracking of tissue samples as they progress through the biopsy and sample analysis procedure.

Unlike labeling surface (226) described above with respect to tissue processing cassette (200), at least a portion of labeling portion (528) is generally oversized relative to the height of sidewalls (520) or the lateral length of proximal wall (516). This feature generally provides a blocking or sealing feature for cassette tray (510) to promote the flow of fluid through cassette tray (510). As will be described in greater detail below, cassette tray (510) is generally insertable into cover (540) or other suitable components. When inserted into cover (540) or other suitable components, labeling portion (528) blocks at least a portion of cover (540) and/or other components to force fluid flow through vents (526) rather than other features of cassette tray (510).

Figure 12:
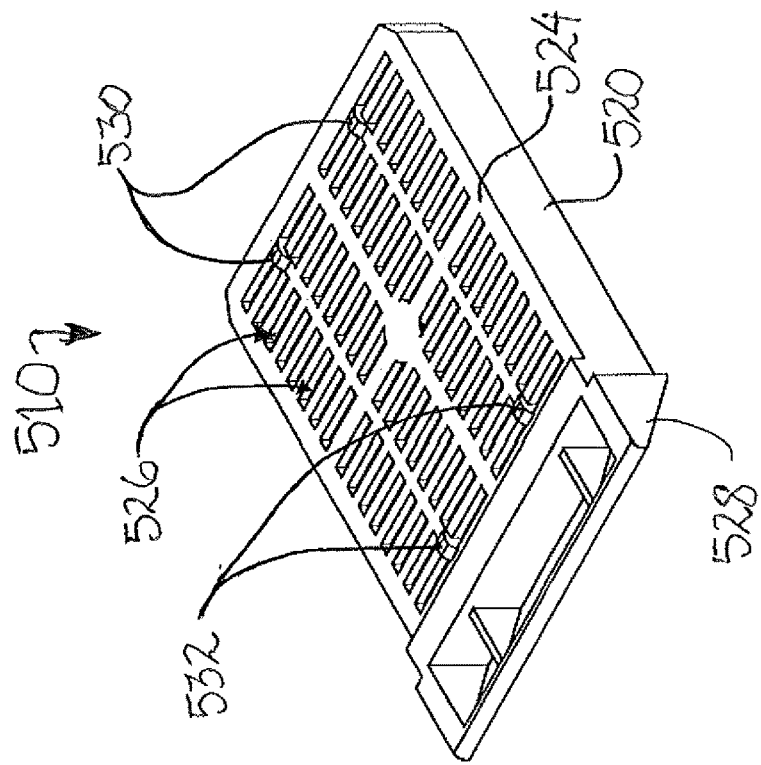
FIG. 12 depicts another perspective view of the cassette tray of FIG. 11.
Figure 11:
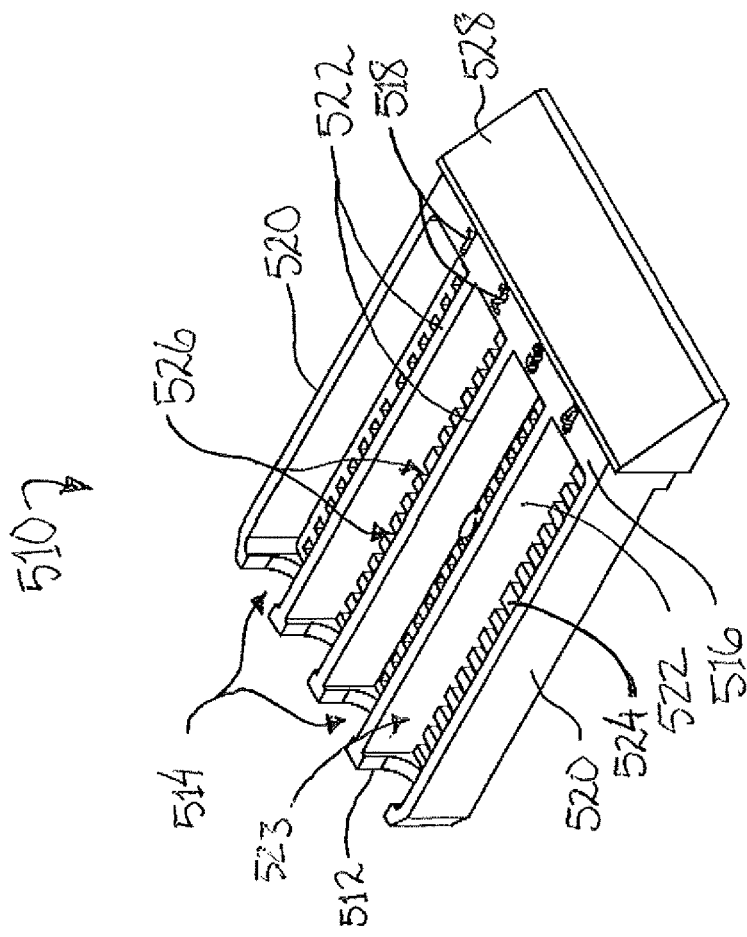
FIG. 11 depicts a perspective view of an exemplary cassette tray of the cassette assembly of FIG. 8.

As best seen in FIG. 12, cassette tray (510) further comprises a plurality of detents (530, 532) disposed on the underside of floor (524). As can be seen, cassette tray (510) comprises a pair of distal detents (530) and a pair of proximal detents (532). Distal detents (530) are positioned approximately adjacent to distal wall (512), while proximal detents (532) are positioned approximately adjacent to proximal wall (516). As will be described in greater detail below, each pair of detents (530, 532) is positioned to provide temporary or selective locking of cassette tray (510) at various positions relative to cover (540) when cassette tray (510) is inserted into cover (540). Although detents (530, 532) are shown as having a generally rectangular shape with rounded corners, it should be understood that various alternative shapes may be used in other examples. For instance, detents (530, 532) can be hemispherical, oval-shaped, triangular, and/or etc.

Figure 13:
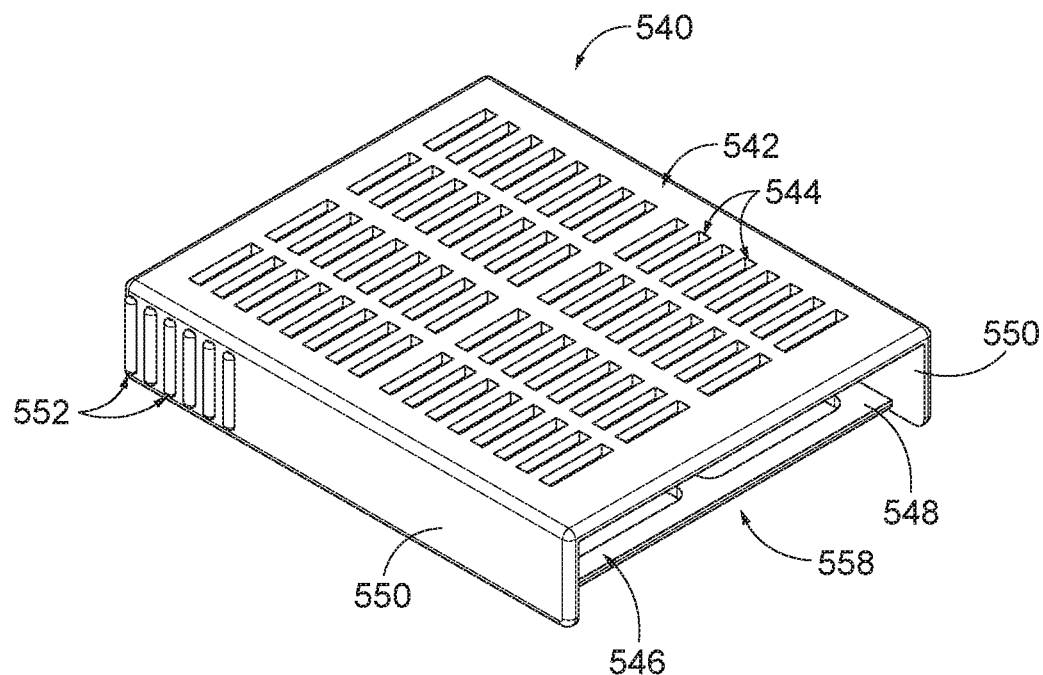
FIG. 13 depicts a perspective view of an exemplary cover of the cassette assembly of FIG. 8.
Figure 14:
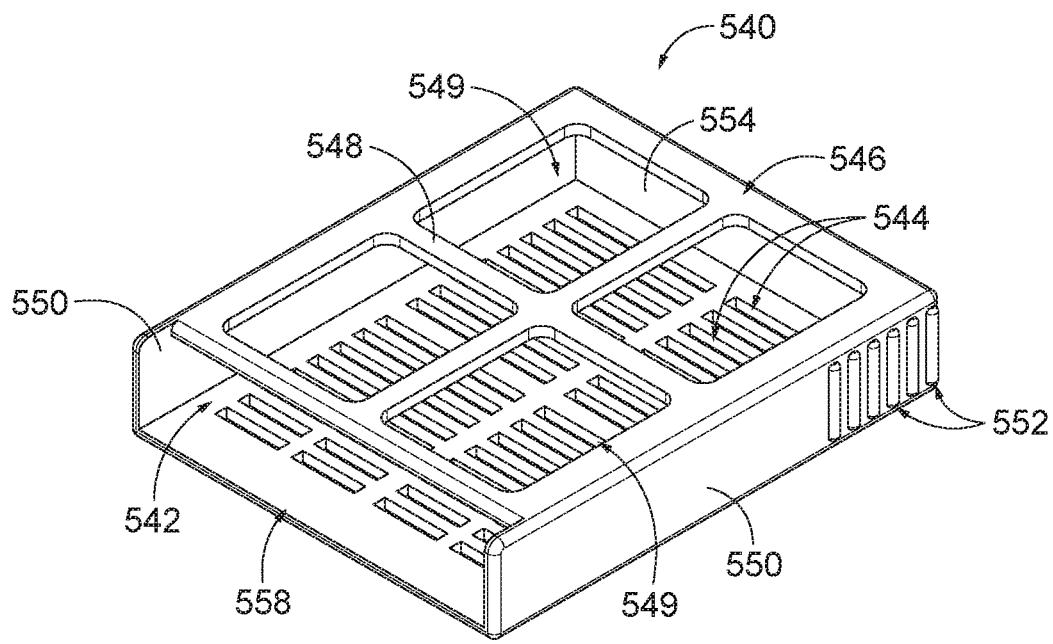
FIG. 14 depicts another perspective view of the cover of FIG. 13.

FIGS. 13 and 14 show cover (540) in greater detail. As can be seen, cover (540) comprises a filter portion (542), a support portion (546), and a plurality of walls (550, 554) extending between the filter portion (542) and the support portion (546). Filter portion (542) is similar to floor (524) described above in that filter portion (542) includes a plurality of vents (544) arranged in an array about the surface of filter portion (542). Vents (544) are generally configured to promote the flow of fluid through filter portion (542), yet maintain tissue samples within each sample chamber (523) of cassette tray (510) when cassette tray (510) is inserted into cover (540). To facilitate this configuration, vents (544) have a narrow rectangular form. In other examples, vents (544) can be configured with a variety of alternative shapes such as round, oval-shaped, square, and/or etc. Although vents (544) in the present example are arranged to uniformly occupy the entire surface of filter portion (542), it should be understood that in other examples vents (544) can be arranged in a variety of other ways. For instance, vents (544) can be isolated to a specific region or multiple regions of filter portion (542). Of course, other alternative arrangements for vents (544) will be apparent to those of ordinary skill in the art in view of the teachings herein.

Unlike filter portion (542), support portion (546) omits structures similar to vents (544). Instead, support portion (546) includes a support structure (548) defining a plurality of open spaces (549). As will be understood, support portion (546) is generally adjacent to floor (524) of cassette tray (510) when cassette tray (510) is inserted into cover (540). Thus, including structures similar to vents (544) is not entirely necessary due to the presence of vents (526) in floor (524) of cassette tray (510). However, it should be understood that in some examples support portion (546) may include structures similar to vents (544).

Support structure (548) forms a generally cross-shaped pattern in support portion (546). This structure is generally configured to provide rigidity to cover (540) and is further configured to hold cassette tray (510) within cover (540) when cassette tray (510) is disposed within cover (540). Although support structure (548) forms a generally cross-shaped pattern in the present example, it should be understood that in other examples support structure (548) can take on a variety of other forms. For instance, in some examples support structure (548) can have a lath-shaped structure. In other examples, support structure (548) can have a lattice shaped structure. In still other examples, support structure (548) can be formed of a plurality of concentric circles, or any other configuration as will be apparent to those of ordinary skill in the art in view of the teachings herein.

Support structure (548) is further configured to interact with detents (530, 532) of cassette tray (510). As will be described in greater detail below, cassette tray (510) is generally insertable into cover (540) at a plurality of discrete positions relative to cover (540). During insertion, detents (530, 532) of cassette tray (510) interact with support structure (548) to bias cassette tray (510) towards each discrete position. Due to the cross-shaped pattern of support structure (548), support structure (548) provides three discrete positions of cassette tray (510) relative to cover (540). Of course, in other examples where support structure (548) defines a different shape, support structure (548) can provide more or less discrete positions for cassette tray (510) relative to cover (540).

With the cross-shaped pattern of support portion (546), support portion (546) defines four total open spaces (549). Open spaces (549) are generally configured to promote fluid flow through cover (540) between vents (544) of filter portion (542) and open spaces (549). As will be described in greater detail below, this permits fluid to flow through cassette tray (510) when cassette tray (510) is disposed within cover (540).

As described above, cover (540) includes a plurality of walls (550, 554) extending between filter portion (542) and support portion (546). Walls (550, 554) include a pair of sidewalls (550) and a distal wall (554). Sidewalls (550) and distal wall (554) are both solid to generally promote rigidity of cover (540). Each sidewall (550) includes a plurality of grips (552), which promote manipulation of cover (540) by an operator. Walls (550, 554) together with filter portion (542) and support portion (546) together are configured to define an enclosure for cassette tray (510) that holds tissue samples within cassette tray (510), while permitting fluid to flow through cassette tray (510).

Opposite distal wall (554), filter portion (542), support portion (546), and sidewalls (550) define a proximal opening (558). Proximal opening (558) is generally configured to receive at least a portion of cassette tray (510) such that cassette tray (510) may be inserted into cover (540). Although proximal opening (558) is shown in the present example as having a generally rectangular shape, it should be understood that proximal opening (558) is generally a function of the shape of cover (540) and cassette tray (510). Thus, in examples where cassette tray (510) and/or cover (540) take on different shapes, proximal opening (558) may also be correspondingly different.

Figure 15A:
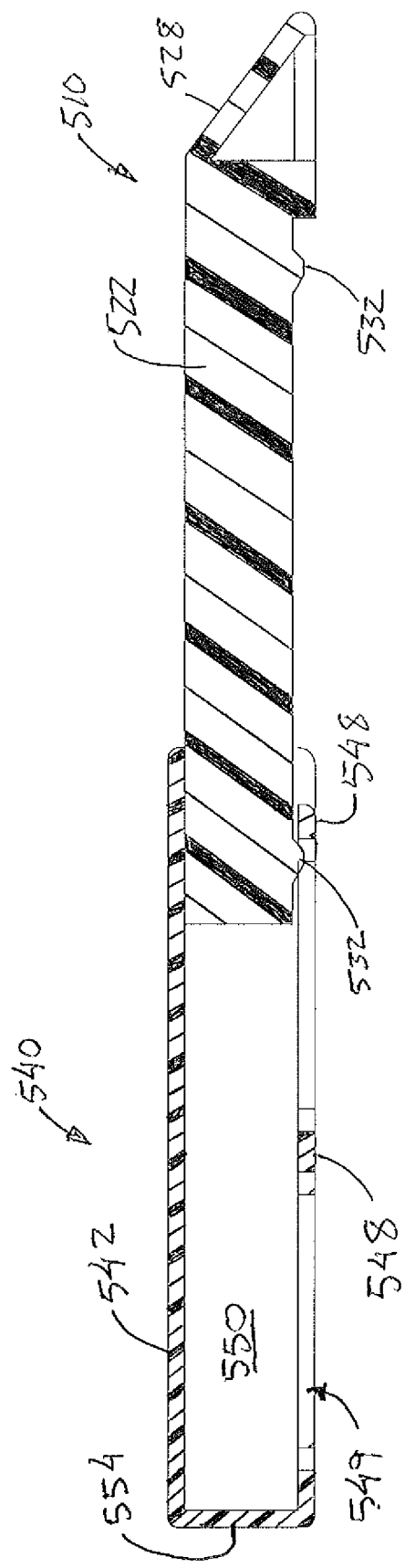
FIG. 15A depicts a side cross-sectional view of the cassette assembly of FIG. 8, with the cassette tray of FIG. 11 initially inserted into the cover of FIG. 13.
Figure 15B:
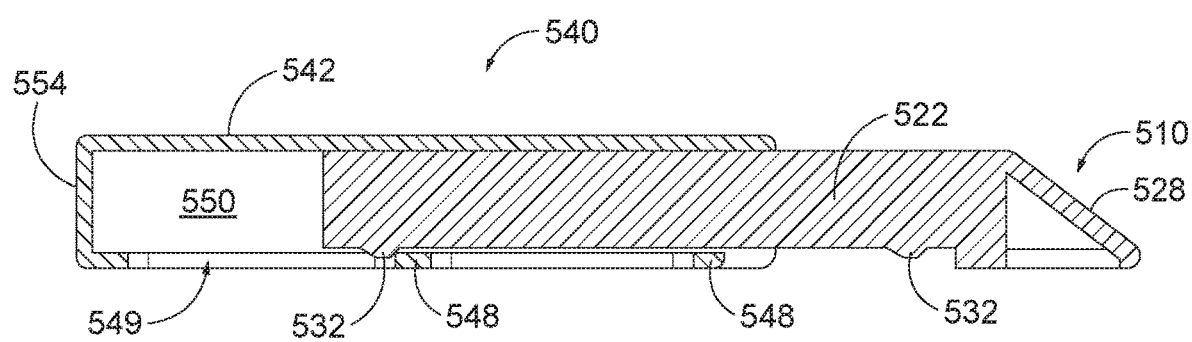
Figure 15C:
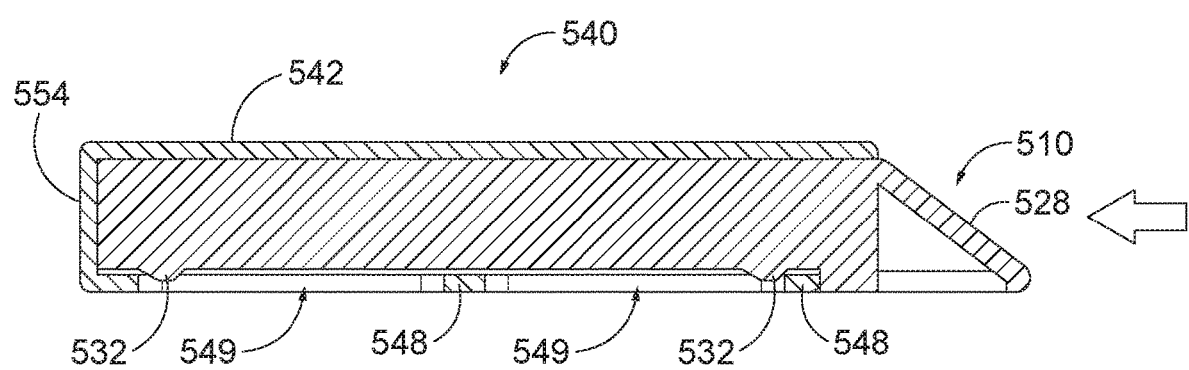
FIG. 15C depicts still another side cross-sectional view of the cassette assembly of FIG. 8, with the cassette tray of FIG. 11 fully inserted into the cover of FIG. 13.
Figure 16:
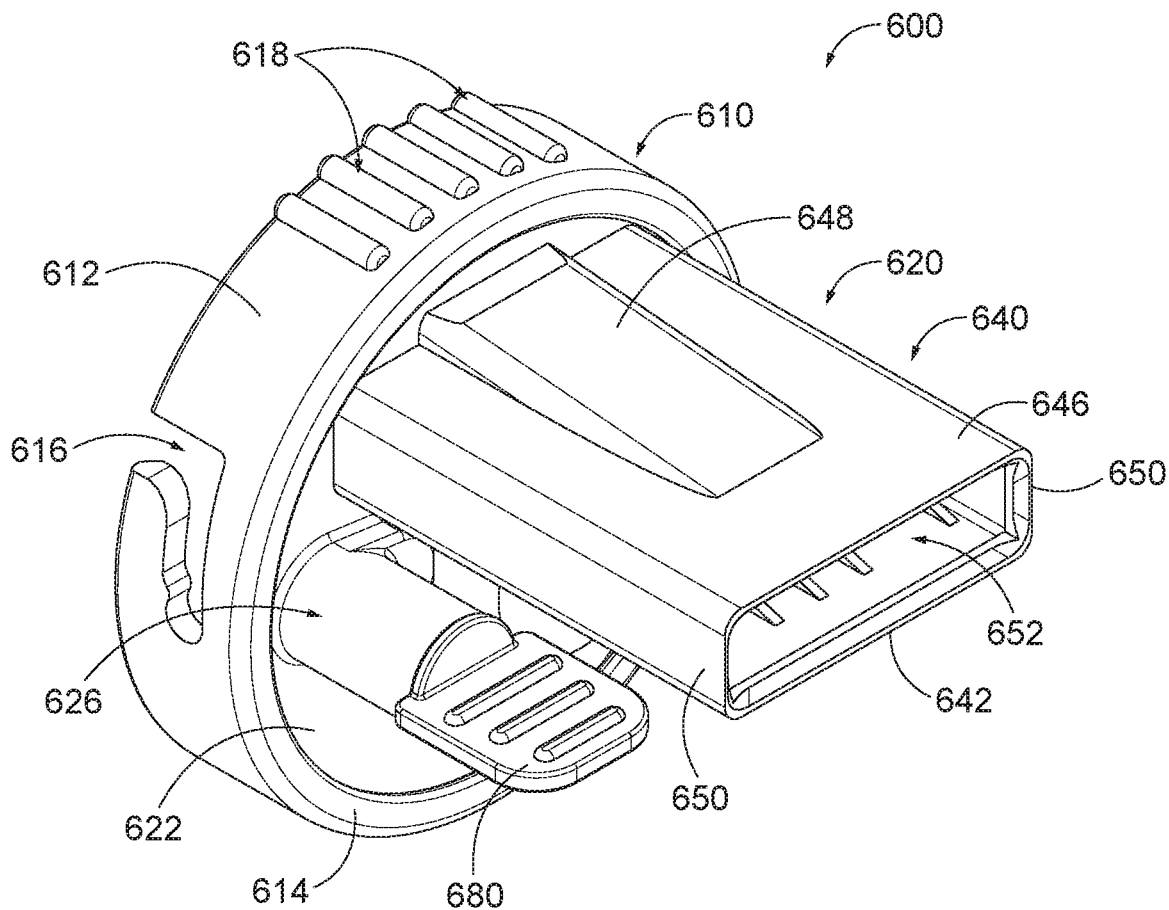
FIG. 16 depicts a perspective view of an exemplary alternative tissue sample holder assembly that can be readily incorporated into the biopsy device of FIG. 1.

FIGS. 15A-15C show an exemplary insertion of cassette tray (510) into cover (540). As will be described in greater detail below, insertion of cassette tray (510) into cover (540) generally occurs during a biopsy procedure after tissue samples have been collected by biopsy device (10) and inserted into cassette tray (510).

Although not shown, it should be understood that in some examples cover (540) can be color coded to correspond to various procedure related information. For instance, in some examples cover (540) can be red to indicate to an operator that samples contained therein require urgent processing. In other examples, different colored covers (540) can correspond to a different pathology laboratory technician or different pathology laboratory to help route the combination of cassette tray (510) and cover (540) through the pathology laboratory. Regardless of the particular color scheme, it should be understood that in use a plurality of covers (540) of different colors may be readily accessible to an operator such that an operator may choose a particular color at various stages. By way of example only, a plurality of covers (540) can come in a cover kit. Such a kit may include a cover (540) colored in red, blue, green, grey, pink, and yellow. Optionally, cassette tray (510) can also be colored. However, in some circumstances it may be desirable to maintain cassette tray (510) as a neutral color because certain pigments may interact with x-ray radiation adversely. Of course, various alternative uses of colorized variants of cover (540) can be used as will be apparent to those of ordinary skill in the art in view of the teachings herein.

As can be seen in FIG. 15A, the distal end of cassette tray (510) is initially inserted into proximal opening (558) of cover (540). As cassette tray (510) is inserted into proximal opening (558) of cover (540), distal detents (530) engage support structure (548) of support portion (546). Further insertion of cassette tray (510) into cover (540) causes distal detents (530) to flex over support structure (548) before releasing into the open spaces (549) that are oriented proximally on support portion (546).

Once distal detents (530) are disposed within the open spaces (549) that are oriented proximally on support portion (546) as shown in FIG. 15A, cassette tray (510) is generally removably secured within cover (540). In this context, "removably secured" refers to how cassette tray (510) is generally restricted from being pulled proximally out of cover (540). However, it should be understood that cassette tray (510) may still be pulled proximally out of cover (540) if a sufficient amount of force is applied to flex distal detents (530) upwardly onto support structure (548). At the same time, it should be understood that cassette tray (510) remains freely translatable in the distal direction such that cassette tray (510) can be advanced further into cover (540). In the position shown in FIG. 15A, cassette tray (510) can be optionally used by an operator while partially disposed within cover (540). By way of example only, this may be desirable for positioning or repositioning tissue samples within cassette tray (510).

Once cassette tray (510) is initially inserted into cover (540), an operator can insert cassette tray (510) further into cover (540) in the proximal direction towards the position shown in FIG. 15B. Cassette tray (510) is freely insertable in the proximal direction until distal detents (530) again engage support structure (548). Once distal detents (530) are engaged with support structure (548), an operator can apply a force to cassette tray (510) or cover (540) to flex distal detents (530) onto support structure (548) (or to flex support structure (548) out of the way of distal detents (530)).

Once distal detents (530) are clear of support structure (548), distal detents (530) will flex back to their original position and into the open spaces (549) oriented distally on cover (540). Once distal detents (530) are disposed within the open spaces (549) that are oriented distally on support portion (546) as shown in FIG. 15B, cassette tray (510) is generally removably secured within cover (540). Similar to the context above, "removably secured" here refers to how cassette tray (510) is generally restricted from being pulled proximally out of cover (540). However, it should be understood that cassette tray (510) may still be pulled proximally out of cover (540) if a sufficient amount of force is applied to flex distal detents (530) upwardly onto support structure (548). At the same time, it should be understood that cassette tray (510) remains freely translatable in the distal direction such that cassette tray (510) can be advanced further into cover (540). In the position shown in FIG. 15B, cassette tray (510) can be optionally used by an operator while partially disposed within cover (540). By way of example only, this may be desirable for positioning or repositioning tissue samples within cassette tray (510).

Once cassette tray (510) is inserted into cover (540) to the position shown in FIG. 15B, an operator may desire to insert cassette tray (510) fully into cover (540). To insert cassette tray (510) fully into cover (540), an operator may move cassette tray (510) distally relative to cover (540) towards the position shown in FIG. 15C. As cassette tray (510) is moved distally relative to cover (540), proximal detents (532) will engage support structure (548) of cover. At this point, an operator can apply a force to either cassette tray (510) or cover (540) that is sufficient to flex proximal detents (532) upwardly and onto support structure (548) (or flex support structure (548) out of the way of proximal detents (532)). Cassette tray (510) can then proceed further distally until proximal detents (532) flex downwardly to their original position and into the open spaces (549) oriented proximally on cover (540) as shown in FIG. 15C.

Once cassette tray (510) is positioned relative to cover (540) as shown in FIG. 15C, further distal movement of cassette tray (510) is prevented by engagement between distal wall (512) of cassette tray (510) and distal wall (554) of cover (540). In addition, as described above, labeling portion (528) is generally oversized relative to the dimensions of proximal wall (516) of cassette tray (510) and sidewalls (520) of cassette tray (510). Accordingly, labeling portion (528) can also act to stop further distal movement of cassette tray (510) by engagement between labeling portion (528) and support portion (546), sidewalls (550), and filter portion (542) of cover (540). In addition, it should be understood that in some contexts filter portion (542) can also act as a seal to seal proximal opening (558) of cover (540) relative to the exterior of cover (540). In such circumstances, this sealing can act to force fluid through vents (526, 544) rather than proximal opening (558).

B. Exemplary Alternative Tissue Sample Holder Assembly

In some examples it may be desirable to use cassette tray (510) in connection with biopsy device (10) such that tissue samples are collected directly into cassette tray (510) rather than into a structure similar to tissue sample tray (100) described above. Because cassette tray (510) includes a generally rigid structure, it should be understood that cassette tray (510) is generally not insertable directly into rotatable member (44) described above. Instead, it may be desirable to replace tissue sample holder assembly (40) with an alternative tissue sample holder assembly to facilitate use of cassette tray (510) directly with biopsy device (10). As described above, tissue sample holder assembly (40) is generally configured to be completely removable from probe assembly (20) of biopsy device (10). Thus, a suitable alternative tissue sample holder assembly may be used in lieu of tissue holder assembly (40), provided certain vacuum and tissue sample collection couplings remain consistent between the suitable alternative tissue sample holder assembly and tissue sample holder assembly (40).

Figure 17:
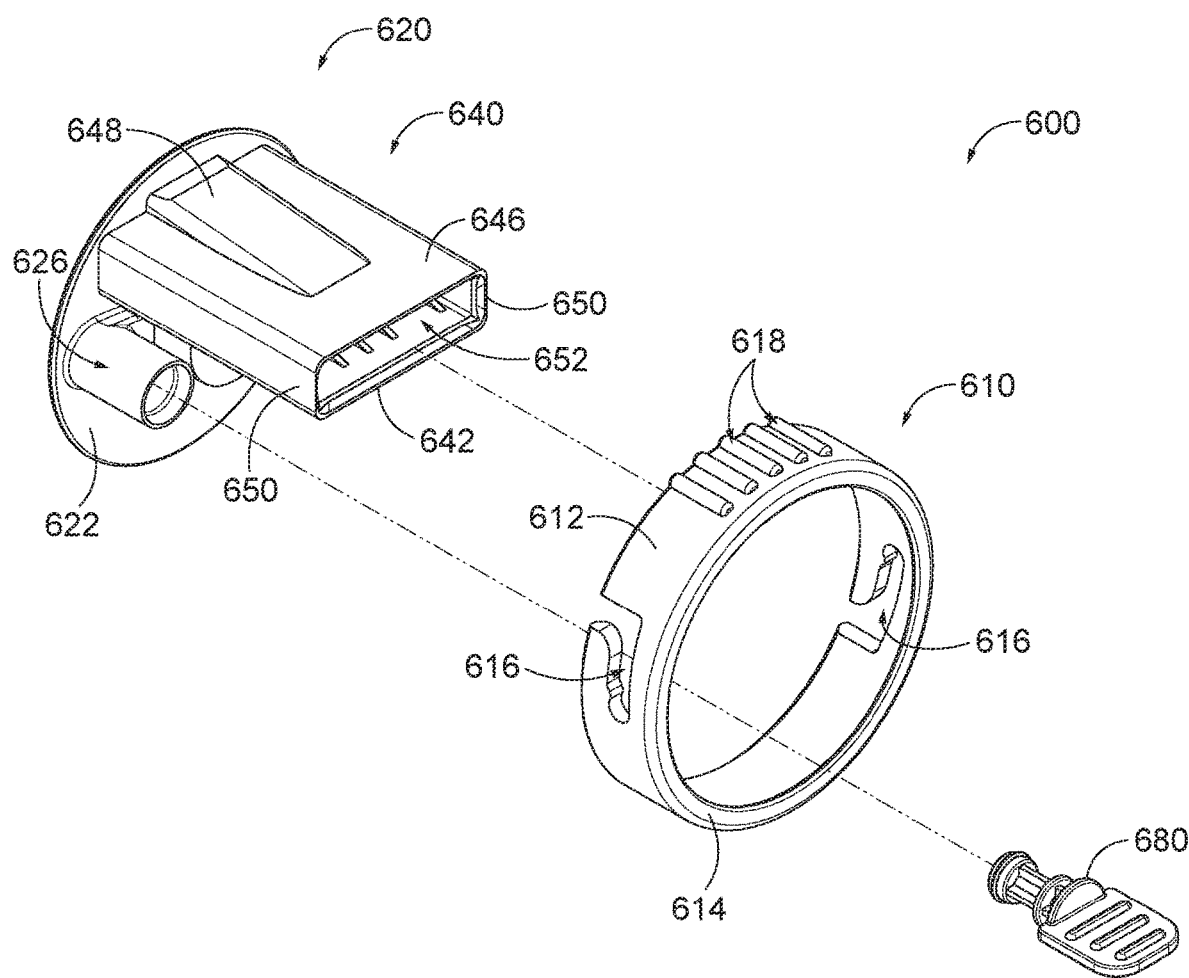
FIG. 17 depicts an exploded perspective view of the tissue sample holder assembly of FIG. 16.

FIGS. 16-19 show an exemplary alternative tissue sample holder assembly (600) that may be used with biopsy device (10) in lieu of tissue sample holder assembly (40) described above. As best seen in FIG. 17, tissue sample holder assembly (600) comprises a coupler (610), a rotatable member (620), and a plug (680). Coupler (610) comprises a generally ring-shaped body (612) with a sealing lip (614), a pair of bayonet connectors (616), and a plurality of grips (618). Sealing lip (614) is configured to engage at least a portion of rotatable member (620) to seal rotatable member (620) relative to coupler (610) and probe assembly (20). In addition, sealing lip (614) is configured to permit rotation of rotatable member (620) relative to coupler (610) and probe assembly (20). As will be described in greater detail below, this rotation permits cassette tray (510) to be moved relative to probe assembly (20) so that a single tissue sample can be collected within each sample chamber (523) of cassette tray (510).

Bayonet connectors (616) are configured to receive a pair of bayonet pins (not shown) of probe assembly (20) to selectively couple coupler (610) to probe assembly (20). Thus, bayonet connectors (616) and the bayonet pins of probe assembly (20) form a standard bayonet coupling assembly to selectively secure coupler (610) to probe assembly (20). In this configuration, ring-shaped body (612) is generally rotatable relative to probe assembly (20) to lock and unlock coupler (610) relative to probe assembly (20). To assist an operator with rotation of ring-shaped body (612), coupler (610) includes grips (618) to enhance grip of ring-shaped body (612) during locking and unlocking. Although the present example uses a bayonet coupling to secure coupler (610) to probe assembly (20), it should be understood that in other examples various alternative coupling features can be used as will be apparent to those of ordinary skill in the art in view of the teachings herein.

Rotatable member (620) is generally configured to receive cassette tray (510) and position cassette tray (510) relative to probe assembly (20) to thereby collect a tissue sample within each sample chamber (523) of cassette tray (510). Rotatable member (620) comprises a circular base (622), an access port (626) protruding proximally from base (622), and a manifold (640), also protruding from base (622). The circular shape of base (620) is generally configured for receipt within coupler (610) such that at least a portion of base (620) abuts sealing lip (614) of coupler (610).

Access port (626) defines a hollow cylindrical protrusion protruding proximally from base (622). As will be described in greater detail below, access port (626) is generally configured to receive plug (680) to seal access port (626) relative to the exterior of base (622). However, plug (680) is generally selectively removable to permit accessibility of access port (626). Access port (626) is generally sized to receive a marker deployment instrument or other medical instruments. As will be described in greater detail below, rotatable member (620) can be rotated to align access port (626) with the cutter of needle (22). When access port (626) is aligned with the cutter of needle (22), access port (626) can be used to gain access to the biopsy site through the cutter of needle (22). As will be understood, this feature may be used for marking purposes or other medical purposes.

Manifold (640) comprises a lower wall (642), an upper wall (646), and a pair of sidewalls (650) extending between the lower wall (642) and the upper wall (646). In some circumstances, manifold (640) can also be referred to as a cassette holder. Walls (642, 646, 650) together define a generally rectangular box that is configured to receive cassette tray (510). Walls (642, 646, 650) further define an inner chamber (652) that is large enough to accommodate cassette tray (510), while also providing fluid flow through manifold (640).

Upper wall (646) includes a raised connector (648) that is generally hollow such that a portion of inner chamber (652) is defined by raised connector (648). As will be described in greater detail below, raised connector (648) is generally configured to receive tissue samples axially relative to the longitudinal axis of rotatable member (620) and direct tissue samples downwardly into cassette tray (510). Although raised connector (648) is shown as a single discrete part that is integral with upper wall (646), it should be understood that in other examples raised connector (648) can be a separate part, formed of more than one part, or a combination of both.

Figure 18:
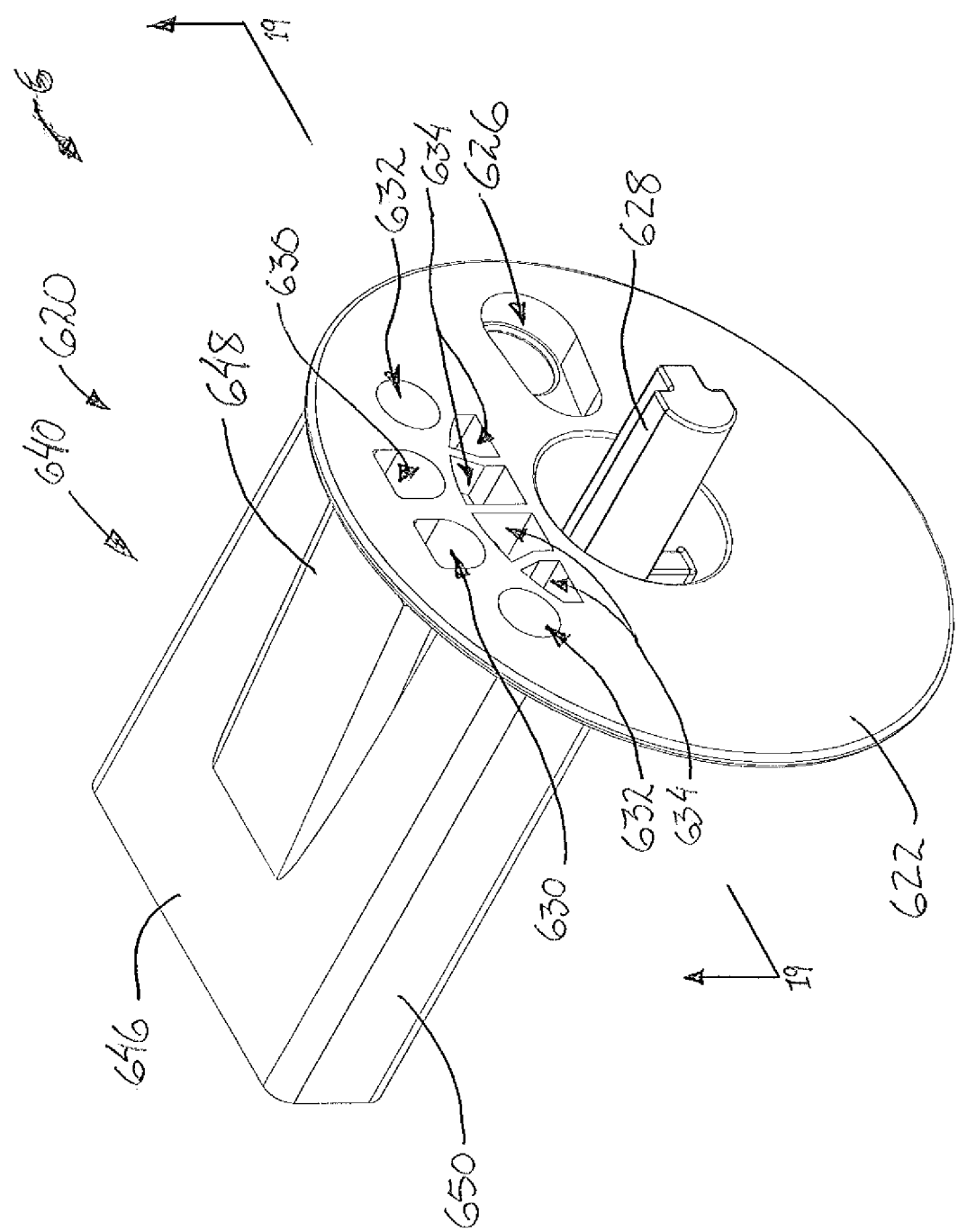
FIG. 18 depicts a perspective view of an exemplary rotatable member of the tissue sample holder assembly of FIG. 16.

As best seen in FIG. 18, inner chamber (652) communicates with probe assembly (20) via a plurality of openings (630, 632, 634) defined by and extending axially through circular base (622). In particular, circular base (622) defines four sample openings (630, 632) and four vacuum openings (634). Of the four sample openings (630, 632), circular base (622) defines two upper sample openings (630) and two lower sample openings (632). In this configuration, upper sample openings (630) communicate with the portion of inner chamber (652) that is defined by raised connector (648), while lower sample openings (632) are in communication with the portion of inner chamber (652) that is defined by walls (642, 646, 650). As described above, rotatable member (620) is generally rotatable to place a particular sample chamber (523) of cassette tray (510) into communication with the cutter of needle (22). However, since cassette tray (510) is generally of a flat configuration, upper sample openings (630) are positioned above lower sample openings (632) to accommodate both the rotation of rotatable member (620) and the flat configuration of cassette tray (510).

In contrast to sample openings (630, 632), vacuum openings (634) are generally aligned along a common axis. However, to accommodate rotation of rotatable member (620), the upper portion of each vacuum opening (632) is generally shaped to form an arc or semi-circle relative to the upper portion of each adjacent vacuum opening (632). As will be described in greater detail below, each vacuum opening (632) is generally associated with a corresponding sample opening (630, 632). As a result, only a single vacuum opening (632) is in communication with a vacuum source when the particular corresponding sample opening (630, 632) is in communication with the cutter of needle (22). As will also be described in greater detail below, this configuration generally promotes the flow of vacuum into a given vacuum opening (634), into inner chamber (652) (and through cassette tray (510)) and out of a corresponding sample opening (630, 632).

Figure 19:
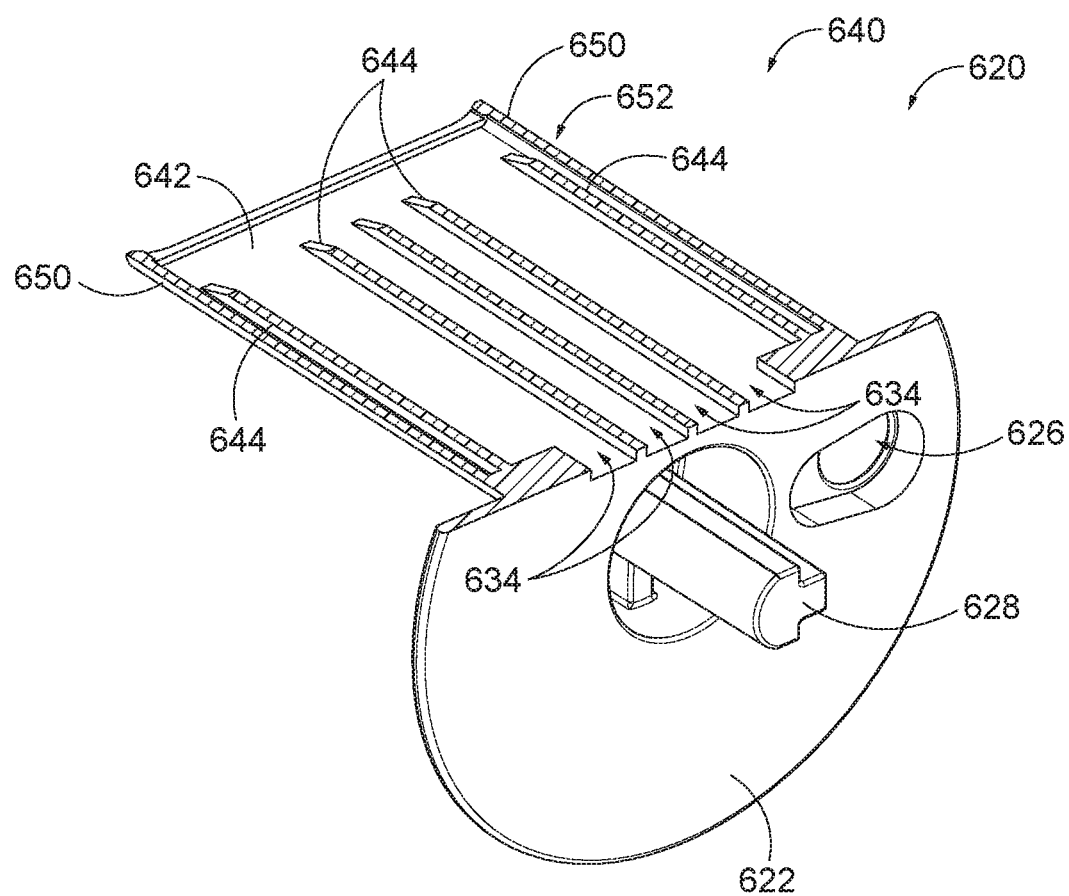

As best seen in FIG. 19, within inner chamber (652), lower wall (642) includes a plurality of vacuum walls (644) that define a plurality of vacuum chambers (645). Each vacuum wall (644) extends upwardly from lower wall (642) partially into inner chamber (652). This upward extension both defines vacuum chambers (645) and provides support for cassette tray (510) when cassette tray (510) is inserted into manifold (640). As will be described in greater detail below, each vacuum chamber (645) is in communication with a corresponding vacuum opening (634) to communicate vacuum from probe assembly (20) and into cassette tray (510).

Rotatable member (620) further comprises a keyed shaft (628) extending distally from circular base (622). Keyed shaft (628) is generally configured to engage at least a portion of probe assembly (20) and/or holster assembly (30) to rotate rotatable member (620) relative to probe assembly (20). Keyed shaft (628) is substantially similar to a corresponding feature of tissue sample holder assembly (40) such that tissue sample holder assembly (600) remains compatible with probe assembly (20) without modification. However, it should be understood that in some circumstances probe assembly (20) and/or holster assembly (30) may be operated using different algorithms specifically for tissue sample holder assembly (600) to accommodate different rotational requirements associated with rotatable member (620).

Figure 20B:
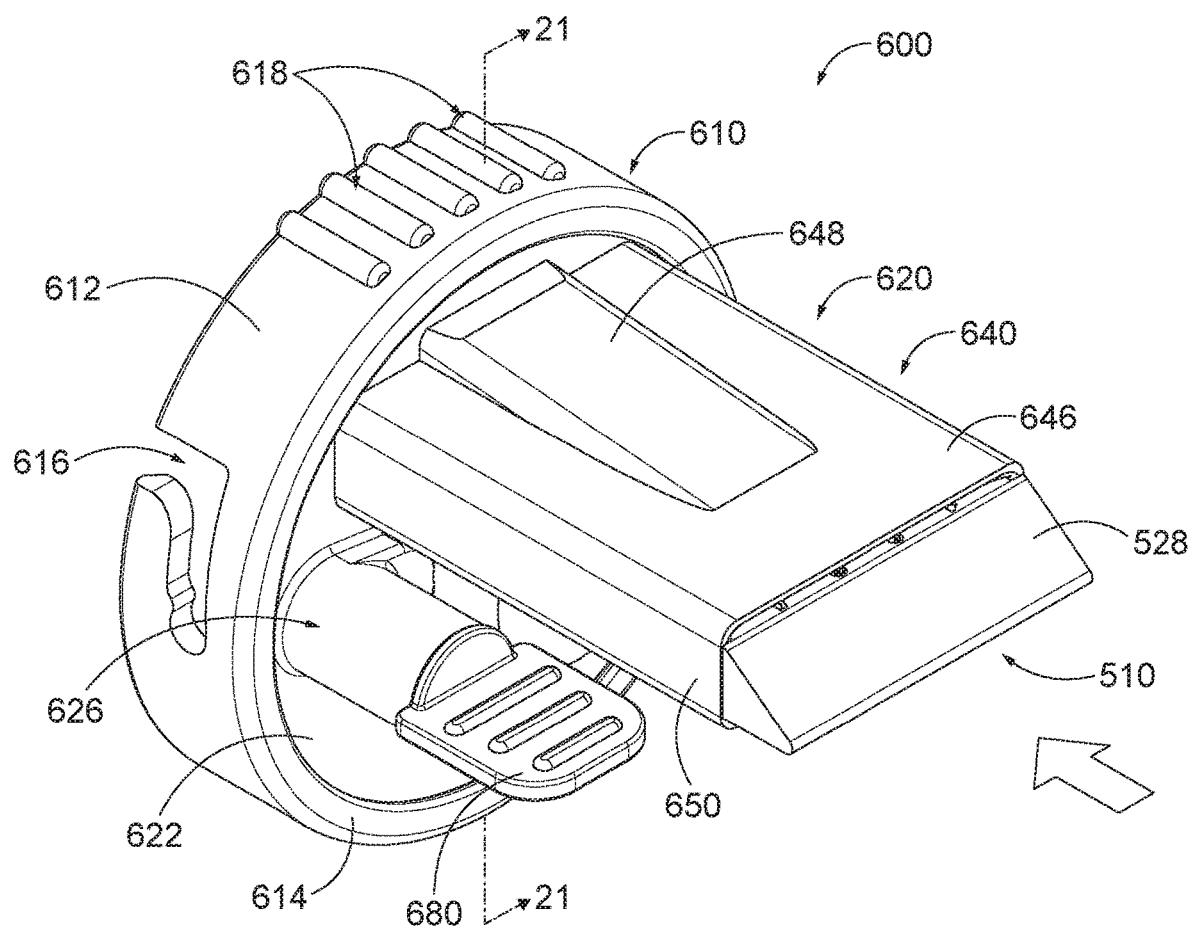
FIG. 20B depicts another perspective view of the tissue sample holder assembly of FIG. 16, with the cassette tray of FIG. 11 inserted into the tissue sample holder assembly.

FIGS. 20A-25 show an exemplary use of tissue sample holder assembly (600) to collect tissue samples within cassette tray (510). As best seen in FIGS. 20A and 20B, cassette tray (510) may be initially inserted into manifold (640) of rotatable member (620). Although not shown, it should be understood that at this stage tissue sample holder assembly (600) is generally already coupled to probe assembly (20) via coupler (610) in lieu of tissue sample holder assembly (40). However, it should be understood that in other uses, cassette tray may be first inserted into manifold (640) and then tissue sample holder assembly (600) may be attached to probe assembly (20). Regardless of whether tissue sample holder assembly (600) is attached to probe assembly (20), cassette tray (510) may be inserted into manifold (640) by inserting distal wall (512) of cassette tray (510) into the proximal end of manifold (640). The proximal end of manifold (640) is open to inner chamber (652). Accordingly, cassette tray (510) can be simply inserted into manifold (640).

Figure 21:
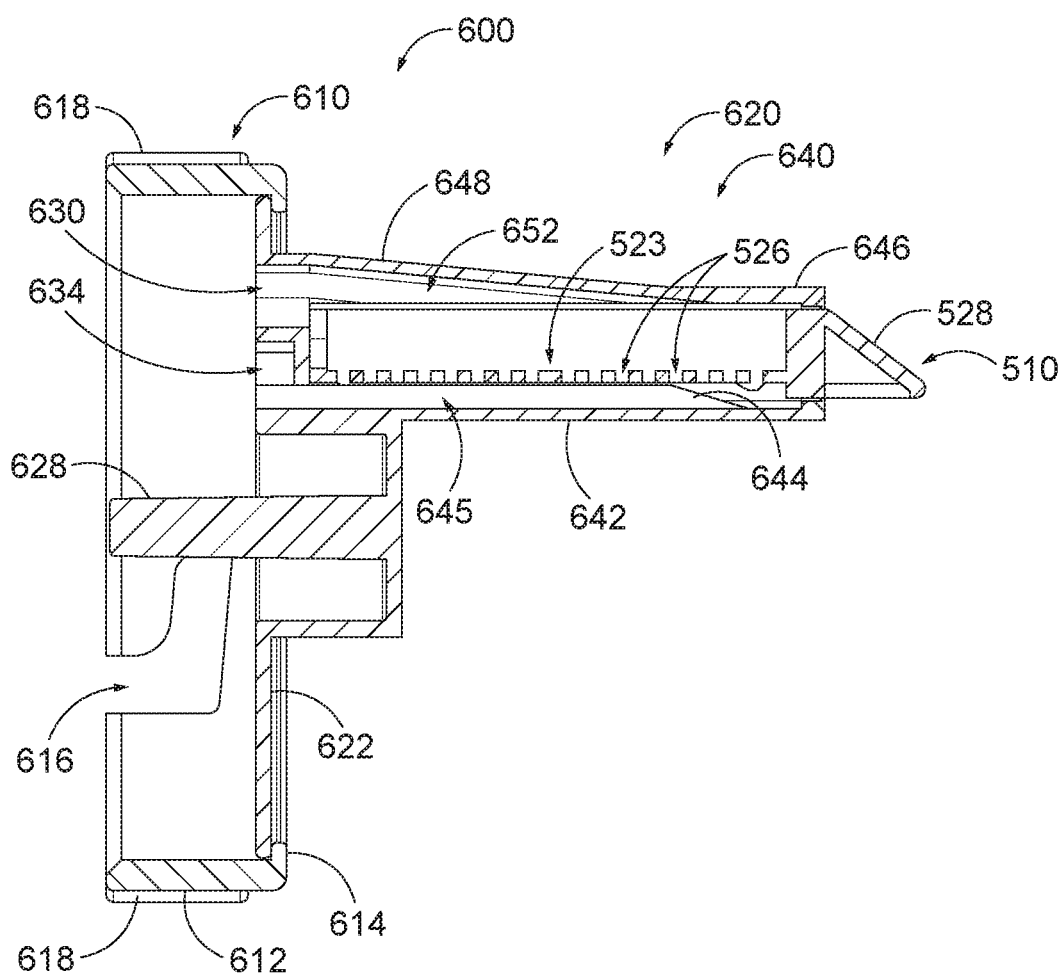
FIG. 21 depicts a side cross-sectional view of the tissue sample holder assembly of FIG. 16, with the cassette tray of FIG. 11 inserted into the tissue sample holder assembly.
Figure 22A:
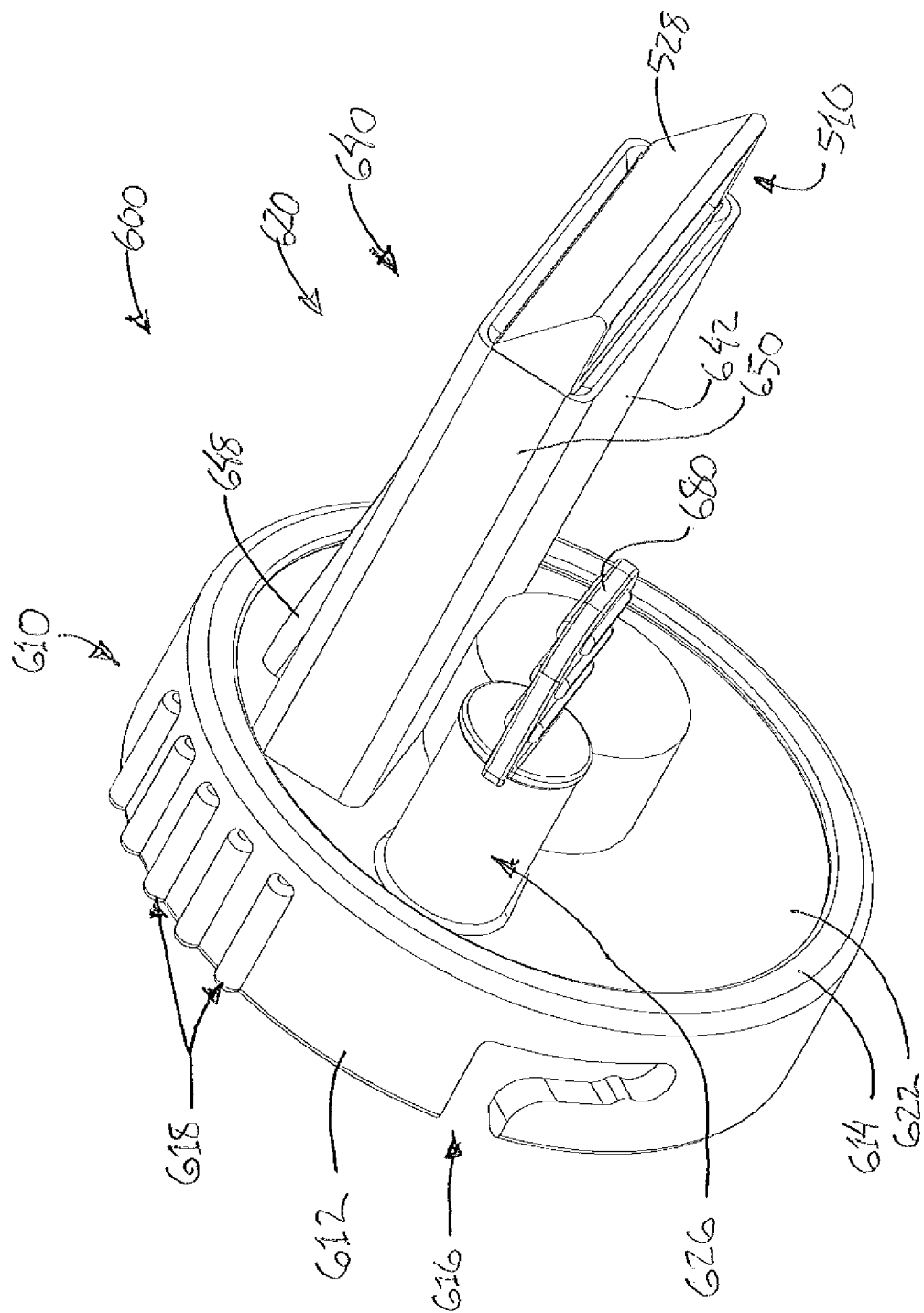
FIG. 22A depicts still another perspective view of the tissue sample holder assembly of FIG. 16, with the rotatable member of FIG. 18 in a first sample receiving position.
Figure 22B:
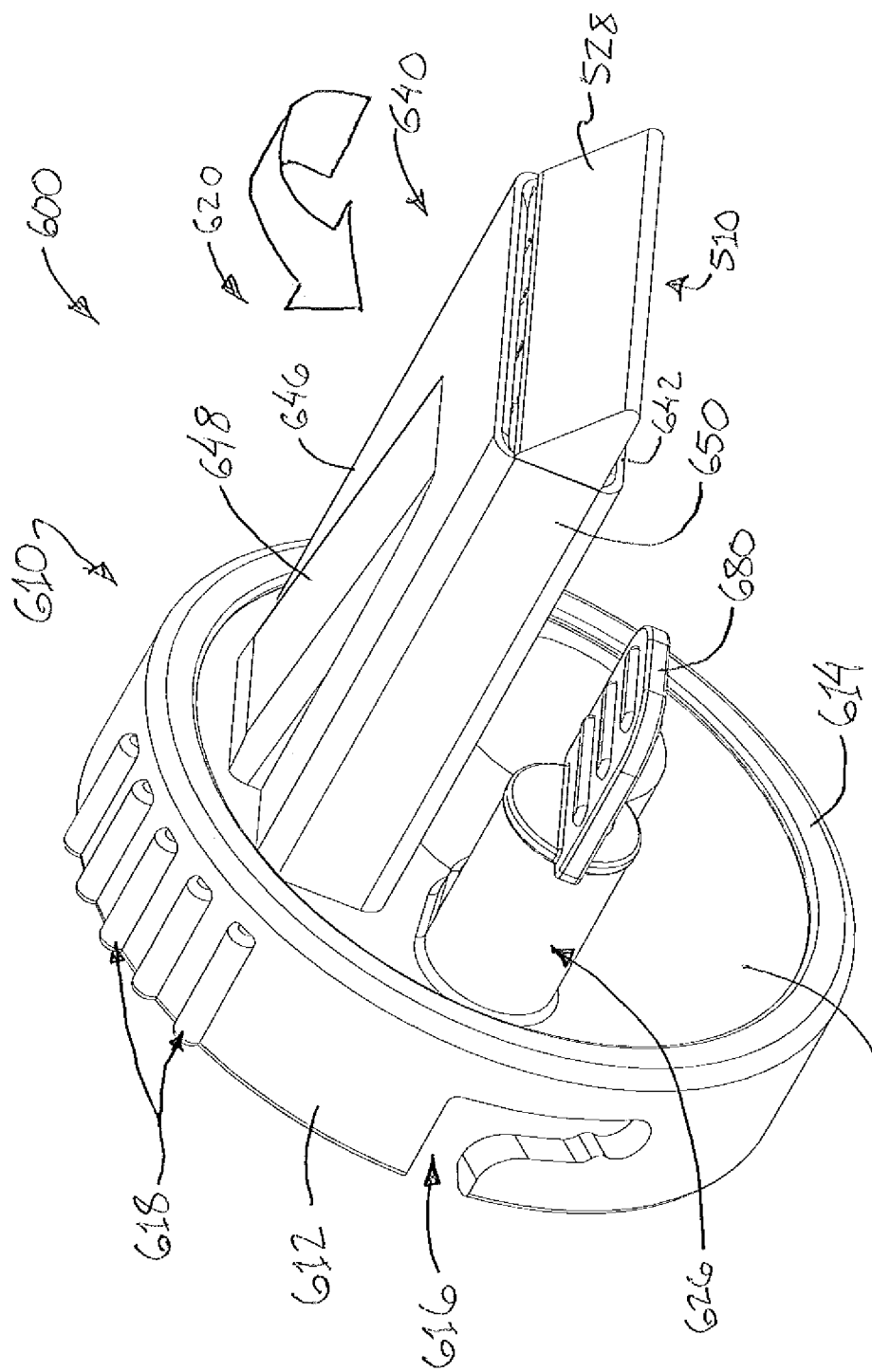
FIG. 22B depicts yet another perspective view of the tissue sample holder assembly of FIG. 16, with the rotatable member of FIG. 18 in a second sample receiving position.
Figure 22C:
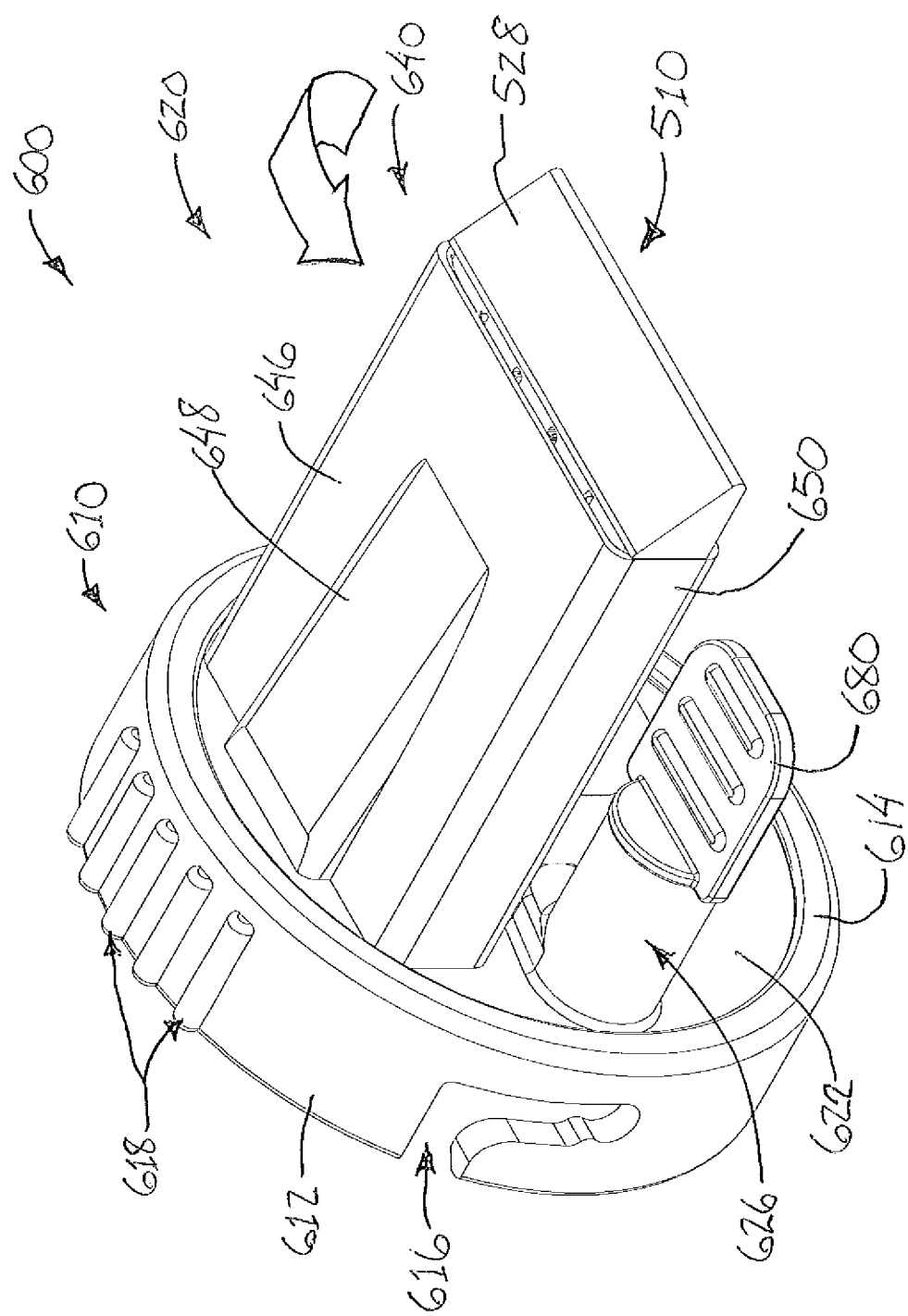
FIG. 22C depicts yet another perspective view of the tissue sample holder assembly of FIG. 16, with the rotatable member of FIG. 18 in a third sample receiving position.

Once cassette tray (510) is inserted into manifold (640), labeling portion (528) of cassette tray (510) engages the proximal ends of lower wall (642), upper wall (646), and sidewalls (650). As best seen in FIG. 21, this engagement provides sealing of cassette tray (510) relative to the exterior of manifold (640). Although not shown, it should be understood that in some examples either manifold (640) or cassette tray (510) can include additional sealing features such as rubber gaskets to aid in the sealing of cassette tray (510) relative to the exterior of manifold (640). In other examples, sealing is provided by a compression fit between walls (642, 646, 650) of manifold (640) and labeling portion (528) of cassette tray (510).

With cassette tray (510) disposed within manifold (640) as shown in FIG. 21, vacuum enters manifold (640) through a given vacuum opening (634) that is in communication with a corresponding vacuum port of probe assembly (20). Next, vacuum travels through the corresponding vacuum chamber (645) and upwardly through vents (526) of cassette tray (510). Vacuum then travels through a corresponding sample chamber (523) of cassette tray (510) and out of manifold (640) either through an upper sample opening (630) or lower sample opening (632), depending on which sample opening (630, 632) is positioned into communication with the cutter of needle (22). Vacuum is then used to pull a tissue sample through the cutter of needle (22) and into the corresponding sample chamber (526) of cassette tray (510).

FIGS. 23A-23D show an exemplary progression of tissue sample holder assembly (600) to fill each sample chamber (523) of cassette tray (510) with a single tissue sample. As can be seen, rotatable member (620) is initially rotated so that a selected lower sample opening (632) and a selected vacuum opening (634) is positioned at a twelve o'clock position. Although not shown, it should be understood that probe assembly (20) defines two ports that are also at the twelve o'clock position. Each of the two ports corresponds to either communication with the cutter of needle (22) or a vacuum source. Accordingly, when the selected lower sample opening (632) is in the twelve o'clock position, the selected lower sample opening (632) is in communication with the cutter of needle (22). Correspondingly, when the selected vacuum opening (634) is in the twelve o'clock position, the selected vacuum opening (634) is in communication with a vacuum source associated with probe assembly (20).

Figure 23A:
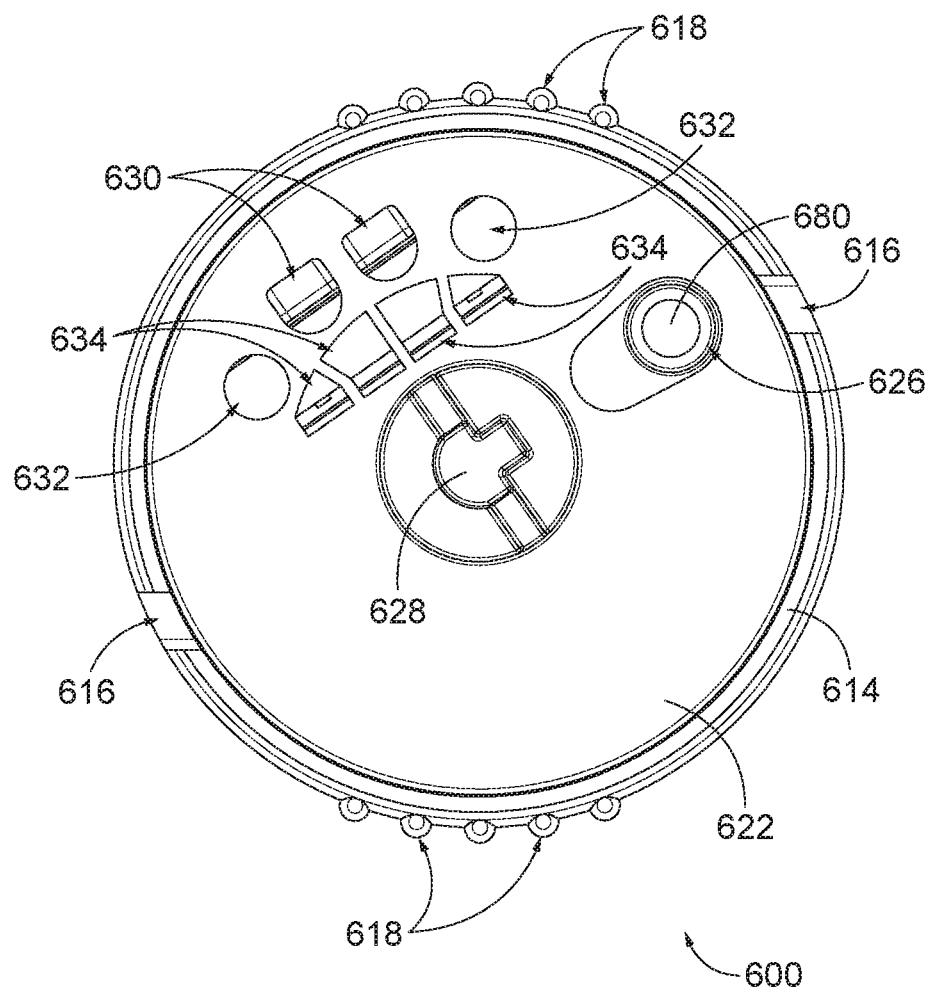
FIG. 23A depicts a front elevational view of the tissue sample holder assembly of FIG. 16, with the rotatable member of FIG. 18 in the first sample receiving position.

Once the selected lower sample opening (632) and the selected vacuum opening (634) are positioned as shown in FIG. 23A, vacuum will enter the selected vacuum opening (634). Vacuum then travels through a corresponding vacuum chamber (645) and into a corresponding sample chamber (523) of cassette tray (510) via vents (526) of floor (524). Vacuum then travels from the corresponding sample chamber (523) and through the selected lower sample opening (632). Vacuum can then travel through cutter of needle (22) to pull a tissue sample severed by the cutter through the cutter and into sample chamber (523) of cassette tray (510).

Figure 23B:
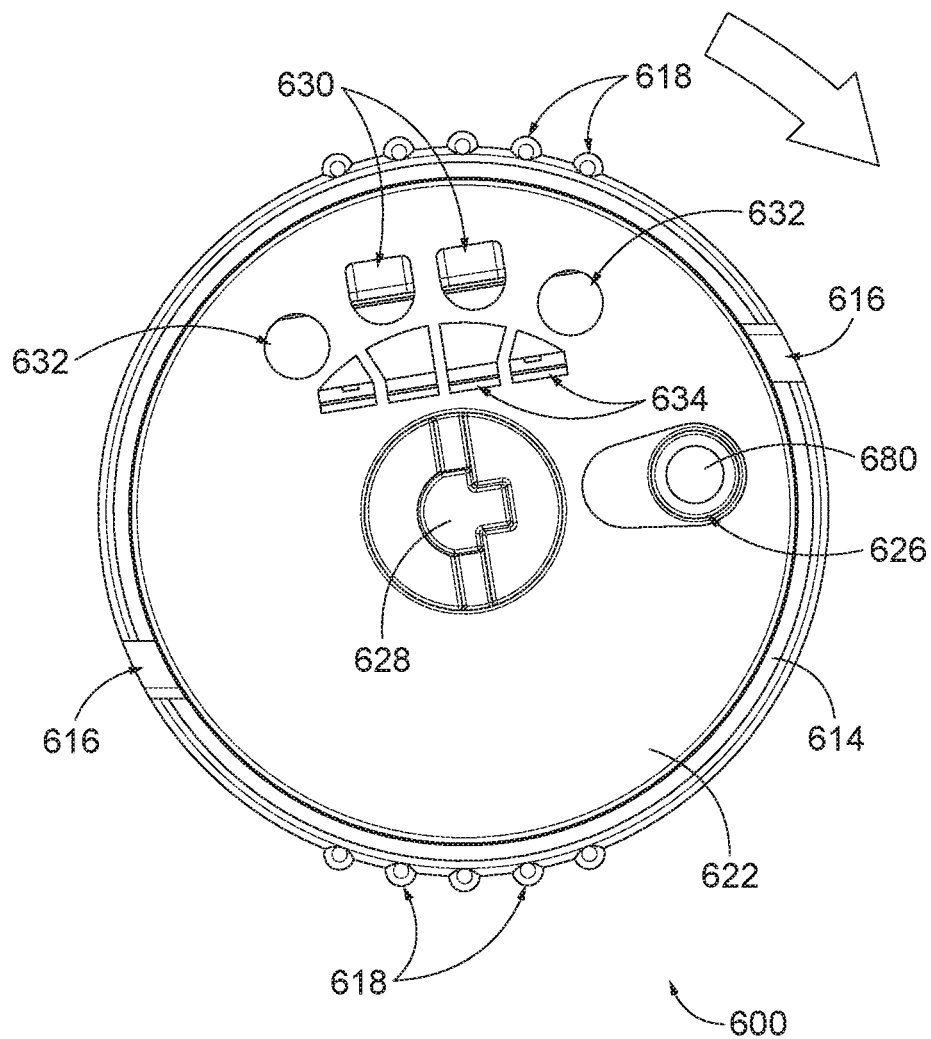
FIG. 23B depicts another front elevational view of the tissue sample holder assembly of FIG. 16, with the rotatable member of FIG. 18 in the second sample receiving position.

Once a sample is received within sample chamber (523) of cassette tray (510), rotatable member (620) is rotated to the position shown in FIG. 23B. This rotation indexes the next successive sample opening (630, 632) and vacuum opening (634) into the twelve o'clock position described above. In the present use, this rotation results in a selected upper sample opening (630) and another selected vacuum opening (634) being in communication with corresponding features of probe assembly (20) as similarly described above. In this position, another tissue sample may be collected in the sample chamber (523) of cassette tray (510) corresponding to the selected upper sample opening (630).

It should be understood that when an upper sample opening (630) is indexed to the twelve o'clock position, a tissue sample received therein may not proceed directly into sample chamber (523) of cassette tray (510). Instead, the tissue sample first enters the area of inner chamber (652) defined by raised connector (648). The interior of raised connector (648) may then direct the tissue sample downwardly into the corresponding sample chamber (523) of cassette tray (510). Thus, it should be understood that in some examples the interior of raised connector (648) can act as a sample deflector, director, or channeler to direct a tissue sample into cassette tray (510) after the tissue sample is received through either upper sample opening (630). Accordingly, although raised connector (648) is shown as having a specific angle and/or geometry, it should be understood that the particular configuration of raised connector (648) may be adjusted based on a number of considerations such as the positioning of each upper sample opening (630) relative to cassette tray (510), the velocity of tissue sample transport, the size of the collected tissue samples, the gage size of needle (22), and/or etc.

Next, rotatable member (620) is again rotated to the position shown in FIG. 23C. This rotation moves another selected upper sample opening (630) and another vacuum opening (634) into the twelve o'clock position. Once at the twelve o'clock position, the next selected upper sample opening (630) and the next selected vacuum opening (634) can be used to collect a tissue sample into the sample chamber (523) of cassette tray (510) corresponding to the next selected upper sample opening (630).

Figure 23D:
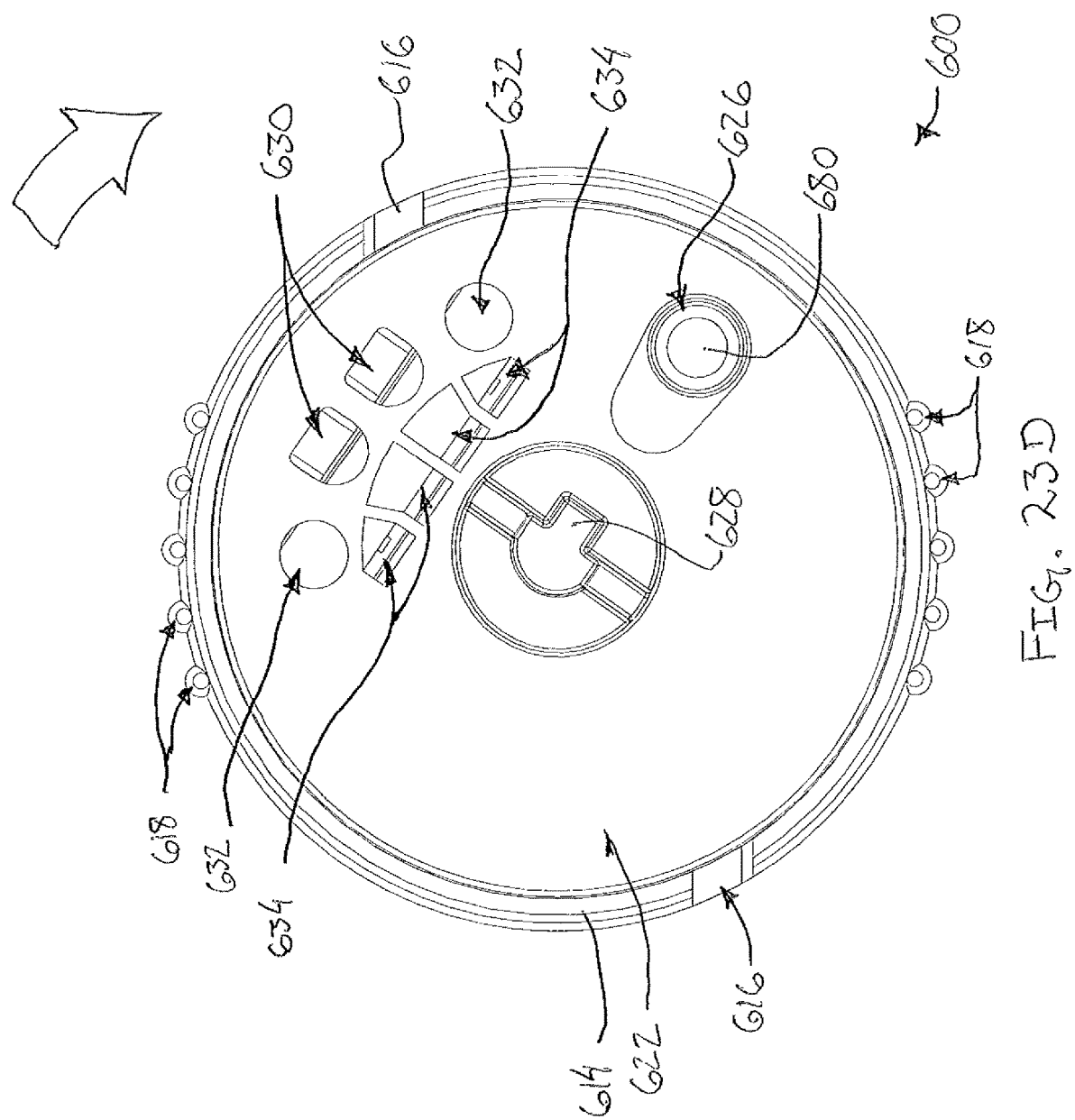
FIG. 23D depicts a front elevational view of the tissue sample holder assembly of FIG. 16, with the rotatable member of FIG. 18 in the fourth sample receiving position.
Figure 25:
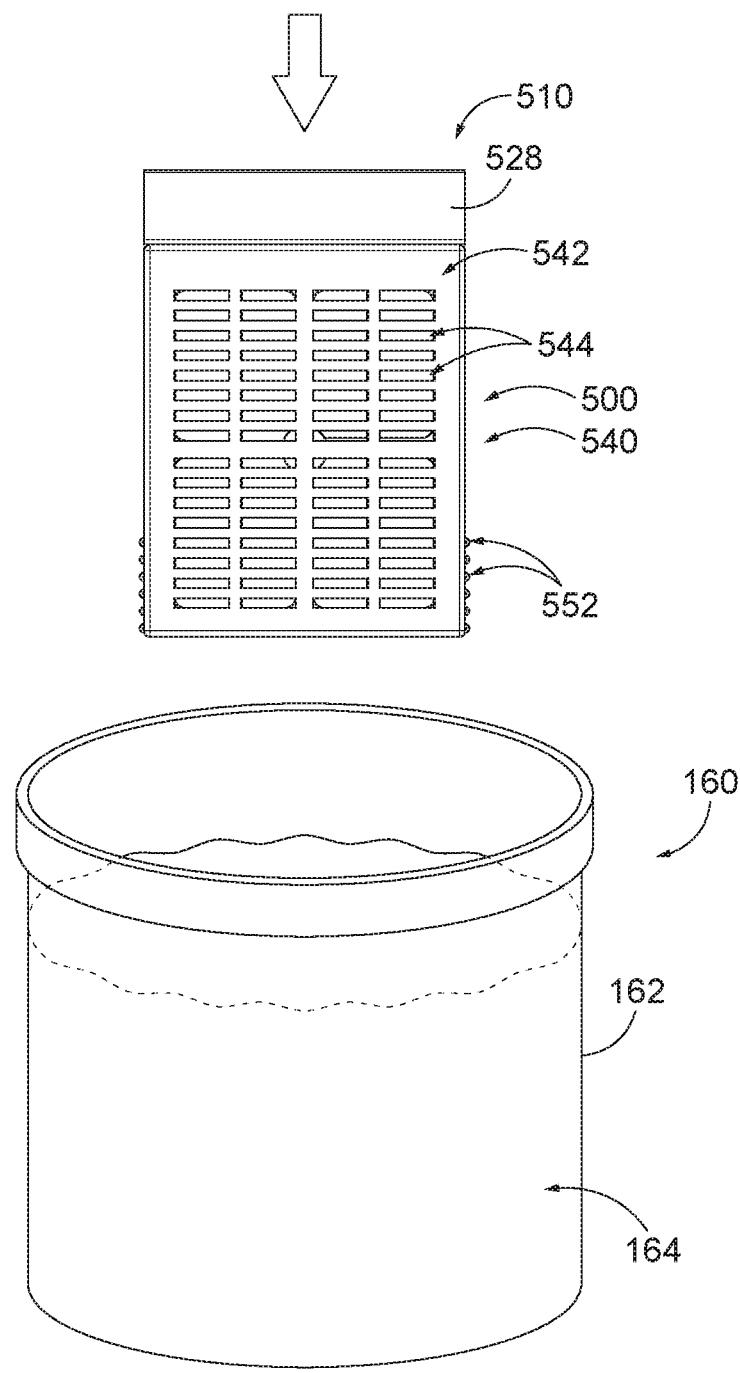
FIG. 25 depicts a perspective view of the cassette assembly of FIG. 8 being inserted into the jar of FIG. 5.

Finally, rotatable member (620) is next rotated to the position shown in FIG. 23D. This rotation moves another selected lower sample opening (632) and another vacuum opening (634) into the twelve o'clock position. Once at the twelve o'clock position, the next selected lower sample opening (632) and the next selected vacuum opening (634) can be used to collect a tissue sample into the sample chamber (523) of cassette tray (510) corresponding to the next selected lower sample opening (632).

Although tissue sample holder assembly (600) is described above as being used to collect a tissue sample in each sample chamber (523) of cassette tray (510), it should be understood that in some uses it may be desirable to only collect samples into one or more specific sample chambers (523) of cassette tray (510). Accordingly, in some uses rotatable member (620) may be rotated to skip some sample openings (630, 632) and proceed directly to indexing one or more specific sample openings (630, 632) with the twelve o'clock position described above.

Once sample chambers (523) of cassette tray (510) are filled with a tissue sample as desired by an operator, an operator may next desire to perform certain analysis on the collected tissue samples. To perform analysis on the collected tissue samples, an operator first removes cassette tray (510) from manifold (640) of rotatable member (620). At this stage, cassette tray (510) may be manipulated for a visual inspection of each tissue sample. In addition, cassette tray (510) may be placed in a procedure room x-ray unit to perform a preliminary analysis of the tissue samples. If an operator is not satisfied with the results at this stage, undesirable tissue samples may be discarded and the same cassette tray (510) may be inserted back into manifold (640) of rotatable member (620) for collection of addition tissue samples. Alternatively, an entirely new cassette tray (510) may be placed into manifold (640) of rotatable member (620) for collection of additional tissue samples.

Once tissue sample are collected to the satisfaction of an operator, the operator may desire to transport tissue samples to a pathology laboratory. At this stage, an operator may mark or place a label onto labeling portion (528) to ensure chain of custody through the workflow. Alternatively, in some uses, labeling portion (528) may already be labeled at this stage. For instance, in some uses labeling portion (528) may be labeled at the beginning of the biopsy procedure before collecting any tissue samples. Alternatively, in some uses labeling portion (528) may be prelabeled with a bar code, QR code, or another computer readable medium. Where such computer readable mediums are used, labeling portion (528) may be scanned as various stages to associate the computer readable medium with the patient. This may include multiple scans throughout the procedure such as before the biopsy procedure, after collection of tissue samples, after procedure room x-ray, and/or etc.

Once chain of custody has been established using labeling portion (528), cassette tray (510) may be inserted into cover (540) as described above and as shown in FIG. 24. The combination of cassette tray (510) and cover (540) may then be inserted into jar (160) described above. As described above, jar (160) may be filled with a fluid such as formalin to preserve the collected tissue samples during transport and/or storage. Although cassette tray (510) is described herein as being used with the same jar (160) described above, it should be understood that other alternative jars or containers may be used for transport and/or storage of cassette tray (510). For instance, in some examples jar (160) may be replaced with a container of a variety of shapes and sizes. In other examples, cover (540) itself may be used to transport cassette tray (510). Of course, in such examples structures of cover (540) such as vents (544) and/or open spaces (549) can be closed so that cover (540) can hold fluids such as formalin.

After the combination of cassette tray (510) and cover (540) is inserted into jar (160), jar (160) may be transported to the pathology laboratory as shown in FIG. 7 and described above. The collected tissue samples may then be processed in accordance with the workflow (300) shown in FIG. 7. However, since cassette assembly (500) can be used in lieu of tissue processing cassette (200), it should be understood that certain steps may be omitted such as straining the collected samples as represented by box (350) and placing the collected samples into a tissue processing cassette (200) as represented by box (370). In addition, it should be understood that at any one or more of the steps depicted in FIG. 7, an operator may interact with labeling portion (528) to confirm chain of custody of the collected tissue samples. By way of example only, this may include scanning computer readable mediums associated with labeling portion (528), confirming information on labeling portion (528) with information on jar (160) or other components, or confirming information on labeling portion (528) with patient files.

IV. Exemplary Alternative Cassette Tray Configurations

In some instances, it may be desirable to use a cassette tray similar to cassette tray (510) described above with certain structural modifications to facilitate use of the cassette tray in different contexts or to alter the performance of the cassette tray. Although the foregoing describes multiple alternative embodiments of a cassette tray similar to cassette tray (510) described above, it should be understood that any one or more of the features described herein may be readily combined with other features in a single embodiment. Similarly, one or more features may be omitted as desired. Of course, various alternative configurations may be used as will be apparent to those of ordinary skill in the art in view of the teachings herein.

Figure 26:
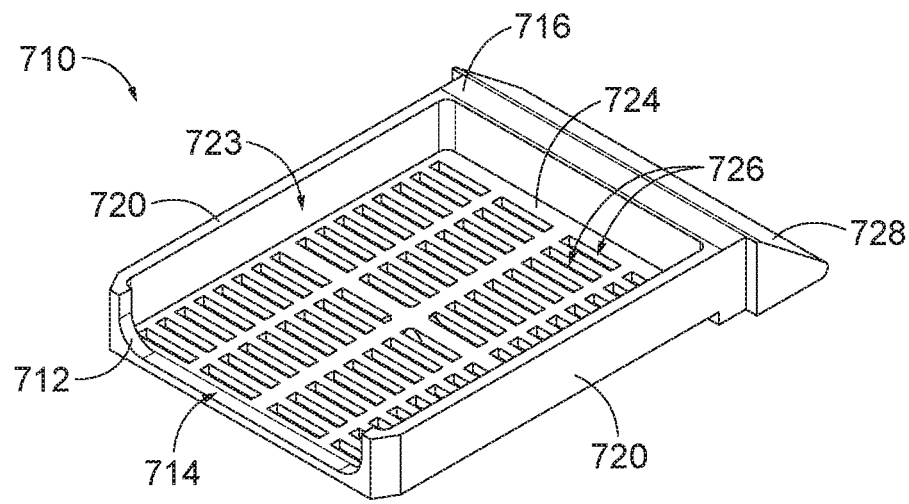
FIG. 26 depicts a perspective view of an exemplary alternative cassette tray for use with the cover of FIG. 13 in lieu of the cassette tray of FIG. 11.

FIG. 26 shows an exemplary alternative cassette tray (710) that may be readily used with cover (540) and/or tissue sample holder assembly (600) described above in lieu of cassette tray (510). It should be understood that cassette tray (710) is substantially similar to cassette tray (510) described above except as otherwise specifically noted herein. For instance, cassette tray (710) comprises a distal wall (712), a proximal wall (716), a pair of sidewalls (720) extending between distal wall (712) and proximal wall (716), and a floor (724) positioned below walls (712, 716, 720). However, unlike cassette tray (510), distal wall (712) defines only a single opening (714). Like with openings (514) described above, opening (714) is generally configured to receive a tissue sample. Like proximal wall (516) described above, proximal wall (716), is solid. However, unlike proximal wall (516) described above, proximal wall (716) of the present example omits structural features similar to indicia (518) described above.

Like with walls (512, 516, 520) described above, walls (712, 716, 720) are interconnected to form the outer perimeter of cassette tray (710). However, unlike cassette tray (510) described above, cassette tray (710) of the present example omits structures similar to inner divider walls (522) described above. Instead, walls (712, 716, 720) define a single discrete sample chamber (723) that is configured to hold tissue samples in a bulk configuration.

Like floor (524) described above, floor (724) of the present example is positioned below walls (712, 716, 720). Floor (724) includes a plurality of vents (726). Vents (726) are generally configured to promote the flow of fluid through floor (724), yet maintain tissue samples within each sample chamber (723). To facilitate this configuration, vents (726) have a narrow rectangular form. In other examples, vents (726) can be configured with a variety of alternative shapes such as round, oval-shaped, square, and/or etc. Although vents (726) in the present example are arranged to uniformly occupy the entire surface of floor (724), it should be understood that in other examples vents (726) can be arranged in a variety of other ways.

Floor (724) is opposite to an open space above sample chamber (723). Thus, the upper portion of cassette tray (710) is generally open. Because of this, tissue samples may be deposited into each sample chamber (723) through opening (714) in distal wall (712) or through the open upper portion of cassette tray (710).

As with cassette tray (510) described above, cassette tray (710) further includes a labeling portion (728) protruding proximally from proximal wall (716). Like with labeling portion (528) described above, labeling portion (728) generally defines a triangular or wedge shape that provides a flat smooth surface for printing or otherwise adhering a label to the surface of labeling portion (728). As similarly described above with respect to labeling portion (528), labeling portion (728) is generally configured to provide readily accessible patient information to an operator to aid with tracking of tissue samples as they progress through the biopsy and sample analysis procedure.

Although not shown, it should be understood that cassette tray (710) further comprises a plurality of detents (not shown) disposed on the underside of floor (724). As similarly described above with respect to detents (530, 532), each pair of detents is positioned to provide temporary or selective locking of cassette tray (710) at various positions relative to cover (540) when cassette tray (710) is inserted into cover (540).

In an exemplary use, cassette tray (710) is used similarly to cassette tray (510) described above. For instance, cassette tray (710) can be similarly inserted into both manifold (640) of tissue sample holder assembly (600) and cover (540). However, unlike cassette tray (510), cassette tray (710) receives tissue samples indiscriminately into sample chamber (723). Thus, tissue samples are permitted to comingle once received within sample chamber (723). Although this does not prevent cassette tray (710) from being used with tissue sample holder assembly (600), this configuration may be beneficial in the context of a biopsy device that is generally configured to collect tissue samples in a bulk configuration. In such contexts, tissue samples may be received directly into cassette tray (710). Alternatively, tissue samples may first be received in a single bulk sample collection cup and then later placed in cassette tray (710).

Figure 27:
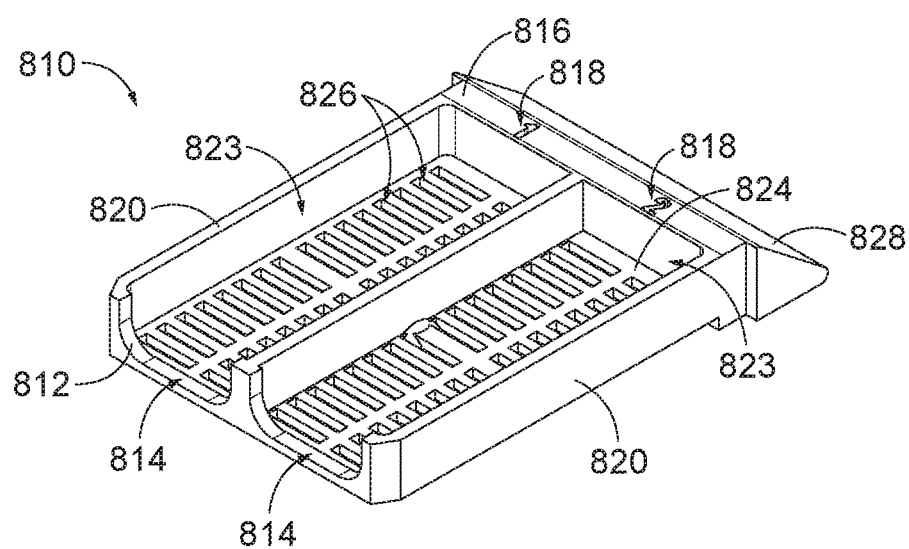
FIG. 27 depicts a perspective view of another exemplary alternative cassette tray for use with the cover of FIG. 13 in lieu of the cassette tray of FIG. 11.

FIG. 27 shows another exemplary alternative cassette tray (810) that may be readily used with cover (540) and/or tissue sample holder assembly (600) described above in lieu of cassette tray (510). It should be understood that cassette tray (810) is substantially similar to cassette tray (510) described above except as otherwise specifically noted herein. For instance, cassette tray (810) comprises a distal wall (812), a proximal wall (816), a pair of sidewalls (820) extending between distal wall (812) and proximal wall (816), and a floor (824) positioned below walls (812, 816, 820). However, unlike cassette tray (510), distal wall (812) defines only two single opening (814). Like with openings (514) described above, each opening (814) is generally configured to receive a tissue sample. Like proximal wall (516) described above, proximal wall (816), is solid. Also like proximal wall (516) described above, proximal wall (816) of the present example includes indicia (818) similar to indicia (518) described above.

Like with walls (512, 516, 520) described above, walls (812, 816, 820) are interconnected to form the outer perimeter of cassette tray (810). However, unlike cassette tray (510) described above, cassette tray (810) of the present example only includes a single inner divider wall (822) instead of a plurality of structures similar to inner divider walls (522) described above. Accordingly, walls (812, 816, 820, 822) define a two sample chambers (823) that are configured to hold tissue samples in one or more tissue samples.

Like floor (524) described above, floor (824) of the present example is positioned below walls (812, 816, 820). Floor (824) includes a plurality of vents (826). Vents (826) are generally configured to promote the flow of fluid through floor (824), yet maintain tissue samples within each sample chamber (823). To facilitate this configuration, vents (826) have a narrow rectangular form. In other examples, vents (826) can be configured with a variety of alternative shapes such as round, oval-shaped, square, and/or etc. Although vents (826) in the present example are arranged to uniformly occupy the entire surface of floor (824), it should be understood that in other examples vents (826) can be arranged in a variety of other ways.

Floor (824) is opposite to an open space above sample chambers (823). Thus, the upper portion of cassette tray (810) is generally open. Because of this, tissue samples may be deposited into each sample chamber (823) through openings (814) in distal wall (812) or through the open upper portion of cassette tray (810).

As with cassette tray (510) described above, cassette tray (810) further includes a labeling portion (828) protruding proximally from proximal wall (816). Like with labeling portion (528) described above, labeling portion (828) generally defines a triangular or wedge shape that provides a flat smooth surface for printing or otherwise adhering a label to the surface of labeling portion (828). As similarly described above with respect to labeling portion (528), labeling portion (828) is generally configured to provide readily accessible patient information to an operator to aid with tracking of tissue samples as they progress through the biopsy and sample analysis procedure.

Although not shown, it should be understood that cassette tray (810) further comprises a plurality of detents (not shown) disposed on the underside of floor (824). As similarly described above with respect to detents (530, 532), each pair of detents is positioned to provide temporary or selective locking of cassette tray (810) at various positions relative to cover (540) when cassette tray (810) is inserted into cover (540).

In an exemplary use, cassette tray (810) is used similarly to cassette tray (510) described above. For instance, cassette tray (810) can be similarly inserted into both manifold (640) of tissue sample holder assembly (600) and cover (540). However, unlike cassette tray (510), cassette tray (810) receives one or more tissue samples into each sample chamber (823) of the two sample chambers (823). Thus, some tissue samples are permitted to comingle once received within a particular sample chamber (823). In some examples, tissue sample holder assembly (600) is configured as described above with four tissue receiving positions. However, in other examples tissue sample holder assembly (600) can be modified to include only two tissue receiving positions (e.g., only two total sample openings (630, 632)). Although this does not prevent cassette tray (810) from being used with tissue sample holder assembly (600), this configuration may be beneficial in the context of a biopsy device that is generally configured to collect tissue samples in a bulk configuration. In such contexts, tissue samples may be received directly into cassette tray (810). Alternatively, tissue samples may first be received in a single bulk sample collection cup and then later placed in cassette tray (810).

Figure 28:
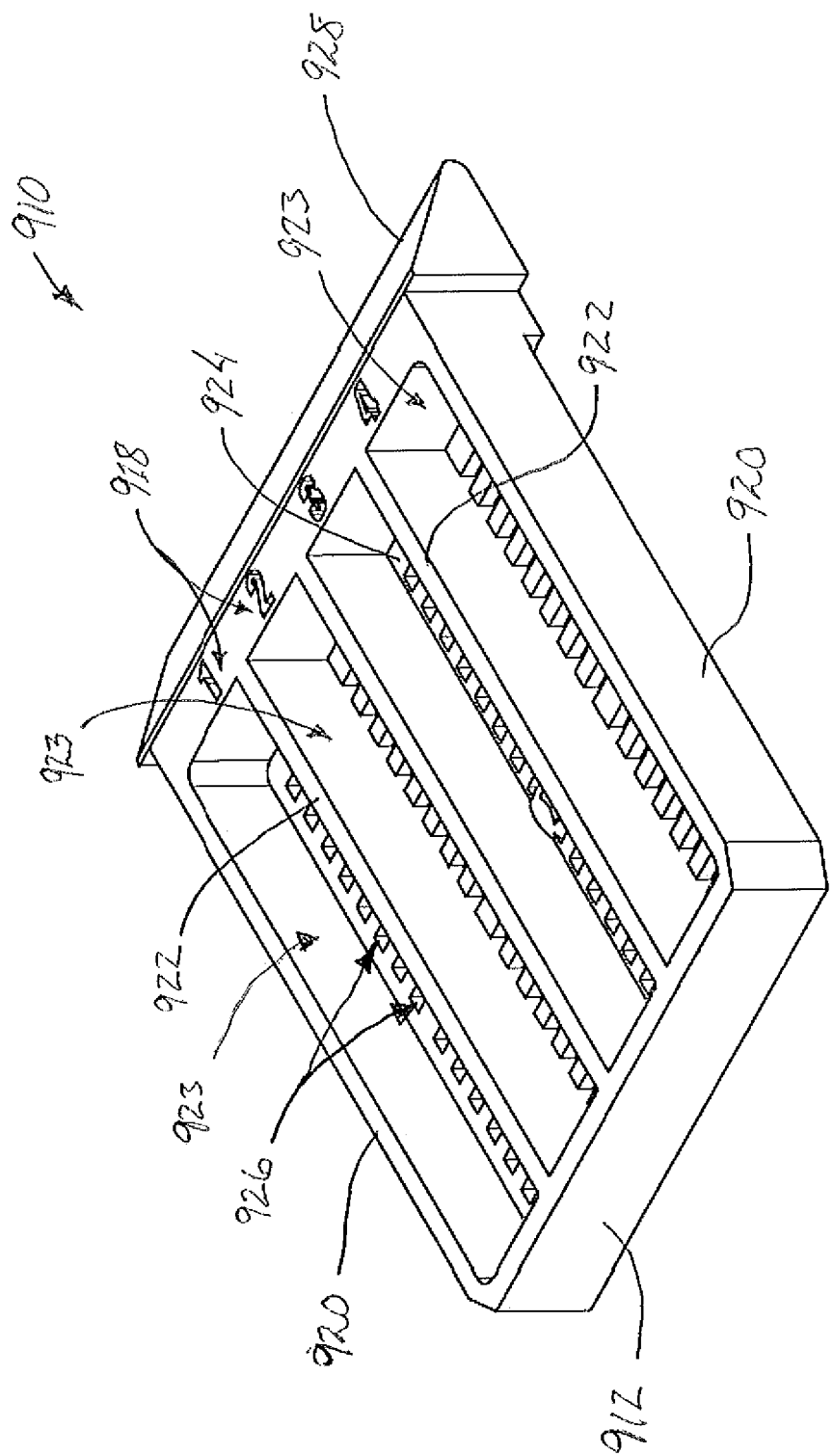
FIG. 28 depicts a perspective view of still another exemplary alternative cassette tray for use with the cover of FIG. 13 in lieu of the cassette tray of FIG. 11.

FIG. 28 shows another exemplary alternative cassette tray (910) that may be readily used with cover (540) described above in lieu of cassette tray (510). It should be understood that cassette tray (910) is substantially similar to cassette tray (510) described above except as otherwise specifically noted herein. For instance, cassette tray (910) comprises a distal wall (912), a proximal wall (916), a pair of sidewalls (920) extending between distal wall (912) and proximal wall (916), and a floor (924) positioned below walls (912, 916, 920). However, unlike cassette tray (510), distal wall (912) is substantially solid and defines no structures similar to openings (514) described above. Thus, cassette tray (910) is generally not configured to receive a tissue samples longitudinally or from the side of cassette tray (910). Instead, tissue samples are generally insertable through the top of cassette tray (910). Like proximal wall (516) described above, proximal wall (916), is solid. Also like proximal wall (516) described above, proximal wall (916) of the present example includes indicia (918) similar to indicia (518) described above.

Like with walls (512, 516, 520) described above, walls (912, 916, 920) are interconnected to form the outer perimeter of cassette tray (910). Cassette tray (910) likewise includes a plurality of inner divider walls (922) similar to inner divider walls (522) described above. Accordingly, walls (912, 916, 920, 922) define a plurality of sample chambers (923) that are configured to hold tissue samples in one or more tissue samples. Although cassette tray (910) of the present example includes three inner divider walls (922) defining four sample chambers (923), it should be understood that in other examples any other suitable number of inner divider walls (922) can be used such as one, two, four, and/or etc. Similarly, in other examples inner divider walls (922) can be omitted entirely.

Like floor (524) described above, floor (924) of the present example is positioned below walls (912, 916, 920). Floor (924) includes a plurality of vents (926). Vents (926) are generally configured to promote the flow of fluid through floor (924), yet maintain tissue samples within each sample chamber (923). To facilitate this configuration, vents (926) have a narrow rectangular form. In other examples, vents (926) can be configured with a variety of alternative shapes such as round, oval-shaped, square, and/or etc. Although vents (926) in the present example are arranged to uniformly occupy the entire surface of floor (924), it should be understood that in other examples vents (926) can be arranged in a variety of other ways.

Floor (924) is opposite to an open space above sample chambers (923). Thus, the upper portion of cassette tray (910) is generally open. Because of this, tissue samples may be deposited into each sample chamber (923) through openings (914) in distal wall (912) or through the open upper portion of cassette tray (910).

As with cassette tray (510) described above, cassette tray (910) further includes a labeling portion (928) protruding proximally from proximal wall (916). Like with labeling portion (528) described above, labeling portion (928) generally defines a triangular or wedge shape that provides a flat smooth surface for printing or otherwise adhering a label to the surface of labeling portion (928). As similarly described above with respect to labeling portion (528), labeling portion (928) is generally configured to provide readily accessible patient information to an operator to aid with tracking of tissue samples as they progress through the biopsy and sample analysis procedure.

Although not shown, it should be understood that cassette tray (910) further comprises a plurality of detents (not shown) disposed on the underside of floor (924). As similarly described above with respect to detents (530, 532), each pair of detents is positioned to provide temporary or selective locking of cassette tray (910) at various positions relative to cover (540) when cassette tray (910) is inserted into cover (540).

In an exemplary use, cassette tray (910) is used similarly to cassette tray (510) described above. However, unlike cassette tray (510) described above, cassette tray (910) is generally not usable with tissue holder assembly (600) due to the closed nature of distal wall (912). Although this generally prevents cassette tray (910) from being used with tissue sample holder assembly (600), this configuration may be beneficial in the context of a biopsy device that is generally configured to collect tissue samples in a bulk configuration. In such contexts, tissue samples may be received directly into cassette tray (910). Alternatively, tissue samples may first be received in a single bulk sample collection cup and then later placed in cassette tray (910).

Figure 29:
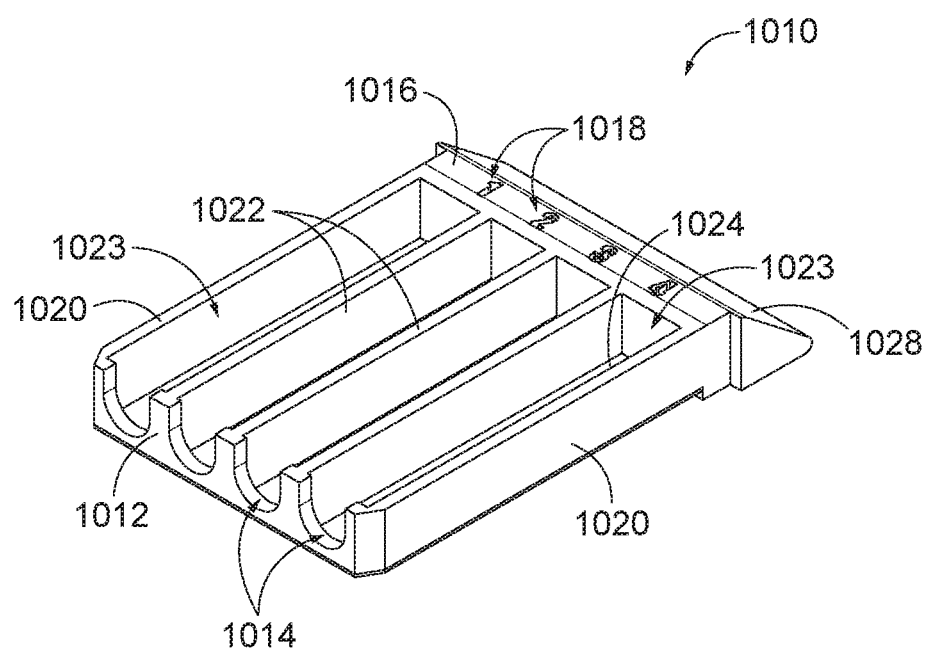
FIG. 29 depicts a perspective view of yet another exemplary alternative cassette tray for use with the cover of FIG. 13 in lieu of the cassette tray of FIG. 11.
Figure 3D:
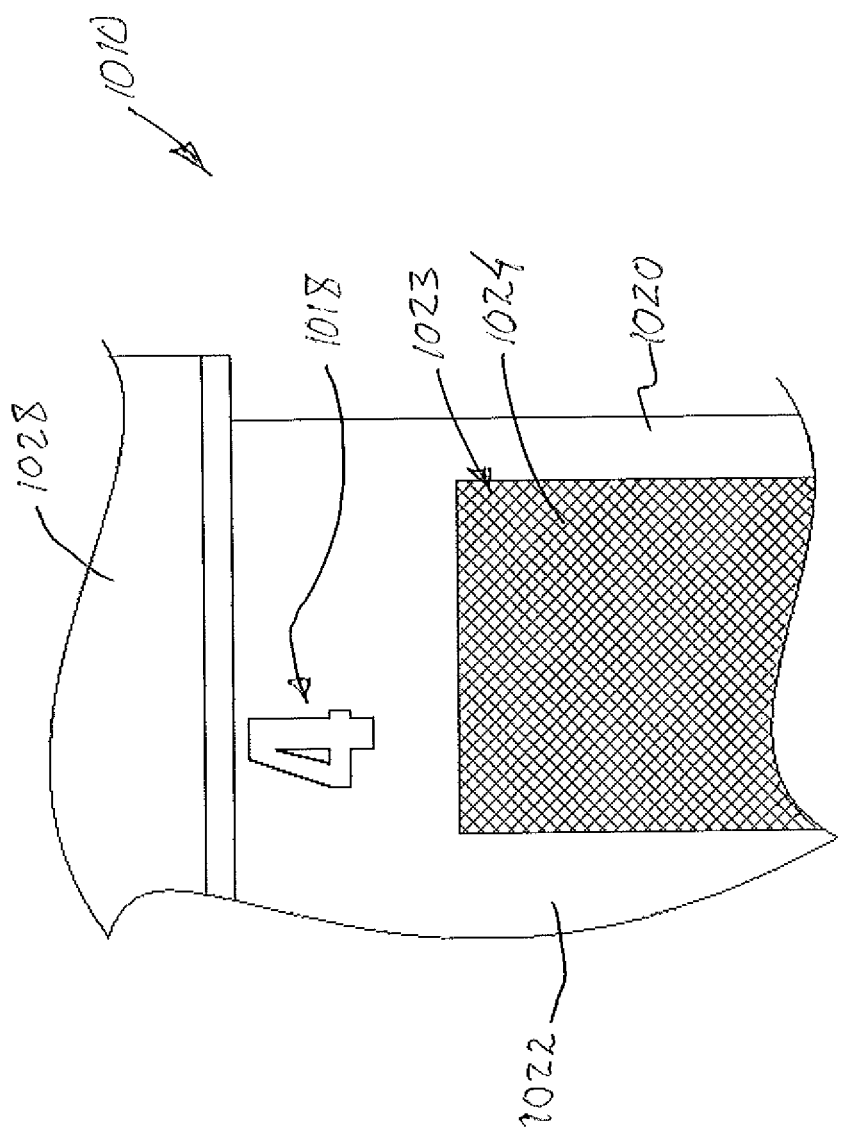

FIGS. 29 and 30 shows another exemplary alternative cassette tray (1010) that may be readily used with cover (540) and/or tissue sample holder assembly (600) described above in lieu of cassette tray (510). It should be understood that cassette tray (1010) is substantially similar to cassette tray (510) described above except as otherwise specifically noted herein. For instance, cassette tray (1010) comprises a distal wall (1012), a proximal wall (1016), a pair of sidewalls (1020) extending between distal wall (1012) and proximal wall (1016), and a floor (1024) positioned below walls (1012, 1016, 1020). Like cassette tray (510), distal wall (1012) defines a plurality of openings (814) similar to openings (514) described above. Like with openings (514) described above, each opening (1014) is generally configured to receive a tissue sample. Like proximal wall (516) described above, proximal wall (1016), is solid. Also like proximal wall (516) described above, proximal wall (1016) of the present example includes indicia (1018) similar to indicia (518) described above.

Like with walls (512, 516, 520) described above, walls (1012, 1016, 1020) are interconnected to form the outer perimeter of cassette tray (1010). Cassette tray (1010) of the present example likewise includes a plurality of inner divider walls (1022) similar to inner divider walls (522) described above. Accordingly, walls (1012, 1016, 1020, 1022) define a plurality of sample chambers (1023) that are configured to hold tissue samples in one or more tissue samples.

Like floor (524) described above, floor (1024) of the present example is positioned below walls (1012, 1016, 1020). However, unlike floor (524) described above, floor (1024) of the present example includes excludes structures similar to vents (526). Instead, as best seen in FIG. 30, floor (1024) is formed of a mesh material. Accordingly, floor (1024) itself is generally configured to promote the flow of fluid, yet maintain tissue samples within each sample chamber (1023) without structures similar to vents (526). To facilitate this configuration, floor (1024) is generally formed of a separate material relative to the rest of cassette tray (1010). Floor (1024) is thus affixed to the underside of walls (1012, 1016, 1020, 1022). Floor (1024) may be affixed to walls (1012, 1016, 1020, 1022) by a variety of mechanism. For instance, in some examples a chemical adhesive is used to bond floor (1024) to walls (1012, 1016, 1020, 1022). In other examples, floor (1024) can be ultrasonically welded to walls (1012, 1016, 1020, 1022). In still other examples, floor (1024) is partially melted and then pressed onto the surface of walls (1012, 1016, 1020, 1022) to adhere floor (1024) to walls (1012, 1016, 1020, 1022).

Floor (1024) is opposite to an open space above sample chambers (1023). Thus, the upper portion of cassette tray (1010) is generally open. Because of this, tissue samples may be deposited into each sample chamber (1023) through openings (1014) in distal wall (1012) or through the open upper portion of cassette tray (1010).

As with cassette tray (510) described above, cassette tray (1010) further includes a labeling portion (1028) protruding proximally from proximal wall (1016). Like with labeling portion (528) described above, labeling portion (1028) generally defines a triangular or wedge shape that provides a flat smooth surface for printing or otherwise adhering a label to the surface of labeling portion (1028). As similarly described above with respect to labeling portion (528), labeling portion (1028) is generally configured to provide readily accessible patient information to an operator to aid with tracking of tissue samples as they progress through the biopsy and sample analysis procedure.

Although not shown, it should be understood that cassette tray (1010) further comprises a plurality of detents (not shown) disposed on the underside of floor (1024). As similarly described above with respect to detents (530, 532), each pair of detents is positioned to provide temporary or selective locking of cassette tray (1010) at various positions relative to cover (540) when cassette tray (1010) is inserted into cover (540).

In an exemplary use, cassette tray (1010) is used similarly to cassette tray (510) described above. For instance, cassette tray (1010) can be similarly inserted into both manifold (640) of tissue sample holder assembly (600) and cover (540). Although this configuration does not prevent cassette tray (1010) from being used with tissue sample holder assembly (600), this configuration may also be beneficial in the context of a biopsy device that is generally configured to collect tissue samples in a bulk configuration. In such contexts, tissue samples may first be received in a single bulk sample collection cup and then later placed in cassette tray (1010).

Figure 31A:
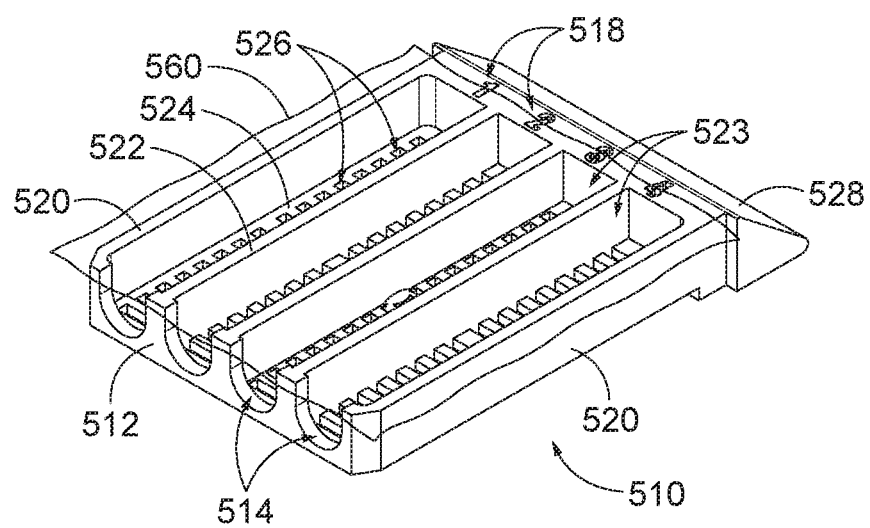
FIG. 31A depicts still another perspective view of the cassette tray of FIG. 11, the cassette tray being used with a sterile cover.

FIG. 31A shows cassette tray (510) being used with an exemplary sterile cover (560). As described above, cassette tray (510) is generally insertable into manifold (640) of tissue sample holder assembly (600). Because manifold (640) interacts with tissue samples, manifold (640) generally has certain sterility requirements before being used in a biopsy procedure. Because cassette tray (510) is used with manifold (640), cassette tray (510) may also have certain sterility requirements. However, since only the interior of cassette tray (510) actually contacts tissue samples, such sterility requirements may be limited only to the interior of cassette tray (510) (e.g., sample chambers (523)).

As also described above, it may be desirable to print, or otherwise attach a label to labeling portion (528) prior to performing a biopsy procedure. In some instances, this may include inserting cassette tray (510) into a label printer to perform printing or laser etching directly onto the surface of labeling portion (528). However, because portions of cassette tray (510) may have certain sterility requirements, merely inserting cassette tray (510) into a label printer or other device before performing a biopsy procedure may disrupt such sterility requirements if the printer itself is not sterile. Thus, it may be desirable to maintain the sterility of at least a portion of cassette tray (510) prior to performing a biopsy procedure.

Sterile cover (560) comprises a thin film that is configured to fit over at least a portion of cassette tray (510). In the present example, sterile cover (560) is generally sized to fit over the entire top surface of cassette tray (510) to cover the entirety of sample chambers (523). This configuration generally protects the sterility of the interior of cassette tray (510) to permit use of cassette tray (510) with a label printer or other device prior to a biopsy procedure. Although not shown, it should be understood that in some examples sterile cover (560) may also be sized to extend around the top of cassette tray (510) and over distal wall (512) of cassette tray (510) to also cover each opening (514) defined by distal wall (512). In still other examples, sterile cover (560) can be configured as a sleeve or sheath covering the exterior of cassette tray (510) with the exception of labeling portion (528). In such an example, sterile cover (560) can be configured to receive cassette tray (510) as similarly described above with respect to cover (540). Thus, it should be understood that in some examples sterile cover (560) can have the form of a rectangular box with an open end to receive cassette tray (510).

Sterile cover (560) of the present example is generally comprised of a generally transparent material. Such a configuration generally permits an operator to visually inspect cassette tray (510) prior to use. However, it should be understood that in other examples sterile cover (560) may be opaque or partially transparent.

Sterile cover (560) is generally removably adhered to the exterior of cassette tray (510). This permits sterile cover (560) to remain attached to cassette tray (510) for use with a label printer or other device prior to a biopsy procedure, while still permitting an operator to remove sterile cover (560) immediately before a biopsy procedure. Sterile cover (560) can be adhered to the exterior of cassette tray (510) by a variety of mechanisms. For instance, in the present example the underside of sterile cover (560) is coated with a chemical adhesive and then sterile cover (560) is applied during packaging of cassette tray (510). In other examples, sterile cover (560) comprises a sleeve of material that is responsive to heat such that cassette tray (510) is "shrink wrapped" during packaging. In still other examples, adhesive is applied directly to cassette tray (510) and then sterile cover (560) is applied to cassette tray (510). Still other examples of adhering sterile cover (560) to cassette tray (510) will be apparent to those of ordinary skill in the art in view of the teachings herein.

Figure 31B:
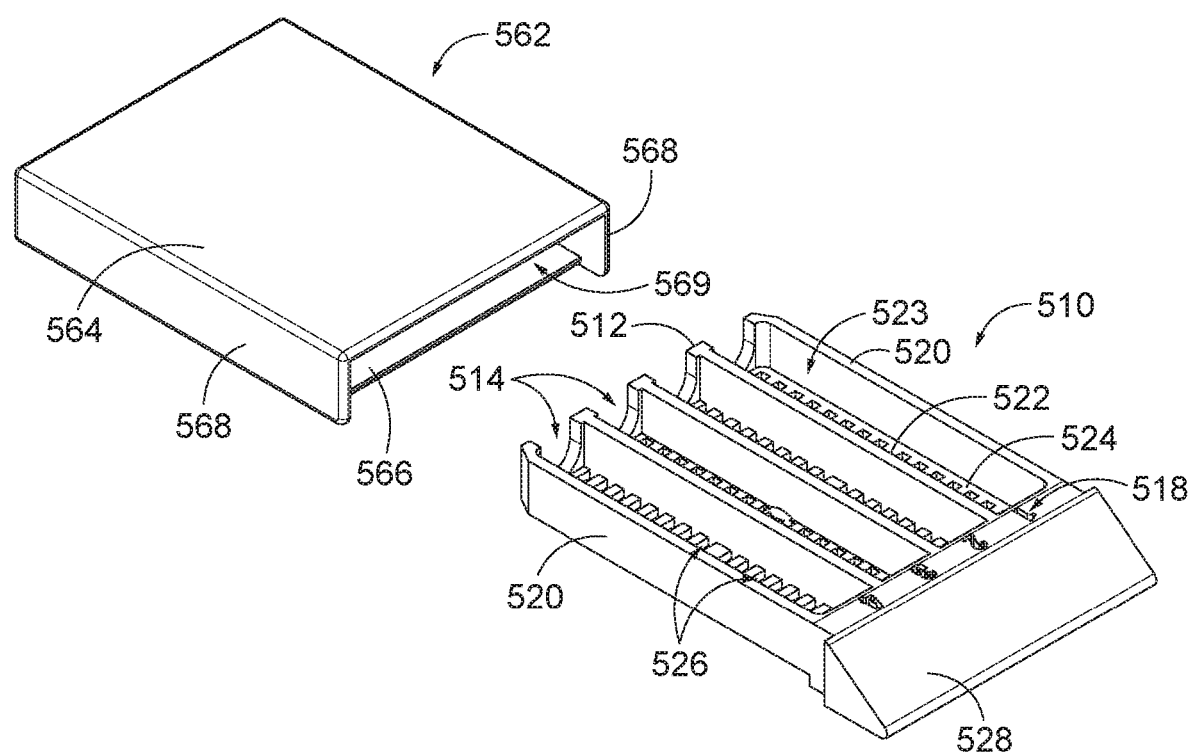
FIG. 31B depicts still another perspective view of the cassette tray of FIG. 11, the cassette tray being used with another sterile cover.

FIG. 31B shows cassette tray (510) being used with another exemplary sterile cover (562). As described above, cassette tray (510) is generally insertable into manifold (640) of tissue sample holder assembly (600). Because manifold (640) interacts with tissue samples, manifold (640) generally has certain sterility requirements before being used in a biopsy procedure. Because cassette tray (510) is used with manifold (640), cassette tray (510) may also have certain sterility requirements. However, since only the interior of cassette tray (510) actually contacts tissue samples, such sterility requirements may be limited only to the interior of cassette tray (510) (e.g., sample chambers (523)).

As also described above, it may be desirable to print, or otherwise attach a label to labeling portion (528) prior to performing a biopsy procedure. In some instances, this may include inserting cassette tray (510) into a label printer to perform printing or laser etching directly onto the surface of labeling portion (528). However, because portions of cassette tray (510) may have certain sterility requirements, merely inserting cassette tray (510) into a label printer or other device before performing a biopsy procedure may disrupt such sterility requirements if the printer itself is not sterile. Thus, it may be desirable to maintain the sterility of at least a portion of cassette tray (510) prior to performing a biopsy procedure.

Sterile cover (562) comprises a rectangularly-shaped box that is configured to fit over at least a portion of cassette tray (510). In the present example, sterile cover (562) generally corresponds to the same shape as cover (540). However, unlike cover (540), sterile cover (562) is generally solid to permit sterile coverage of the entirety of sample chambers (523) of cassette tray (510). This configuration generally protects the sterility of cassette tray (510) to permit use of cassette tray (510) with a label printer or other device prior to a biopsy procedure. Thus, sterile cover (562) is generally sized to extend around the top of cassette tray (510) and over distal wall (512) of cassette tray (510) to also cover each opening (514) defined by distal wall (512). Sterile cover (562) is further configured as a sleeve or sheath covering the exterior of cassette tray (510) with the exception of labeling portion (528). Accordingly, sterile cover (562) can be configured to receive cassette tray (510) as similarly described above with respect to cover (540).

Sterile cover (562) of the present example is generally comprised of a generally transparent material. Such a configuration generally permits an operator to visually inspect cassette tray (510) prior to use. However, it should be understood that in other examples sterile cover (562) may be opaque or partially transparent.

Sterile cover (562) of the present example is also generally comprised of a generally hard material. This permits sterile cover (562) to generally retain its shape, although the material of sterile cover (562) may permit some flexibility. The material of sterile cover (562) defines a solid top (564), a solid bottom (566), and a plurality of sidewalls (568) extending between top (564) and bottom (566). Sidewalls (568) are oriented on three sides of sterile cover (562), while the proximal end of sterile cover (562) omits a structure similar to sidewalls (568) such that sterile cover (562) defines an open proximal end (569) configured to receive the distal end of cassette tray (510).

In use, sterile cover (562) is generally receives cassette tray (510) in lieu of cover (540) to protect the sterility of distal wall (512), sidewalls (520), inner divider walls (522), and floor (524). This permits sterile cover (562) to remain attached to cassette tray (510) for use with a label printer or other device prior to a biopsy procedure, while still permitting an operator to remove sterile cover (562) immediately before a biopsy procedure. Once such labeling is finished, sterile cover (562) can be readily removed from cassette tray (510). Cassette tray (510) can then be used in a biopsy procedure. Once the biopsy procedure is complete, cover (540) can receive cassette tray (510) instead of sterile cover (562) for further procedural operations such as those shown in FIG. 7.

Figure 32:
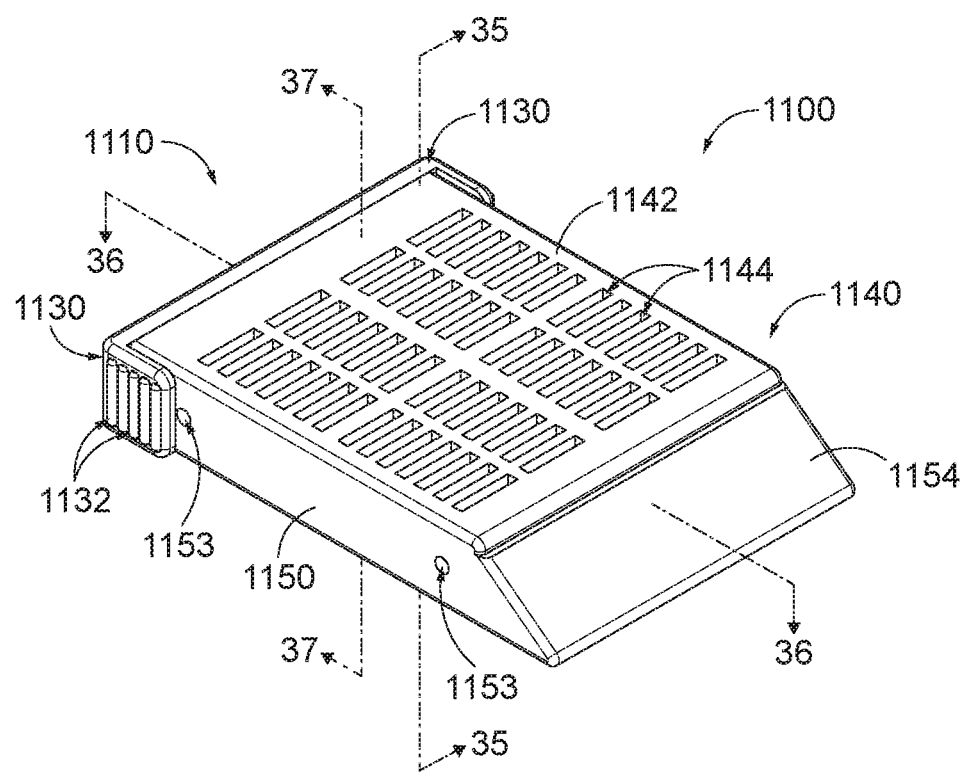
FIG. 32 depicts a perspective view of an exemplary alternative cassette assembly that may be readily used with the biopsy device of FIG. 1 in lieu of the tissue sample tray of FIG. 3 and/or the sample cassette of FIG. 6.

FIG. 32 shows another exemplary alternative cassette assembly (1100) that may be used in lieu of cassette assembly (500) described above. It should be understood that cassette assembly (1100) is substantially similar to cassette assembly (500) described above except where otherwise explicitly noted herein. For instance, like with cassette assembly (500), cassette assembly (1100) includes a cassette tray (1110) and a cover (1140).

Figure 33:
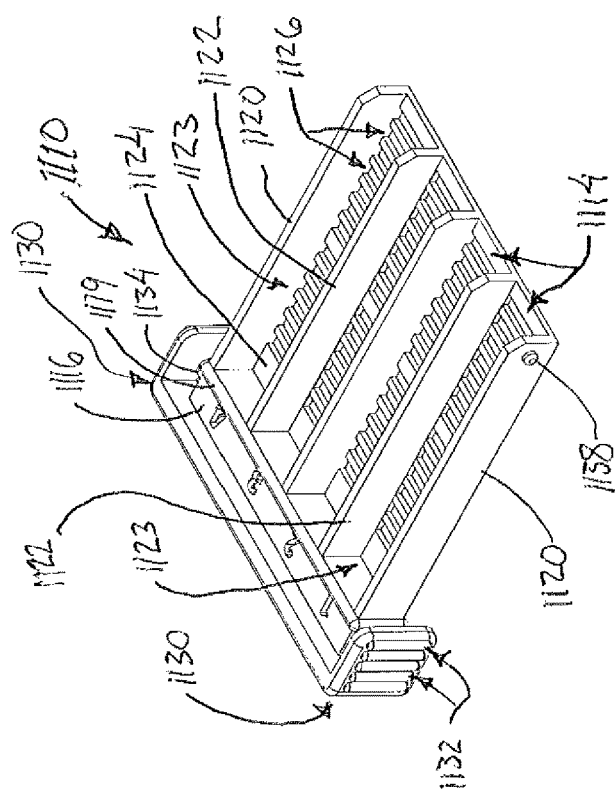
FIG. 33 depicts a perspective view of a cassette tray of the cassette assembly of FIG. 32.

Cassette tray (1110) of the present example is substantially similar to cassette tray (510) described above except as otherwise explicitly noted herein. For instance, as best seen in FIG. 33, cassette tray (1110) comprises a proximal wall (1116), a pair of sidewalls (1120) extending from proximal wall (1116), and a floor (1124) positioned below walls (1116, 1120). However, unlike cassette tray (510), cassette tray (1110) of the present example omits a structure similar to distal wall (512). Instead, sidewalls (1120) merely terminate at a distal end, thereby defining a plurality of openings (1114) similar to openings (514) described above. Like with openings (514) described above, each opening (1114) is generally configured to receive a tissue sample.

Like proximal wall (516) described above, proximal wall (1116), is solid. Also like proximal wall (516) described above, proximal wall (1116) of the present example includes indicia (1118) similar to indicia (518) described above. However, unlike proximal wall (516) described above, proximal wall (1116) further includes a sealing member (1119) positioned adjacent to indicia (1118). As will be described in greater detail below, sealing member (1119) generally protrudes outwardly from proximal wall (1116) to promote sealing of proximal wall (1116) with at least a portion of cover (1140).

Like with walls (512, 516, 520) described above, walls (1116, 1120) are interconnected to form the outer perimeter of cassette tray (1110). Cassette tray (1110) of the present example likewise includes a plurality of inner divider walls (1122) similar to inner divider walls (522) described above. Accordingly, walls (1116, 1120, 1122) define a plurality of sample chambers (1123) that are configured to hold tissue samples in one or more tissue samples.

Like floor (524) described above, floor (1124) of the present example is positioned below walls (1116, 1120). Floor (1124) includes a plurality of vents (1126). Vents (1126) are generally configured to promote the flow of fluid through floor (1124), yet maintain tissue samples within each sample chamber (1123). To facilitate this configuration, vents (1126) have a narrow rectangular form. In other examples, vents (1126) can be configured with a variety of alternative shapes such as round, oval-shaped, square, and/or etc. Although vents (1126) in the present example are arranged to uniformly occupy the entire surface of floor (1124), it should be understood that in other examples vents (1126) can be arranged in a variety of other ways.

Floor (1124) is opposite to an open space above sample chambers (1123). Thus, the upper portion of cassette tray (1110) is generally open. Because of this, tissue samples may be deposited into each sample chamber (1123) through openings (1114) in distal or through the open upper portion of cassette tray (1110).

It should be understood that cassette tray (1110) of the present example omits structures similar to detents (530, 532) described above. Instead, cassette tray (1110) includes a coupling portion (1130) that is generally associated with proximal wall (1116). As will be described in greater detail below, coupling portion (1130) is generally configured to engage at least a portion of cover (1140) to removably secure cassette tray (1110) to cover (1140). Coupling portion (1130) includes a grip portion (1132) disposed on each side of proximal wall (1116). Each grip portion (1132) generally forms an L-shaped configuration around proximal wall (1116) in a direction parallel with each sidewall (1120) such that at least a portion of each grip portion (1132) is offset from each sidewall (1120). The configuration of each grip portion (1132) is generally configured to permit manipulation of cassette tray (1110) by an operator. As will be understood, this manipulation of cassette tray (1110) is permitted even when cassette tray (1110) is fully inserted into cover (1140).

Figure 35:
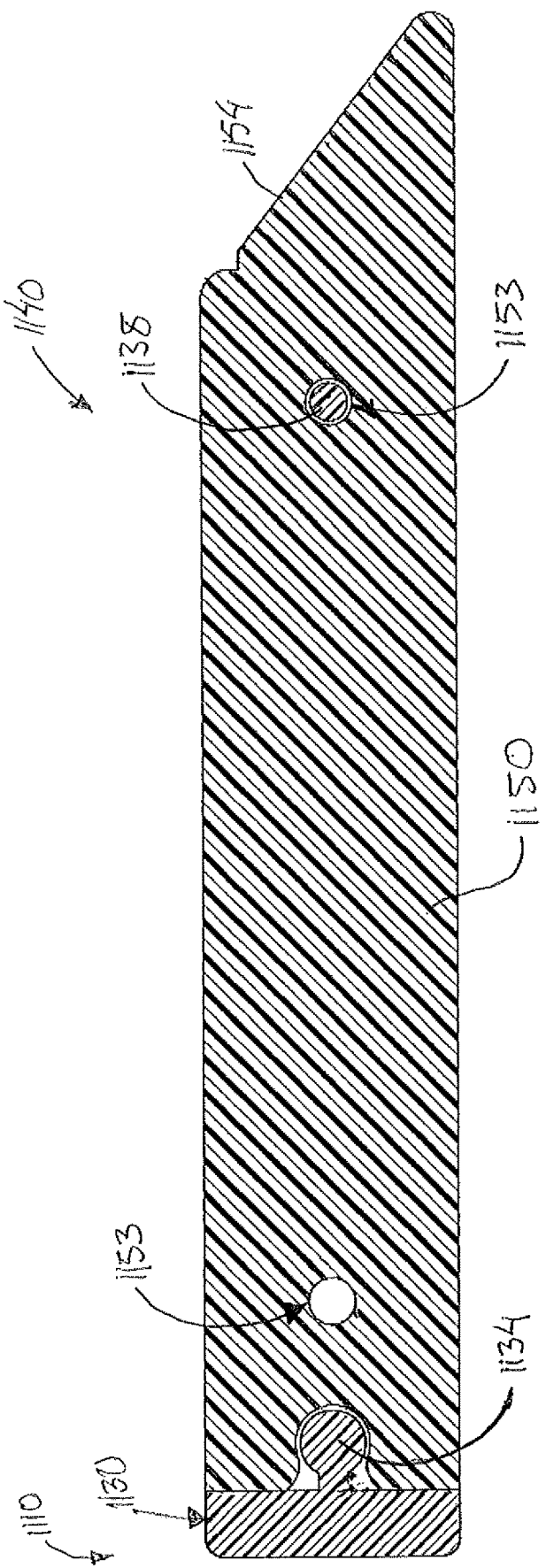
FIG. 35 depicts a side cross-sectional view of the cassette assembly of FIG. 32, the cross-section taken along line 35-35 of FIG. 32.

Coupling portion (1130) further includes a coupler (1134) extending from a portion of each grip portion (1132) and into proximal wall (1116). As best seen in FIG. 35, each coupler (1134) defines a generally cylindrical cross-sectional shape. As will be described in greater detail below, each coupler (1134) is generally configured to engage with at least a portion of cover (1140) to provide a snap-fit coupling with cover (1140).

In addition to coupling portion (1130), each sidewall (1120) includes a single detent (1138) positioned adjacent to the distal end of cassette tray (1110). Each detent (1138) is generally configured as a round projection extending outwardly from each sidewall (1120). As will be described in greater detail below, each detent (1138) is generally configured to engage one or more portions of cover (1140) to temporarily lock cassette tray (1110) at a plurality of predetermined positions relative to cover (1140).

Figure 34:
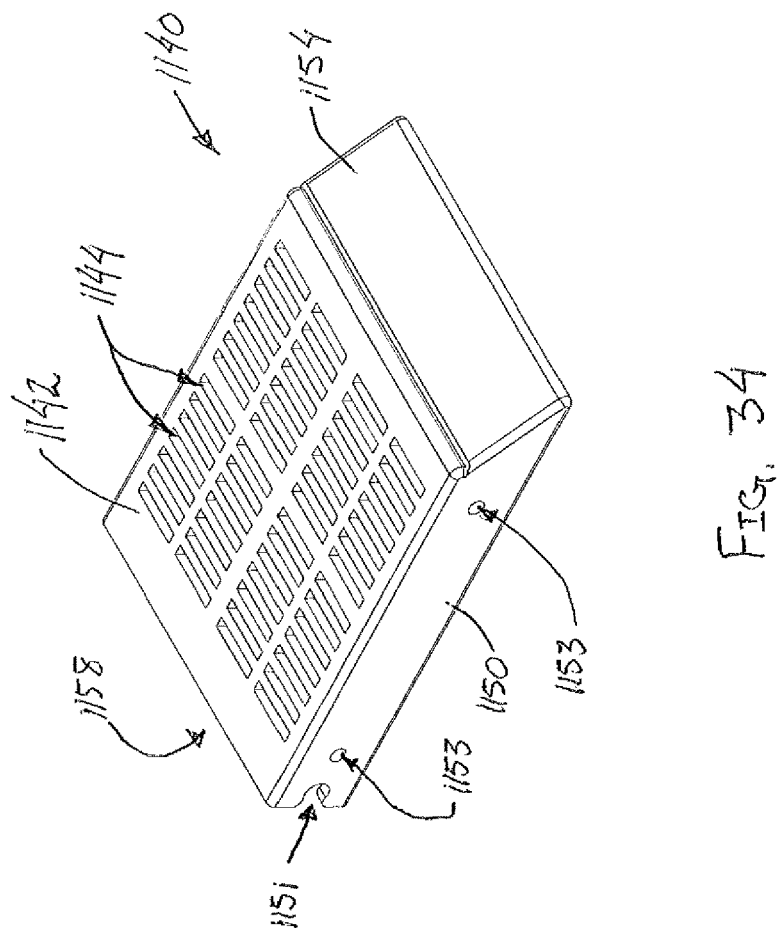
FIG. 34 depicts a perspective view of a cover of the cassette assembly of FIG. 32.

FIG. 34 shows cover (1140) in greater detail. It should be understood that cover (1140) is generally substantially similar to cover (540) described above except where as otherwise explicitly noted herein. For instance, like with cover (540), cover (1140) comprises a filter portion (1142), a support portion (not shown), and a pair of sidewalls (1150) extending between the filter portion (1142) and the support portion (not shown). Filter portion (1142) is similar to floor (1124) described above in that filter portion (1142) includes a plurality of vents (1144) arranged in an array about the surface of filter portion (1142). Vents (1144) are generally configured to promote the flow of fluid through filter portion (1142), yet maintain tissue samples within each sample chamber (1123) of cassette tray (1110) when cassette tray (1110) is inserted into cover (1140). To facilitate this configuration, vents (1144) have a narrow rectangular form. In other examples, vents (1144) can be configured with a variety of alternative shapes such as round, oval-shaped, square, and/or etc. Although vents (1144) in the present example are arranged to uniformly occupy the entire surface of filter portion (1142), it should be understood that in other examples vents (1144) can be arranged in a variety of other ways. For instance, vents (1144) can be isolated to a specific region or multiple regions of filter portion (1142). Of course, other alternative arrangements for vents (1144) will be apparent to those of ordinary skill in the art in view of the teachings herein.

The support portion is similar to support portion (546) described above. For instance, the support portion includes a support structure (not shown) defining a plurality of open spaces (not shown). Like with support portion (546), the support portion is generally adjacent to floor (1124) of cassette tray (1110) when cassette tray (1110) is inserted into cover (1140). Thus, including structures similar to vents (1144) is not entirely necessary due to the presence of vents (1126) in floor (1124) of cassette tray (510). However, it should be understood that in some examples the support portion can include structures similar to vents (1144).

As described above, cover (1140) includes sidewalls (1150) extending between filter portion (1142) and the support portion. Sidewalls (1150) are both solid to generally promote rigidity of cover (1140). In addition, sidewalls (1150) each include one or more detent openings (1153) and a receiver (1151). As will be described in greater detail below, openings (1153) are generally configured to receive a detent (1138) of cassette tray (1110) to temperately lock cassette tray (1110) at a plurality of positions relative to cover (1140). As will also be described in greater detail below, receiver (1151) is generally configured to receive coupler (1134) of cassette tray (1110). As best seen in FIG. 35, this configuration permits coupler (1134) and receiver (1151) to create a complementary snap-fit feature that removably locks cassette tray (1110) onto cover (1140).

In addition to sidewalls (1150), cover (1140) further includes a labeling portion (1154), which acts as a distal wall similar to distal wall (544) described above. Sidewalls (1150), labeling portion (1154), filter portion (1142), and the support portion together are configured to define an enclosure for cassette tray (1110) that holds tissue samples within cassette tray (1110), while permitting fluid to flow through cassette tray (1110).

Opposite labeling portion (1154), filter portion (1142), the support portion, and sidewalls (1150) define a proximal opening (1158). Proximal opening (1158) is generally configured to receive at least a portion of cassette tray (1110) such that cassette tray (1110) may be inserted into cover (1140). Although proximal opening (1158) is shown in the present example as having a generally rectangular shape, it should be understood that proximal opening (1158) is generally a function of the shape of cover (1140) and cassette tray (1110). Thus, in examples where cassette tray (1110) and/or cover (1140) take on different shapes, proximal opening (1158) may also be correspondingly different.

As described above, cover (1140) includes labeling portion (1154). Labeling portion (1154) of the present example is similar to labeling portion (528) described above with respect to cassette tray (510). However, unlike labeling portion (528) described above, labeling portion (1154) is integrated into cover (1140) rather than cassette tray (1110). This configuration may be beneficial in some contexts where preserving sterility of cassette tray (1110) is desirable. For instance, in the present example cover (1140) can be used with a label printer or engraver to apply a label to labeling portion (1154) independently of how cassette tray (1110) is used. Thus, a user may apply a label to labeling portion (1154) prior to a biopsy procedure without impacting the sterility of cassette tray (1110).

Figure 36A:
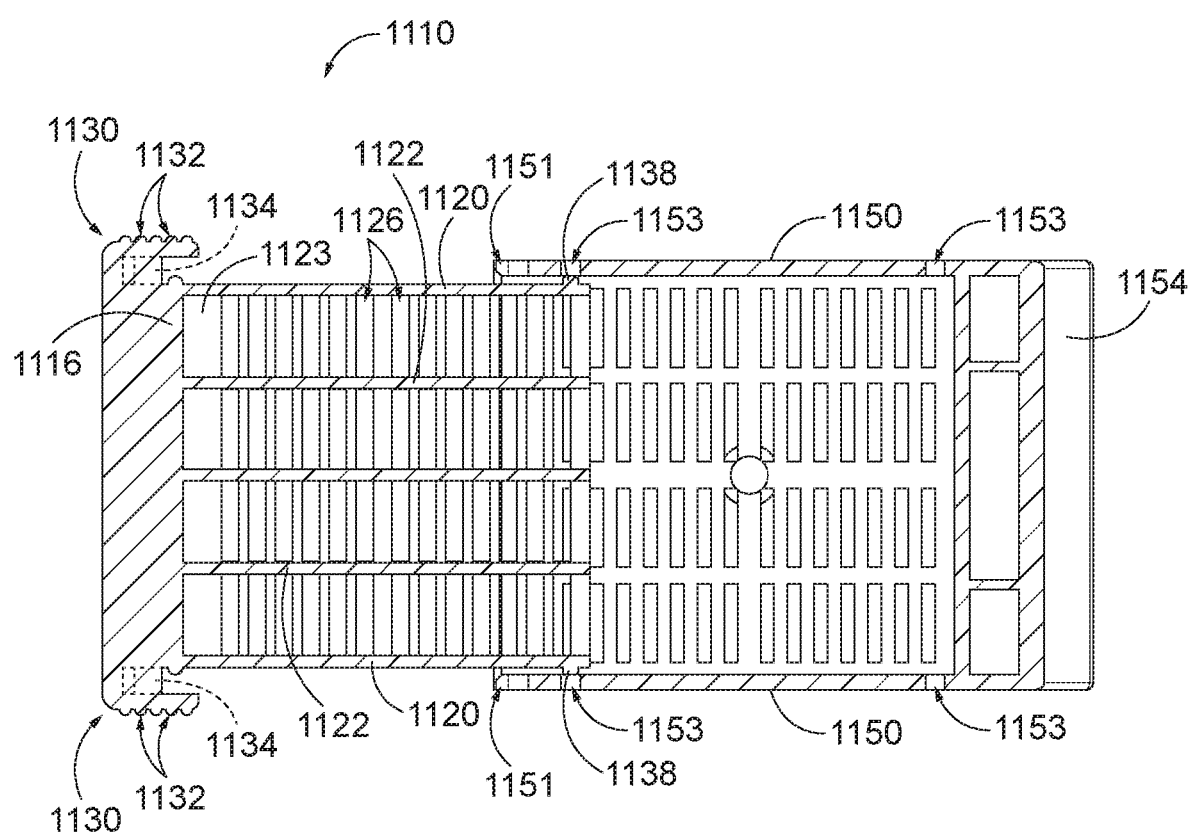
FIG. 36A depicts a top cross-sectional view of the cassette assembly of FIG. 32, with the cassette tray of FIG. 33 initially inserted into the cover of FIG. 34.
Figure 36B:
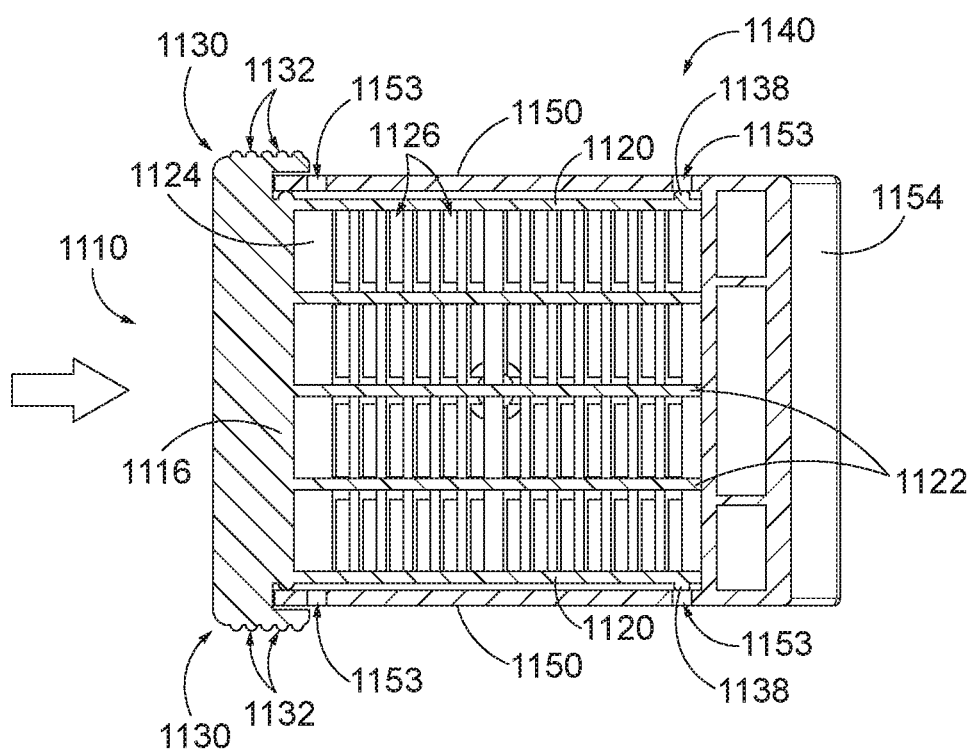
FIG. 36B depicts another top cross-sectional view of the cassette assembly of FIG. 32, with the cassette tray of FIG. 33 fully inserted into the cover of FIG. 34.
Figure 37:
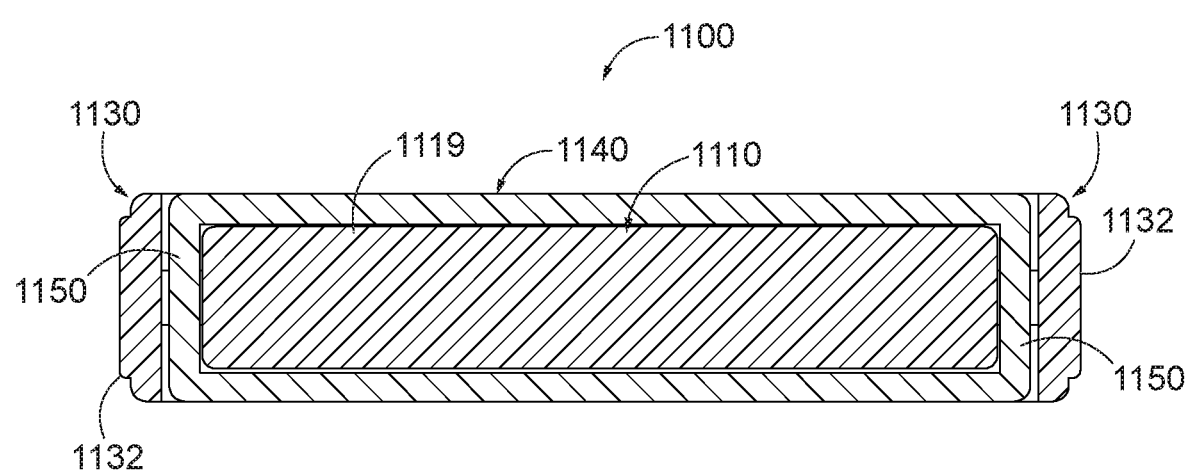
FIG. 37 depicts a front cross-sectional view of the cassette assembly of FIG. 32, the cross-section taken along line 37-37 of FIG. 32.

FIGS. 36A-37 show an exemplary insertion of cassette tray (1110) into cover (1140). As can be seen in FIG. 36A, the distal end of cassette tray (1110) is initially inserted into the proximal end of cover (1140). Insertion proceeds until detents (1138) of cassette tray (1110) engage detent openings (1153) of cover (1140). Once detents (1138) engage detent openings (1153), cassette tray (1110) is temporarily locked at an intermediate position relative to cover (1140). At this stage, tissue samples contained within cassette tray (1110) may be manipulated, visualized, and/or etc.

For full insertion of cassette tray (1110) into cover (1140), an operator can apply a distally oriented force to cassette tray (1110) to thereby disengage detents (1138) from detent openings (1153). Once detents (1138) are disengaged from detent openings (1153), cassette tray (1110) can move freely distally within cover (1140) towards the fully inserted position shown in FIG. 36B.

Once cassette tray (1110) reaches the fully inserted position shown in FIG. 36B, detents (1138) of cassette tray (1110) engage another set of detent openings (1154) oriented within sidewalls (1150) of cover (1140) adjacent to the distal end of cover (1140). Once detents (1138) are engage in detent openings (1154), cassette tray (1110) is removably locked within cover. Although the present example is shown as having only two sets of detent openings (1154), it should be understood that in other examples cover (1140) can include a plurality of sets of detent openings (1154). In such configurations, cassette tray (1110) can lock at a plurality of positions prior to locking at the positions shown in FIG. 36.

Returning to FIG. 35, it should be understood that once cassette tray (1110) is moved to the fully inserted position, coupler (1134) of cassette tray (1110) is also received within receiver (1151) of cover (1140). As described above, coupler (1134) and receiver (1151) cooperate to form a snap-fit coupling between cassette tray (1110) and cover (1140). This snap-fit coupling provides an additional fastening mechanism to hold cassette tray (1110) in the fully inserted position. Accordingly, it should be understood that in some examples additional force may be required to move cassette tray (1110) into and out of the fully inserted position versus the intermediate position described above.

FIG. 37 also shows engagement between sealing member (1119) of cassette tray (1110) and the interior of cover (1140). As can be seen, sealing member (1119) generally expands the size of cassette tray (1110) defined by proximal wall (1116) to seal the proximal end of cassette tray (1110) relative to the exterior of cover (1140). This configuration generally promotes the flow of fluid through vents (1144) of cover (1140) and through vents (1126) of cassette tray (1110) so that fluid can accumulate within sample chambers (1123) of cassette tray (1110).

In the greater context, cassette tray (1110) is used similarly to cassette tray (510) described above. For instance, cassette tray (1110) can be similarly inserted into both manifold (640) of tissue sample holder assembly (600) and cover (1140). As similarly described above with respect to cassette tray (510), once cassette tray (1110) is inserted within manifold (640) of tissue sample holder assembly (600), tissue samples may be successively collected within sample chambers (1123) of cassette tray (1110). Once cassette tray (1110) is full, cassette tray (1110) can then be removed, subjected to procedure room x-ray, and then inserted into cover (1140) for transport to a pathology lab. Although not shown, it should be understood that in contexts where tissue sample holder assembly (600) is used with cassette tray (1110), manifold (640) of tissue sample holder assembly (600) can be equipped with features similar to receiver (1151) of cover (1140). When such receivers are integrated into manifold (640), cassette tray (1110) can couple to manifold (640) as similarly described above with respect to cover (1140).

V. Exemplary Alternative Tissue Sample Holder Assembly with Multiple Manifolds

In some instances, it may be desirable to collect additional samples using multiple cassette trays similar to cassette tray (510) described above. For instance, as described above, cassette tray (510) includes only four sample chambers (523). However, during some biopsy procedures more samples may be required to fully excise a suspicious lesion. In the examples described above, acquiring additional samples may be accomplished by simply replacing a filled cassette tray (510) with a new empty cassette tray (510) within manifold (640) of tissue sample holder assembly (600). However, this may be undesirable to some operators because this replacing cassette trays (510) can add additional procedure time. Accordingly, in some instances it may be desirable to use a tissue sample holder assembly similar to tissue sample holder assembly (600) described above, but with the capacity to receive multiple cassette trays (510).

A. Exemplary Alternative Tissue Sample Holder Assembly with Dual Manifolds

Figure 38:
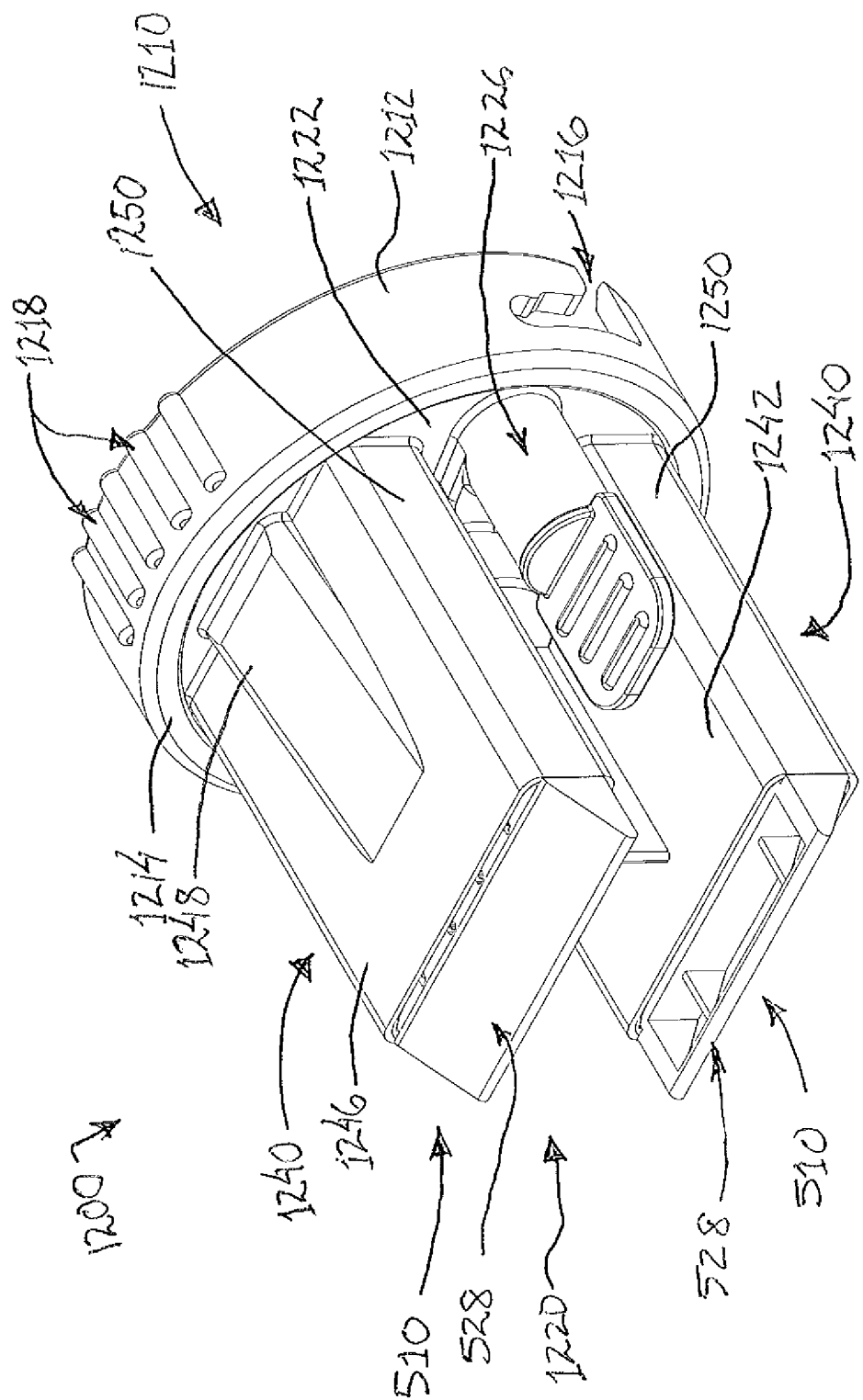
FIG. 38 depicts a perspective view of another exemplary alternative tissue sample holder assembly that may be readily incorporated into the biopsy device of FIG. 1 in lieu of the tissue sample holder assembly of FIG. 2.
Figure 39:
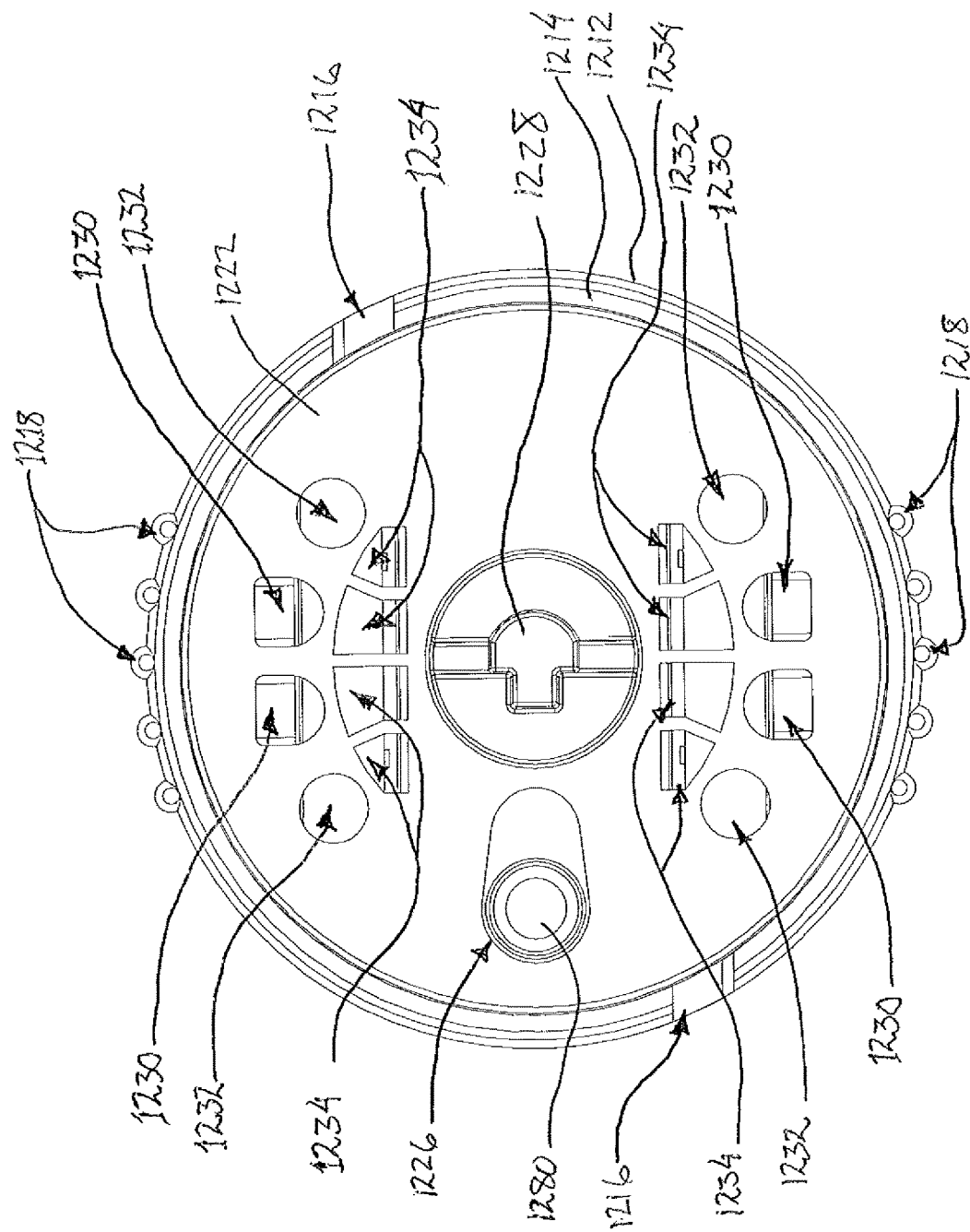
FIG. 39 depicts a front elevational view of the tissue sample holder assembly of FIG. 38.

FIGS. 38 and 39 show an exemplary alternative tissue sample holder assembly (1200) that can be used in connection with cassette assembly (500) described above. Unless otherwise described herein, tissue sample holder assembly (1200) is substantially similar to tissue sample holder assembly (600) described above. For instance, like with tissue sample holder assembly (600), tissue sample holder assembly (1200) of the present example comprises a coupler (1210), a rotatable member (1220), and a plug (1280). Coupler (1210) comprises a generally ring-shaped body (1212) with a sealing lip (1214), a pair of bayonet connectors (1216), and a plurality of grips (1218). Sealing lip (1214) is configured to engage at least a portion of rotatable member (1220) to seal rotatable member (1220) relative to coupler (1210) and probe assembly (20). In addition, sealing lip (1214) is configured to permit rotation of rotatable member (1220) relative to coupler (1210) and probe assembly (20). As will be described in greater detail below, this rotation permits one or more cassette trays (510) to be moved relative to probe assembly (20) so that a single tissue sample can be collected within each sample chamber (523) of each cassette tray (510).

Bayonet connectors (1216) are configured to receive a pair of bayonet pins (not shown) of probe assembly (20) to selectively couple coupler (1210) to probe assembly (20). Thus, bayonet connectors (1216) and the bayonet pins of probe assembly (20) form a standard bayonet coupling assembly to selectively secure coupler (1210) to probe assembly (20). In this configuration, ring-shaped body (1212) is generally rotatable relative to probe assembly (20) to lock and unlock coupler (1210) relative to probe assembly (20). To assist an operator with rotation of ring-shaped body (1212), coupler (1210) includes grips (1218) to enhance grip of ring-shaped body (1212) during locking and unlocking. Although the present example uses a bayonet coupling to secure coupler (1210) to probe assembly (20), it should be understood that in other examples various alternative coupling features can be used as will be apparent to those of ordinary skill in the art in view of the teachings herein.

Rotatable member (1220) is generally configured to receive two cassette trays (510) and position each cassette tray (510) relative to probe assembly (20) to thereby collect a tissue sample within each sample chamber (523) of each cassette tray (510). Except where as otherwise noted herein, rotatable member (1220) is substantially the same as rotatable member (620) described above. For instance, like with rotatable member (620) described above, rotatable member (1220) comprises a circular base (1222), an access port (1226) protruding proximally from base (1222), and two manifolds (1240), also protruding from base (1222). The circular shape of base (1220) is generally configured for receipt within coupler (1210) such that at least a portion of base (1220) abuts sealing lip (1214) of coupler (1210).

Access port (1226) defines a hollow cylindrical protrusion protruding proximally from base (1222). As will be described in greater detail below, access port (1226) is generally configured to receive plug (1280) to seal access port (1226) relative to the exterior of base (1222). However, plug (1280) is generally selectively removable to permit accessibility of access port (1226). Access port (1226) is generally sized to receive a marker deployment instrument or other medical instruments. As will be described in greater detail below, rotatable member (1220) can be rotated to align access port (1226) with the cutter of needle (22). When access port (1226) is aligned with the cutter of needle (22), access port (1226) can be used to gain access to the biopsy site through the cutter of needle (22). As will be understood, this feature may be used for marking purposes or other medical purposes.

Each manifold (1240) is substantially the same as manifold (640) described above, except where otherwise explicitly noted herein. For instance, like with manifold (640), each manifold (1240) of the present example comprises a lower wall (1242), an upper wall (1246), and a pair of sidewalls (1250) extending between the lower wall (1242) and the upper wall (1246). Walls (1242, 1246, 1250) together define a generally rectangular box that is configured to receive cassette tray (510). Walls (1242, 1246, 1250) further define an inner chamber (not shown) that is large enough to accommodate cassette tray (510), while also providing fluid flow through manifold (1240).

Upper wall (1246) of each manifold (1240) includes a raised connector (1248) that is generally hollow such that a portion of the inner chamber is defined by raised connector (1248). As will be described in greater detail below, raised connector (1248) is generally configured to receive tissue samples axially relative to the longitudinal axis of rotatable member (1220) and direct tissue samples downwardly into cassette tray (510). Although raised connector (1248) is shown as a single discrete part that is integral with upper wall (1246), it should be understood that in other examples raised connector (1248) can be a separate part, formed of more than one part, or a combination of both.

As best seen in FIG. 39, the inner chamber of each manifold (1240) communicates with probe assembly (20) via a plurality of openings (1230, 1232, 1234) defined by and extending axially through circular base (1222). In particular, circular base (1222) defines four sample openings (1230, 1232) and four vacuum openings (1234). Of the four sample openings (1230, 1232), circular base (1222) defines two upper sample openings (1230) and two lower sample openings (1232). In this configuration, upper sample openings (1230) communicate with the portion of the inner chamber of each manifold (1240) that is defined by raised connector (1248), while lower sample openings (1232) are in communication with the portion of the inner chamber that is defined by walls (1242, 1246, 1250). As described above, rotatable member (1220) is generally rotatable to place a particular sample chamber (523) of cassette tray (510) into communication with the cutter of needle (22). However, since cassette tray (510) is generally of a flat configuration, upper sample openings (1230) are positioned above lower sample openings (1232) to accommodate both the rotation of rotatable member (1220) and the flat configuration of cassette tray (510).

In contrast to sample openings (1230, 1232), vacuum openings (1234) are generally aligned along a common axis. However, to accommodate rotation of rotatable member (1220), the upper portion of each vacuum opening (1232) is generally shaped to form an arc or semi-circle relative to the upper portion of each adjacent vacuum opening (1232). As will be described in greater detail below, each vacuum opening (1232) is generally associated with a corresponding sample opening (1230, 1232). As a result, only a single vacuum opening (1232) is in communication with a vacuum source when the particular corresponding sample opening (1230, 1232) is in communication with the cutter of needle (22). As will also be described in greater detail below, this configuration generally promotes the flow of vacuum into a given vacuum opening (1234), into the inner chamber (and through cassette tray (510)) and out of a corresponding sample opening (1230, 1232).

Although not shown, it should be understood that like with manifold (640) described above, lower wall (1242) of each manifold (1240) includes a plurality of vacuum walls (not shown) that define a plurality of vacuum chambers (not shown). Like with vacuum walls (644) described above, each vacuum wall of each manifold (1240) extends upwardly from lower wall (1242) partially into the inner chamber. This upward extension both defines the vacuum chambers and provides support for cassette tray (510) when cassette tray (510) is inserted into manifold (1240). As also similarly described above with respect to vacuum chambers (645), each vacuum chamber of each manifold (1240) is in communication with a corresponding vacuum opening (1234) to communicate vacuum from probe assembly (20) and into cassette tray (510).

Rotatable member (1220) further comprises a keyed shaft (1228) extending distally from circular base (1222). Keyed shaft (1228) is generally configured to engage at least a portion of probe assembly (20) and/or holster assembly (30) to rotate rotatable member (1220) relative to probe assembly (20). Keyed shaft (1228) is substantially similar to a corresponding feature of tissue sample holder assembly (40) such that tissue sample holder assembly (1200) remains compatible with probe assembly (20) without modification. However, it should be understood that in some circumstances probe assembly (20) and/or holster assembly (30) may be operated using different algorithms specifically for tissue sample holder assembly (1200) to accommodate different rotational requirements associated with rotatable member (1220).

In an exemplary use tissue sample holder assembly (1200) is used as similarly described above with respect to tissue sample holder assembly (600). For instance, a cassette tray (510) is initially inserted into each manifold (1240) of rotatable member (1220). Although not shown, it should be understood that at this stage tissue sample holder assembly (1200) is generally already coupled to probe assembly (20) via coupler (1210) in lieu of tissue sample holder assembly (40).

With a cassette tray (510) disposed within each manifold (1240), vacuum enters manifold (1240) through a given vacuum opening (1234) of a selected manifold (1240). Vacuum opening (1234) is aligned with probe assembly (20) such that vacuum opening (1234) in communication with a corresponding vacuum port of probe assembly (20). Next, vacuum travels through the corresponding vacuum chamber of the selected manifold (1240) and upwardly through vents (526) of cassette tray (510). Vacuum then travels through a corresponding sample chamber (523) of cassette tray (510) and out of the selected manifold (1240) either through an upper sample opening (1230) or lower sample opening (1232), depending on which sample opening (1230, 1232) is positioned into communication with the cutter of needle (22). Vacuum is then used to pull a tissue sample through the cutter of needle (22) and into the corresponding sample chamber (526) of cassette tray (510).

As similarly described above with respect to tissue sample holder assembly (600), rotatable member (1220) is generally rotated through a progression to successively fill each cassette tray (510) disposed within each manifold (1240) with a plurality of tissue samples. In particular, rotatable member (1220) is initially rotated for collection of tissue samples in a first selected manifold (1240). This, rotatable member (1220) is initially rotates so that a selected lower sample opening (1232) and a selected vacuum opening (1234) of the first selected manifold (1240) is positioned at a twelve o'clock position. Although not shown, it should be understood that probe assembly (20) defines two ports that are also at the twelve o'clock position. Each of the two ports corresponds to either communication with the cutter of needle (22) or a vacuum source. Accordingly, when the selected lower sample opening (1232) is in the twelve o'clock position, the selected lower sample opening (1232) is in communication with the cutter of needle (22). Correspondingly, when the selected vacuum opening (1234) is in the twelve o'clock position, the selected vacuum opening (1234) is in communication with a vacuum source associated with probe assembly (20). Once in this position, the selected lower sample opening (1232) and the selected vacuum opening (1234) of the first selected manifold (1240) are used to collect a tissue sample in accordance with the sample collection operation described above.

Once a sample is received within sample chamber (523) of cassette tray (510), rotatable member (1220) is rotated to index the first selected manifold (1240) so the next successive sample opening (1230, 1232) and vacuum opening (1234) is positioned into the twelve o'clock position described above. In the present use, this rotation results in a selected upper sample opening (1230) and another selected vacuum opening (1234) being in communication with corresponding features of probe assembly (20) as similarly described above. In this position, another tissue sample may be collected in the sample chamber (523) of cassette tray (510) corresponding to the selected upper sample opening (1230).

Next, rotatable member (1220) is again rotated to move the first selected manifold (1240) to position another selected upper sample opening (1230) and another vacuum opening (1234) into the twelve o'clock position. Once at the twelve o'clock position, the next selected upper sample opening (1230) and the next selected vacuum opening (1234) can be used to collect a tissue sample into the sample chamber (523) of cassette tray (510) corresponding to the next selected upper sample opening (1230).

Finally, rotatable member (1220) is next rotated to move the first selected manifold (1240) to position another selected lower sample opening (1232) and another vacuum opening (1234) into the twelve o'clock position. Once at the twelve o'clock position, the next selected lower sample opening (1232) and the next selected vacuum opening (1234) can be used to collect a tissue sample into the sample chamber (523) of cassette tray (510) corresponding to the next selected lower sample opening (1232). This final progression will result in the cassette tray (510) associated with the first selected manifold (1240) being completely full.

Once the first selected manifold (1240) is completely full or otherwise filled to a desired level, rotatable member (1220) is rotated further to index a second selected manifold (1240) with probe assembly (20). The tissue collection procedure described above is then repeated to collect tissue samples within the cassette tray (510) associated with the second selected manifold (1240).

Once sample chambers (523) of each cassette tray (510) are filled with a tissue sample as desired by an operator, an operator may next desire to perform certain analysis on the collected tissue samples. To perform analysis on the collected tissue samples, an operator first removes each cassette tray (510) from each manifold (1240) of rotatable member (1220). At this stage, cassette tray (510) may be subjected to the same post biopsy procedure operations described above.

B. Exemplary Alternative Tissue Sample Holder Assembly with Tri-Manifold

Figure 40:
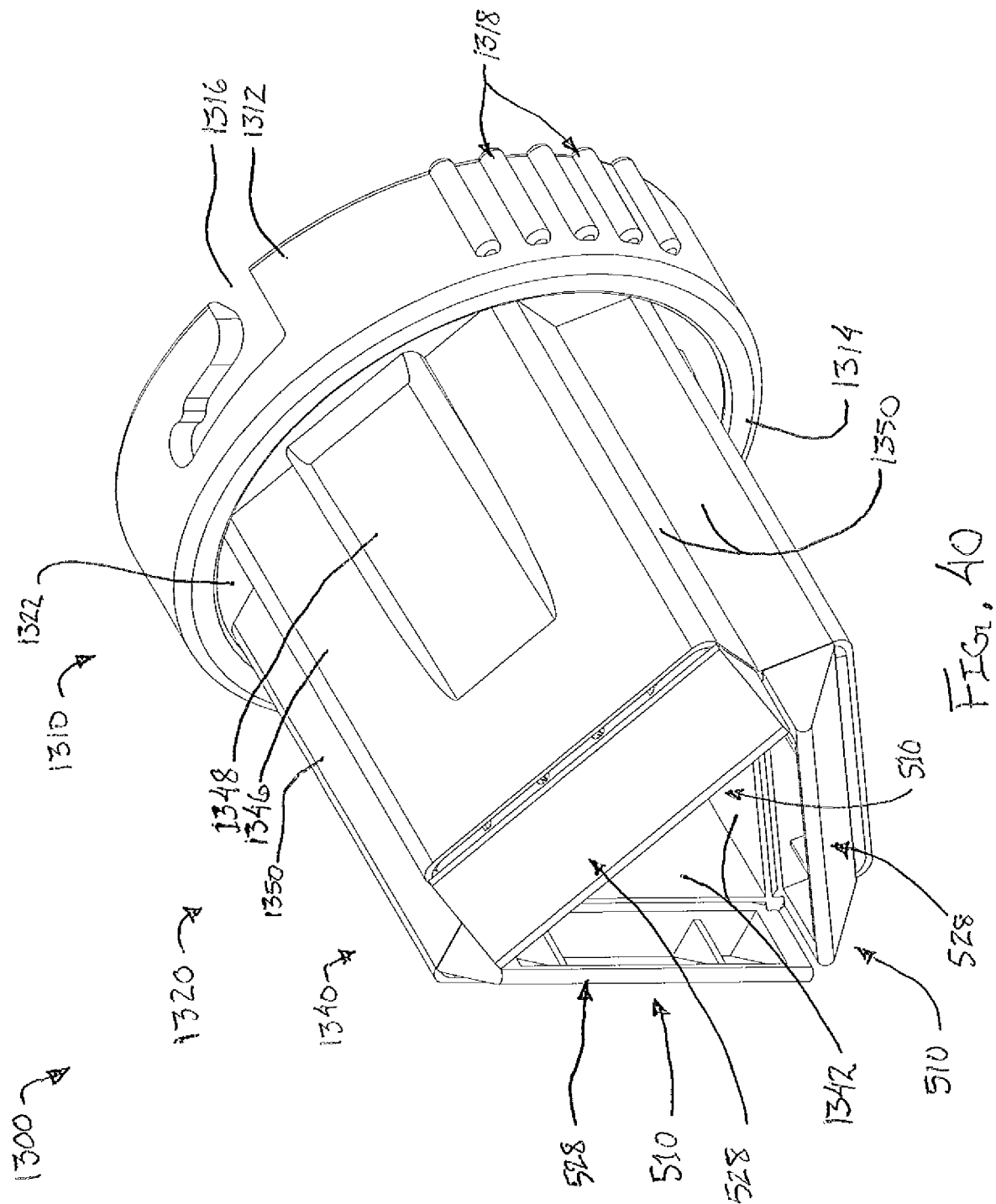
FIG. 40 depicts a perspective view of still another exemplary alternative tissue sample holder assembly that may be readily incorporated into the biopsy device of FIG. 1 in lieu of the tissue sample holder assembly of FIG. 2.
Figure 41:
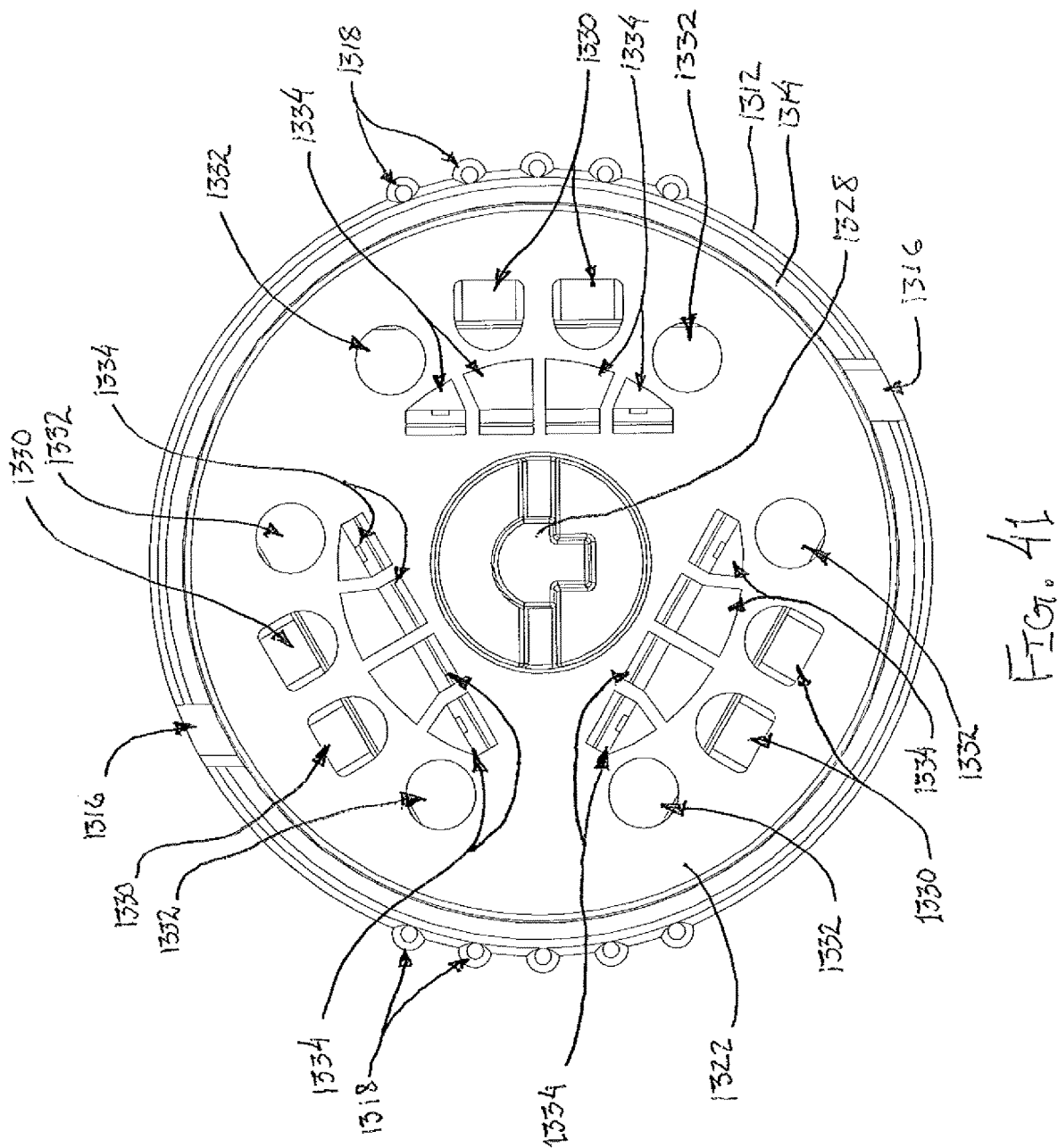
FIG. 41 depicts a front elevational view of the tissue sample holder assembly of FIG. 40.

FIGS. 40 and 41 show an exemplary alternative tissue sample holder assembly (1300) that can be used in connection with cassette assembly (500) described above. Unless otherwise described herein, tissue sample holder assembly (1300) is substantially similar to tissue sample holder assembly (600) described above. For instance, like with tissue sample holder assembly (600), tissue sample holder assembly (1300) of the present example comprises a coupler (1310), and a rotatable member (1320). Coupler (1310) comprises a generally ring-shaped body (1312) with a sealing lip (1314), a pair of bayonet connectors (1316), and a plurality of grips (1318). Sealing lip (1314) is configured to engage at least a portion of rotatable member (1320) to seal rotatable member (1320) relative to coupler (1310) and probe assembly (20). In addition, sealing lip (1314) is configured to permit rotation of rotatable member (1320) relative to coupler (1310) and probe assembly (20). As will be described in greater detail below, this rotation permits one or more cassette trays (510) to be moved relative to probe assembly (20) so that a single tissue sample can be collected within each sample chamber (523) of each cassette tray (510).

Bayonet connectors (1316) are configured to receive a pair of bayonet pins (not shown) of probe assembly (20) to selectively couple coupler (1310) to probe assembly (20). Thus, bayonet connectors (1316) and the bayonet pins of probe assembly (20) form a standard bayonet coupling assembly to selectively secure coupler (1310) to probe assembly (20). In this configuration, ring-shaped body (1312) is generally rotatable relative to probe assembly (20) to lock and unlock coupler (1310) relative to probe assembly (20). To assist an operator with rotation of ring-shaped body (1312), coupler (1310) includes grips (1318) to enhance grip of ring-shaped body (1312) during locking and unlocking. Although the present example uses a bayonet coupling to secure coupler (1310) to probe assembly (20), it should be understood that in other examples various alternative coupling features can be used as will be apparent to those of ordinary skill in the art in view of the teachings herein.

Rotatable member (1320) is generally configured to receive two cassette trays (510) and position each cassette tray (510) relative to probe assembly (20) to thereby collect a tissue sample within each sample chamber (523) of each cassette tray (510). Except where as otherwise noted herein, rotatable member (1320) is substantially the same as rotatable member (620) described above. For instance, like with rotatable member (620) described above, rotatable member (1320) comprises a circular base (1322), and at least one manifold (1340) protruding from base (1322). The circular shape of base (1320) is generally configured for receipt within coupler (1310) such that at least a portion of base (1320) abuts sealing lip (1314) of coupler (1310).

Unlike rotatable member (620) described above, rotatable member (1320) of the present example includes three substantially similar manifolds (1340) extending proximally from base (1322). Manifolds (1322) are collectively arranged in a triangular configuration. In this configuration, the tissue collection capacity of tissue sample holder assembly (1300) is increased, while still preserving the functionality of tissue sample holder assembly (1300) to successively collect tissue samples within one or more cassette trays (510).

Each manifold (1340) is substantially the same as manifold (640) described above, except where otherwise explicitly noted herein. For instance, like with manifold (640), each manifold (1340) of the present example comprises a lower wall (1342), an upper wall (1346), and a pair of sidewalls (1350) extending between the lower wall (1342) and the upper wall (1346). Walls (1342, 1346, 1350) together define a generally rectangular box that is configured to receive cassette tray (510). Walls (1342, 1346, 1350) further define an inner chamber (not shown) that is large enough to accommodate cassette tray (510), while also providing fluid flow through manifold (1340).

Upper wall (1346) of each manifold (1340) includes a raised connector (1348) that is generally hollow such that a portion of the inner chamber is defined by raised connector (1348). As will be described in greater detail below, raised connector (1348) is generally configured to receive tissue samples axially relative to the longitudinal axis of rotatable member (1320) and direct tissue samples downwardly into cassette tray (510). Although raised connector (1348) is shown as a single discrete part that is integral with upper wall (1346), it should be understood that in other examples raised connector (1348) can be a separate part, formed of more than one part, or a combination of both.

As best seen in FIG. 41, the inner chamber of each manifold (1340) communicates with probe assembly (20) via a plurality of openings (1330, 1332, 1334) defined by and extending axially through circular base (1322). In particular, circular base (1322) defines four sample openings (1330, 1332) and four vacuum openings (1334). Of the four sample openings (1330, 1332), circular base (1322) defines two upper sample openings (1330) and two lower sample openings (1332). In this configuration, upper sample openings (1330) communicate with the portion of the inner chamber of each manifold (1340) that is defined by raised connector (1348), while lower sample openings (1332) are in communication with the portion of the inner chamber that is defined by walls (1342, 1346, 1350). As described above, rotatable member (1320) is generally rotatable to place a particular sample chamber (523) of cassette tray (510) into communication with the cutter of needle (22). However, since cassette tray (510) is generally of a flat configuration, upper sample openings (1330) are positioned above lower sample openings (1332) to accommodate both the rotation of rotatable member (1320) and the flat configuration of cassette tray (510).

In contrast to sample openings (1330, 1332), vacuum openings (1334) are generally aligned along a common axis. However, to accommodate rotation of rotatable member (1320), the upper portion of each vacuum opening (1332) is generally shaped to form an arc or semi-circle relative to the upper portion of each adjacent vacuum opening (1332). As will be described in greater detail below, each vacuum opening (1332) is generally associated with a corresponding sample opening (1330, 1332). As a result, only a single vacuum opening (1332) is in communication with a vacuum source when the particular corresponding sample opening (1330, 1332) is in communication with the cutter of needle (22). As will also be described in greater detail below, this configuration generally promotes the flow of vacuum into a given vacuum opening (1334), into the inner chamber (and through cassette tray (510)) and out of a corresponding sample opening (1330, 1332).

Although not shown, it should be understood that like with manifold (640) described above, lower wall (1342) of each manifold (1340) includes a plurality of vacuum walls (not shown) that define a plurality of vacuum chambers (not shown). Like with vacuum walls (644) described above, each vacuum wall of each manifold (1340) extends upwardly from lower wall (1342) partially into the inner chamber. This upward extension both defines the vacuum chambers and provides support for cassette tray (510) when cassette tray (510) is inserted into manifold (1340). As also similarly described above with respect to vacuum chambers (645), each vacuum chamber of each manifold (1340) is in communication with a corresponding vacuum opening (1334) to communicate vacuum from probe assembly (20) and into cassette tray (510).

Rotatable member (1320) further comprises a keyed shaft (1328) extending distally from circular base (1322). Keyed shaft (1328) is generally configured to engage at least a portion of probe assembly (20) and/or holster assembly (30) to rotate rotatable member (1320) relative to probe assembly (20). Keyed shaft (1328) is substantially similar to a corresponding feature of tissue sample holder assembly (40) such that tissue sample holder assembly (1300) remains compatible with probe assembly (20) without modification. However, it should be understood that in some circumstances probe assembly (20) and/or holster assembly (30) may be operated using different algorithms specifically for tissue sample holder assembly (1300) to accommodate different rotational requirements associated with rotatable member (1320).

In an exemplary use tissue sample holder assembly (1300) is used as similarly described above with respect to tissue sample holder assembly (600). For instance, a cassette tray (510) is initially inserted into each manifold (1340) of rotatable member (1320). Although not shown, it should be understood that at this stage tissue sample holder assembly (1300) is generally already coupled to probe assembly (20) via coupler (1310) in lieu of tissue sample holder assembly (40).

With a cassette tray (510) disposed within each manifold (1340), vacuum enters manifold (1340) through a given vacuum opening (1334) of a selected manifold (1340). Vacuum opening (1334) is aligned with probe assembly (20) such that vacuum opening (1334) in communication with a corresponding vacuum port of probe assembly (20). Next, vacuum travels through the corresponding vacuum chamber of the selected manifold (1340) and upwardly through vents (526) of cassette tray (510). Vacuum then travels through a corresponding sample chamber (523) of cassette tray (510) and out of the selected manifold (1340) either through an upper sample opening (1330) or lower sample opening (1332), depending on which sample opening (1330, 1332) is positioned into communication with the cutter of needle (22). Vacuum is then used to pull a tissue sample through the cutter of needle (22) and into the corresponding sample chamber (526) of cassette tray (510).

As similarly described above with respect to tissue sample holder assembly (600), rotatable member (1320) is generally rotated through a progression to successively fill each cassette tray (510) disposed within each manifold (1340) with a plurality of tissue samples. In particular, rotatable member (1320) is initially rotated for collection of tissue samples in a first selected manifold (1340). This, rotatable member (1320) is initially rotates so that a selected lower sample opening (1332) and a selected vacuum opening (1334) of the first selected manifold (1340) is positioned at a twelve o'clock position. Although not shown, it should be understood that probe assembly (20) defines two ports that are also at the twelve o'clock position. Each of the two ports corresponds to either communication with the cutter of needle (22) or a vacuum source. Accordingly, when the selected lower sample opening (1332) is in the twelve o'clock position, the selected lower sample opening (1332) is in communication with the cutter of needle (22). Correspondingly, when the selected vacuum opening (1334) is in the twelve o'clock position, the selected vacuum opening (1334) is in communication with a vacuum source associated with probe assembly (20). Once in this position, the selected lower sample opening (1332) and the selected vacuum opening (1334) of the first selected manifold (1340) are used to collect a tissue sample in accordance with the sample collection operation described above.

Once a sample is received within sample chamber (523) of cassette tray (510), rotatable member (1320) is rotated to index the first selected manifold (1340) so the next successive sample opening (1330, 1332) and vacuum opening (1334) is positioned into the twelve o'clock position described above. In the present use, this rotation results in a selected upper sample opening (1330) and another selected vacuum opening (1334) being in communication with corresponding features of probe assembly (20) as similarly described above. In this position, another tissue sample may be collected in the sample chamber (523) of cassette tray (510) corresponding to the selected upper sample opening (1330).

Next, rotatable member (1320) is again rotated to move the first selected manifold (1340) to position another selected upper sample opening (1330) and another vacuum opening (1334) into the twelve o'clock position. Once at the twelve o'clock position, the next selected upper sample opening (1330) and the next selected vacuum opening (1334) can be used to collect a tissue sample into the sample chamber (523) of cassette tray (510) corresponding to the next selected upper sample opening (1330).

Finally, rotatable member (1320) is next rotated to move the first selected manifold (1340) to position another selected lower sample opening (1332) and another vacuum opening (1334) into the twelve o'clock position. Once at the twelve o'clock position, the next selected lower sample opening (1332) and the next selected vacuum opening (1334) can be used to collect a tissue sample into the sample chamber (523) of cassette tray (510) corresponding to the next selected lower sample opening (1332). This final progression will result in the cassette tray (510) associated with the first selected manifold (1340) being completely full.

Once the first selected manifold (1340) is completely full or otherwise filled to a desired level, rotatable member (1320) is rotated further to index a second selected manifold (1340) with probe assembly (20). The tissue collection procedure described above is then repeated to collect tissue samples within the cassette tray (510) associated with the second selected manifold (1340).

Once the second selected manifold (1340) is completely full or otherwise filled to a desired level, rotatable member (1320) is rotated further to index a third selected manifold (1340) with probe assembly (20). The tissue collection procedure described above is then repeated to collect tissue samples within the cassette tray (510) associated with the third selected manifold (1340).

Once sample chambers (523) of each cassette tray (510) are filled with a tissue sample as desired by an operator, an operator may next desire to perform certain analysis on the collected tissue samples. To perform analysis on the collected tissue samples, an operator first removes each cassette tray (510) from each manifold (1340) of rotatable member (1320). At this stage, cassette tray (510) may be subjected to the same post biopsy procedure operations described above.

VI. Exemplary Alternative Tissue Sample Holder Assembly

In some instances, it may be desirable to combine elements of tissue sample holder assembly (40) and tissue sample holder assembly (600) described above into a single alternative tissue sample holder assembly. For instance, tissue sample holder assembly (40) may be desirable because rotatable member (44) can be rotated in direct correspondence with needle (22) to provide a sample tracking feature. In such examples, a tissue sample is deposited into an individual tissue sample strip (110) at each clock position. Thus, each individual tissue sample strip (110) can correspond to a discrete sample collection position within a patient. Based on this, an operator can identify the sample location of a given tissue sample after the biopsy procedure based on the particular tissue sample strip (110) that the particular tissue sample is contained within.

By contrast, rotatable member (620) of tissue sample holder assembly (600) does not collect tissue samples at each clock position around the circumference of rotatable member (620). Because of this, it may be more challenging for an operator to track the tissue collection position for each tissue sample collected using tissue sample holder assembly (600). However, tissue sample holder assembly (600) may still be desirable in some circumstances because tissue sample holder assembly (600) is compatible with components such as cassette tray (510) that can be used through an entire biopsy sampling and analysis workflow.

In view of the unique advantages of both tissue sample holder assembly (40) and tissue sample holder assembly (600), it may be desirable to use a tissue sample holder assembly that combines elements of both components to achieve both benefits while eliminating some drawbacks. Although certain discrete alternative tissue sample holder assemblies are described below, it should be understood that various features of such tissue sample holder assemblies may be readily combined with other components described herein. Moreover, other modifications may be made as will be apparent to those of ordinary skill in the art in view of the teachings herein.

Figure 42:
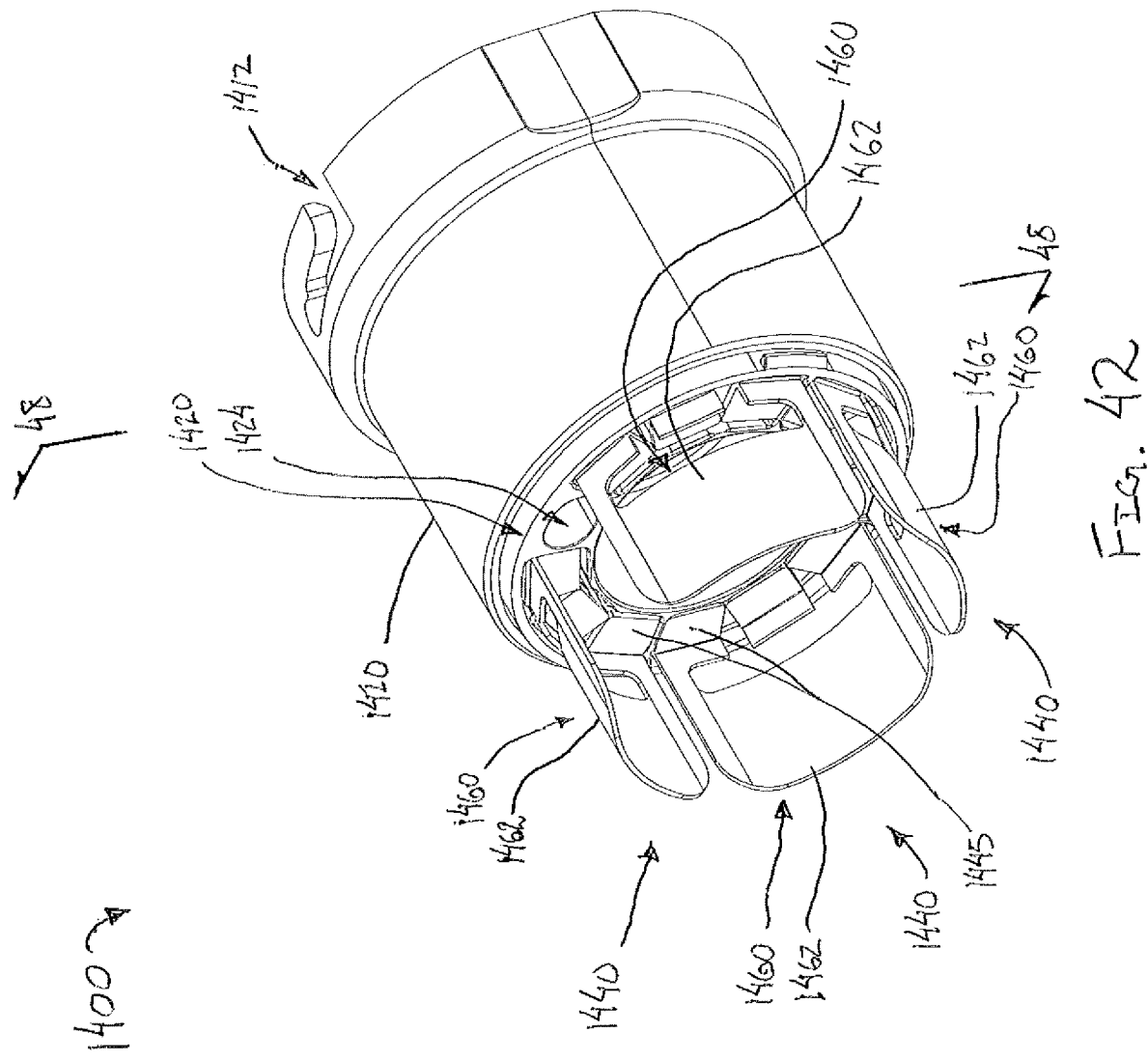
FIG. 42 depicts a perspective view of yet another exemplary alternative tissue sample holder assembly that may be readily incorporated into the biopsy device of FIG. 1 in lieu of the tissue sample holder assembly of FIG. 2.
Figure 43:
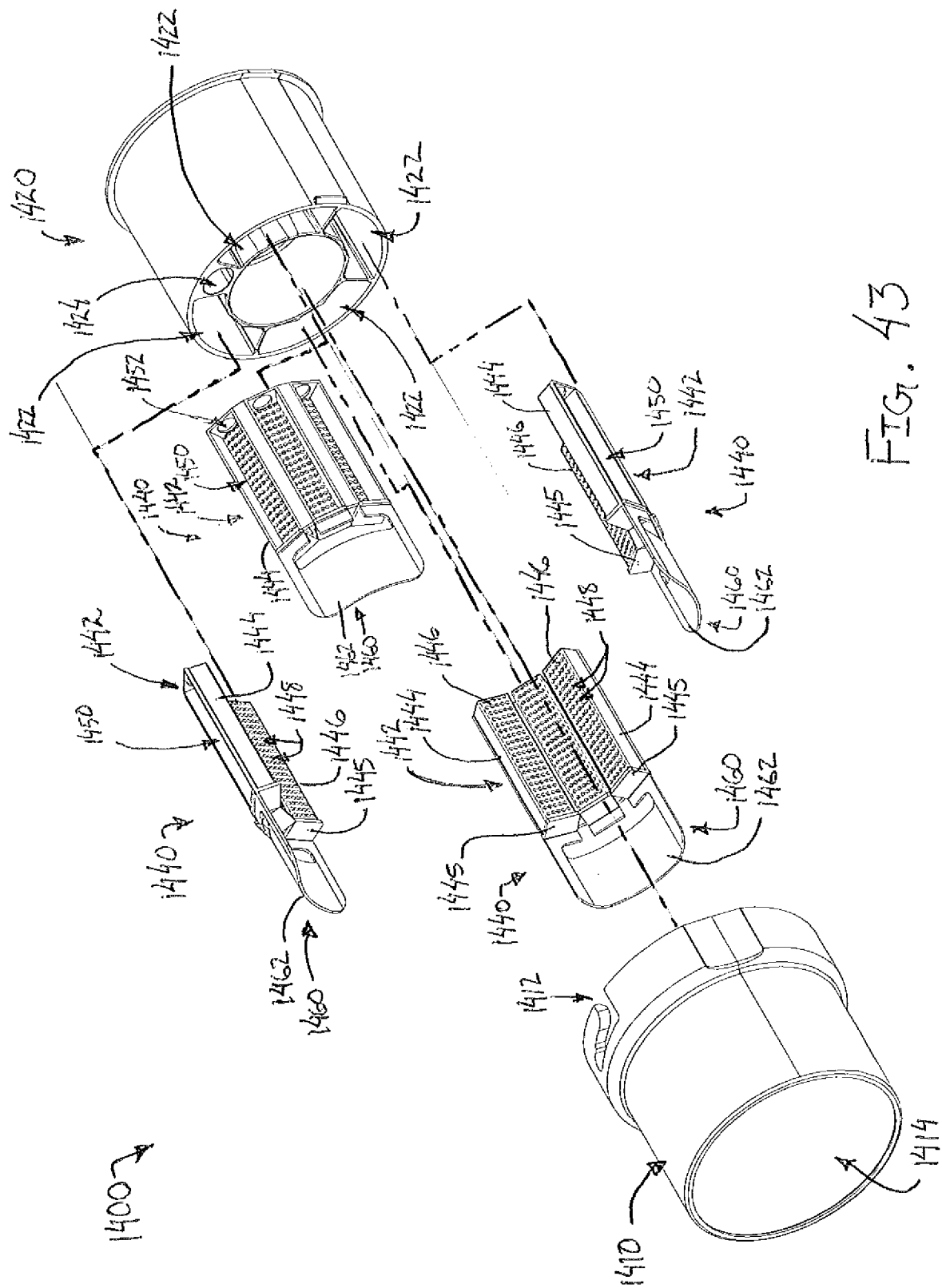
FIG. 43 depicts a perspective exploded view of the tissue sample holder assembly of FIG. 42.
Figure 44:
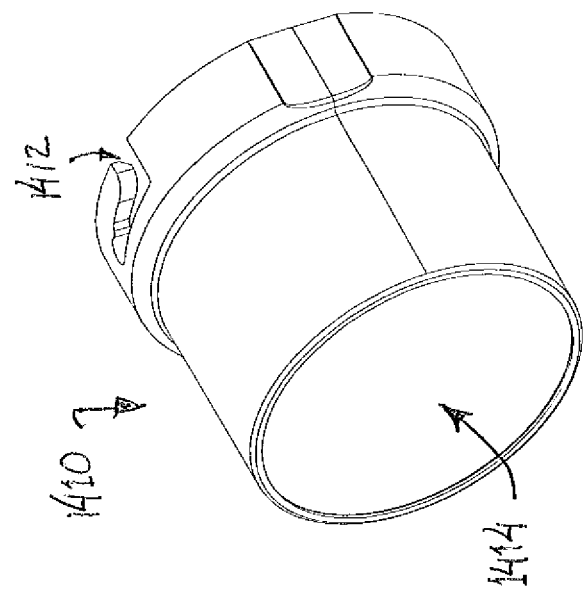
FIG. 44 depicts a perspective view of an outer cover of the tissue sample holder assembly of FIG. 42.

FIGS. 42 and 43 show an exemplary alternative tissue sample holder assembly (1400) that is similar to tissue sample holder assembly (40) described above. For instance, like with tissue sample holder assembly (40), tissue sample holder assembly (1400) of the present example comprises an outer cover (1410) that is configured to be removably coupled with probe assembly (20). As best seen in FIG. 44, outer cover (1410) generally defines a hollow cylindrical shape, which defines a cover chamber (1414). To couple outer cover (1410) to probe assembly (20), outer cover (1410) includes a pair of bayonet fittings (1412) that may receive corresponding bayonet posts (not shown) of probe assembly (20).

Figure 45:
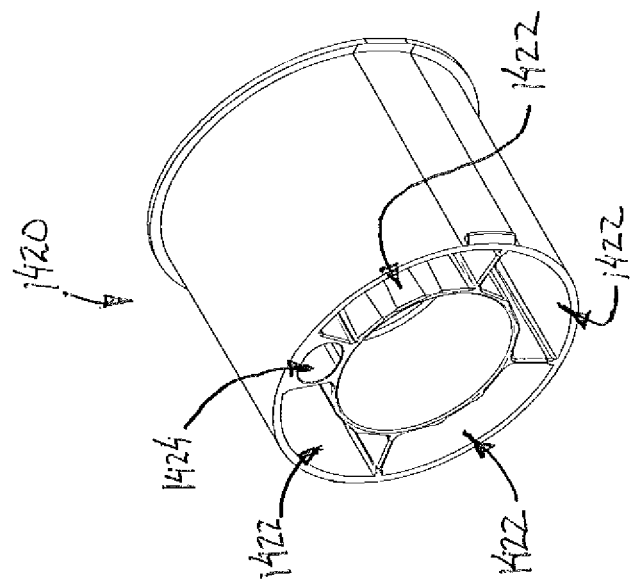
FIG. 45 depicts a perspective view of a rotatable member of the tissue sample holder assembly of FIG. 42.

Like with tissue sample holder assembly (40), tissue sample holder assembly (1400) of the present example further comprises a rotatable member (1420) that is similar to rotatable member (44) described above. Rotatable member (1420) is rotatably positioned within cover chamber (1414) cover (1410). As best seen in FIG. 45, rotatable member (1420) defines an angularly spaced array of strip receiving chambers (1422) and a plug chamber (1424), such that chambers (1422, 1424) together an annular arrangement. However, unlike rotatable member (44) described above, rotatable member (1420) of the present example includes four strip receiving chambers (1422) as opposed to twelve with rotatable member (44). As will be described in greater detail below, each strip receiving chamber (1422) is generally configured to receive a plurality of structures similar to strips (110) described above rather than a single structure similar to strips (110).

Rotatable member (1420) is rotatable relative to probe assembly (20) to selectively index chambers (1422, 1424) relative to the cutter. In some versions, drive components in holster assembly (30) drive rotation of rotatable member (1420). In some other versions, rotatable member (1420) is driven manually by the operator manually grasping some portion of tissue sample holder assembly (40).

Returning to FIG. 43, tissue sample holder assembly (1400) further includes a plurality of tissue sample trays (1440). Each tissue sample tray (1440) comprises a set of distally projecting tissue sample strips (1442). In the present configuration, each tissue sample tray (1440) includes three tissue sample strips (1442). Unlike tissue sample strips (110), which are described as being individually insertable into strip receiving chamber (46), each group of three tissue sample strip (1442) is configured for removable insertion into a corresponding strip receiving chamber (1422) of rotatable member (1420). Thus, each strip receiving chamber (1422) defined by rotatable member (1420) of the present example receives three tissue sample strips (1442).

Figure 46:
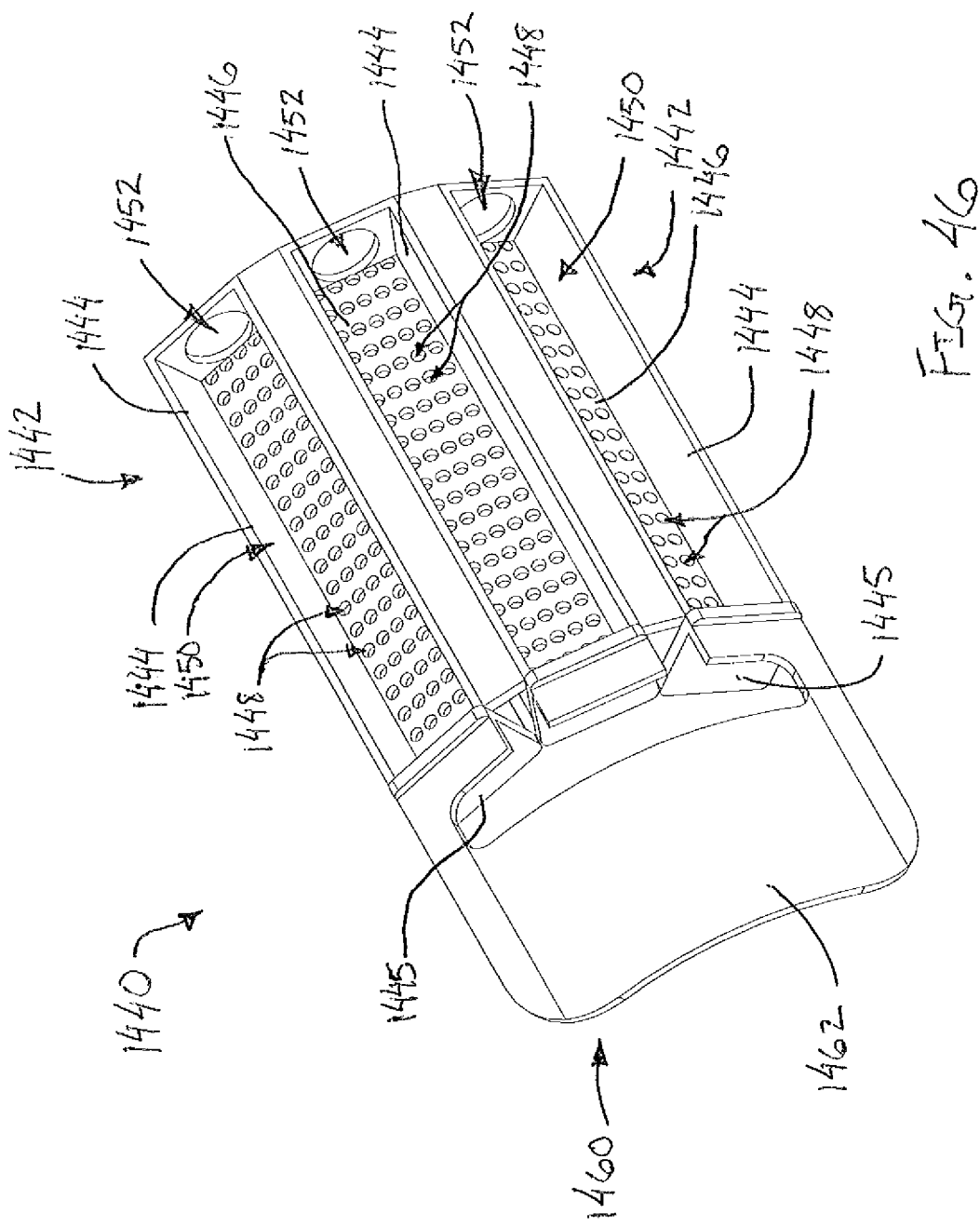
FIG. 46 depicts a perspective view of a tissue sample tray of the tissue sample holder assembly of FIG. 42, the tissue sample tray in an arcuate configuration.

As best seen in FIG. 46, each tissue sample strip (1442) comprises a set of strip sidewalls (1444) joined by a floor (1446) and terminating at a proximal wall (1445). Strip sidewalls (1444) and floor (1446) cooperate to define a tissue receiving chamber (1450), such that each tissue sample strip (1442) is configured to receive a corresponding tissue sample. Floor (1446) defines a plurality of openings (1448) that are sized to provide communication of suction and fluids therethrough, while preventing communication of tissue samples therethrough. It should be understood that suction may be communicated through strip receiving chambers (1422) to reach tissue receiving chambers (1450) via openings (1448). Each tissue sample strip (1442) of the present example also includes a distal opening (1452). Distal opening (1452) is sized and configured to enable a severed tissue sample to pass therethrough in order for the tissue sample to be deposited into tissue receiving chamber (120).

Each tissue sample tray (1440) further comprises a proximally projecting tab (1460) that defines a labeling portion (1462). Tab (1460) is configured to facilitate grasping of tissue sample tray (1440) by an operator. At least a portion of tab (1460) is attached to a proximal wall (1445) of at least one tissue sample strip (1442). In the present example, tab (1460) forms a curved configuration such that tab (1460) is connected to the proximal wall (1445) of each of the outer two tissue sample strips (1442). However, it should be understood that in other examples tab (1460) can be configured to connect to one tissue sample strip (1442) or all three tissue sample strips (1442).

Labeling portion (1462) is configured to receive a label, which may include certain procedure related information. As similarly described above, labeling portion (1462) may be configured to directly receive a pre-printed label such that the pre-printed label may be directly adhered to the surface of labeling portion (1462). Alternatively, a label may be directly printed on the surface of labeling portion (1462) by a label printer or etching machine. In still other examples, labeling portion (1462) may include an RFID tag or other electromagnetic storage medium to store procedure information directly within labeling portion (1462).

Tissue sample tray (1440) further includes a set of living hinges (1454) disposed between each tissue sample strip (1442). In the present configuration, tissue sample tray (1440) includes two living hinges (1454) extending from one tissue sample strip (1442) to another adjacent tissue sample strip (1442). It should be understood that in other examples this configuration can be varied depending on the particular number of tissue sample strips (1442) included within each tissue sample tray (1440).

Each living hinge (1454) is generally integral with a particular tissue sample strip (1442) that each living hinge (1454) is connected to. Living hinges (1454) enable tissue sample tray (1440) to transition between an arcuate or curved configuration shown in FIG. 46 and a flattened configuration shown in FIG. 47B. In the arcuate or curved configuration, tissue sample tray (1440) is configured to fit in rotatable member (1420). In the flattened configuration, tissue sample tray (1440) is configured to fit in covers (540, 1140) as will be described in greater detail below.

Figure 47A:
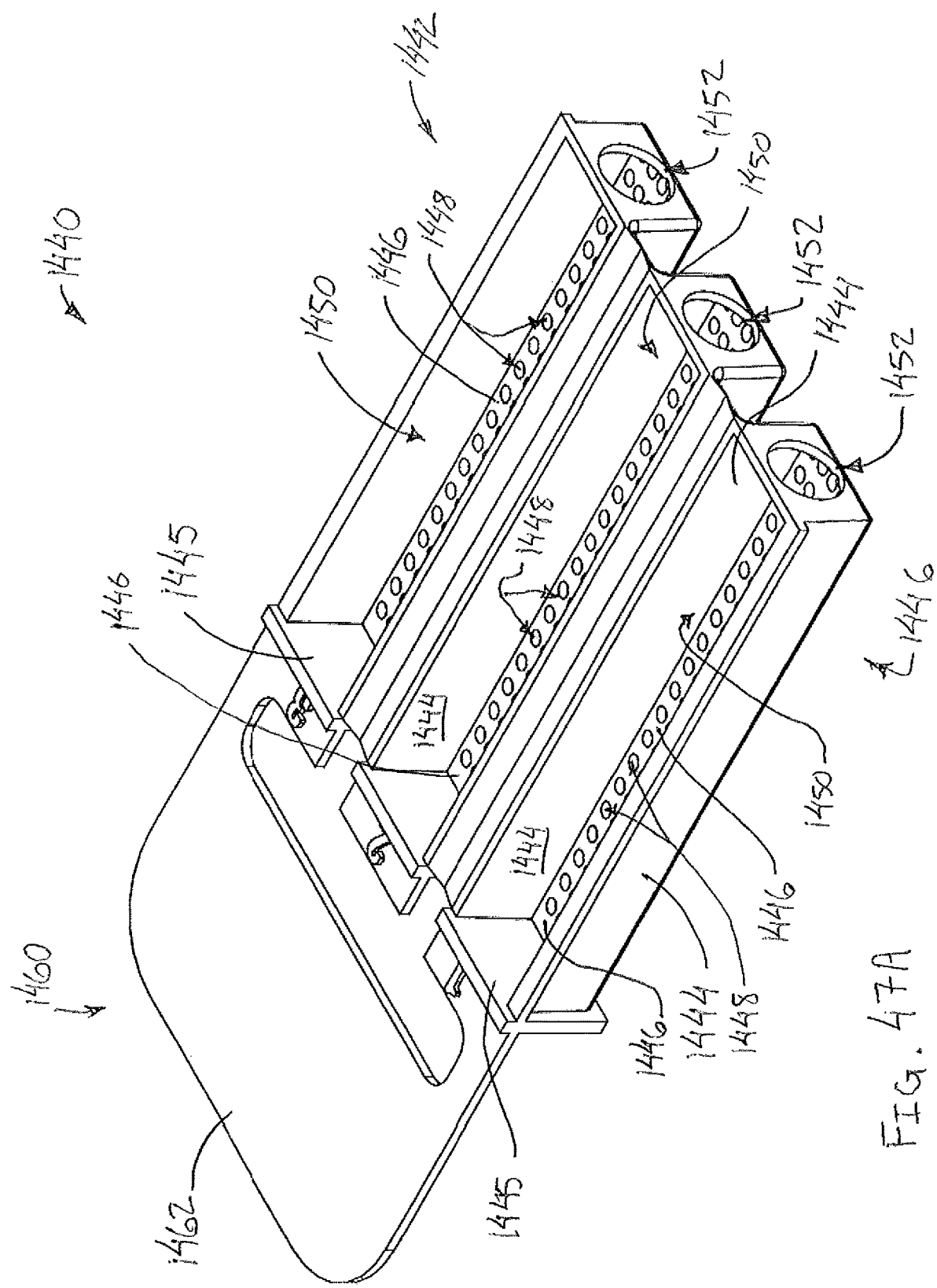
FIG. 47A depicts another perspective view of the tissue sample tray of FIG. 46, the tissue sample tray in a flat configuration.
Figure 47B:
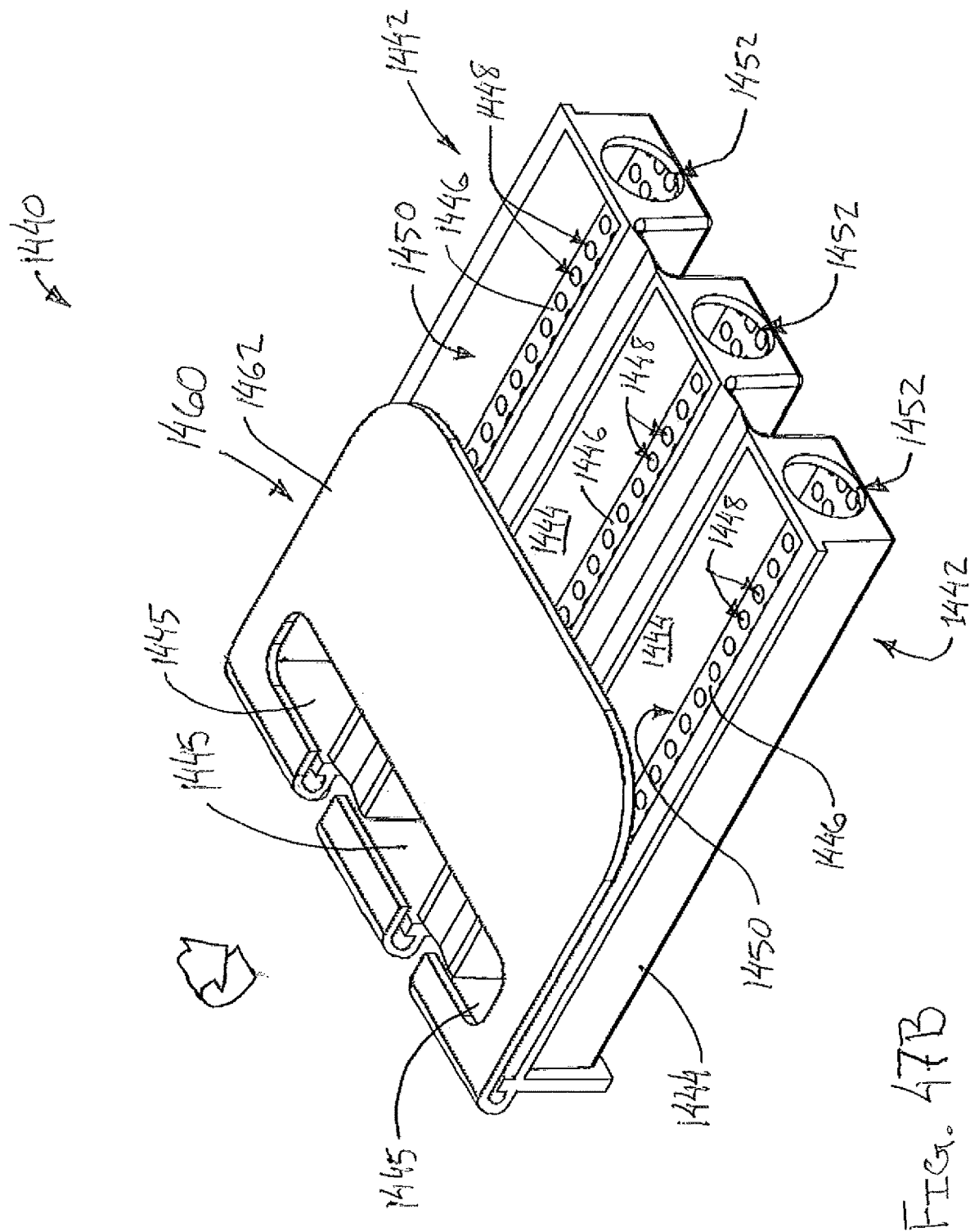
FIG. 47B depicts still another perspective view of the tissue sample tray of FIG. 46, the tissue sample tray in a stowed configuration.

As can be seen in FIG. 47B, when tissue sample tray (1440) is in the flatten configuration, tissue sample tray (1440) is further configured such that tab (1460) can be repositioned to lay flat over tissue sample strips (1442). As will be described in greater detail below, this configuration permits tab (1460) to be placed in a stowed position to generally reduce the footprint of tissue sample tray (1440) when tissue sample tray is disposed within covers (540, 1140). Although not shown, it should be understood that repositioning of tab (1460) can be accomplished in a variety of ways. For instance, in the present example tab (1460) is simply flexible so that it can easily bend in a variety of directions. Alternatively, in other examples tab (1460) can include a living hinge or other structures to promote bending of tab (1460) at specific points.

As noted above, rotatable member (1420) is rotatable relative to probe assembly (20) to selectively index strip receiving chambers (1422) relative to the cutter, to thereby selectively index tissue receiving chambers (1450) of tissue sample strips (1442) relative to the cutter. Rotatable member (1420) is also operable to index plug receiving chamber (1424) relative to the cutter. When rotatable member (1420) is angularly positioned to index plug receiving chamber (1424) relative to the cutter, a plug (not shown) may be removed from plug receiving chamber (1424) to enable insertion of a biopsy site marker applier instrument (or some other kind of instrument) through the cutter and needle assembly (22), thereby providing an access path to the biopsy site via lateral aperture (26). Otherwise, the plug may be left in plug receiving chamber (1424) during operation of biopsy device (10), thereby sealing plug receiving chamber (1424).

Figure 48:
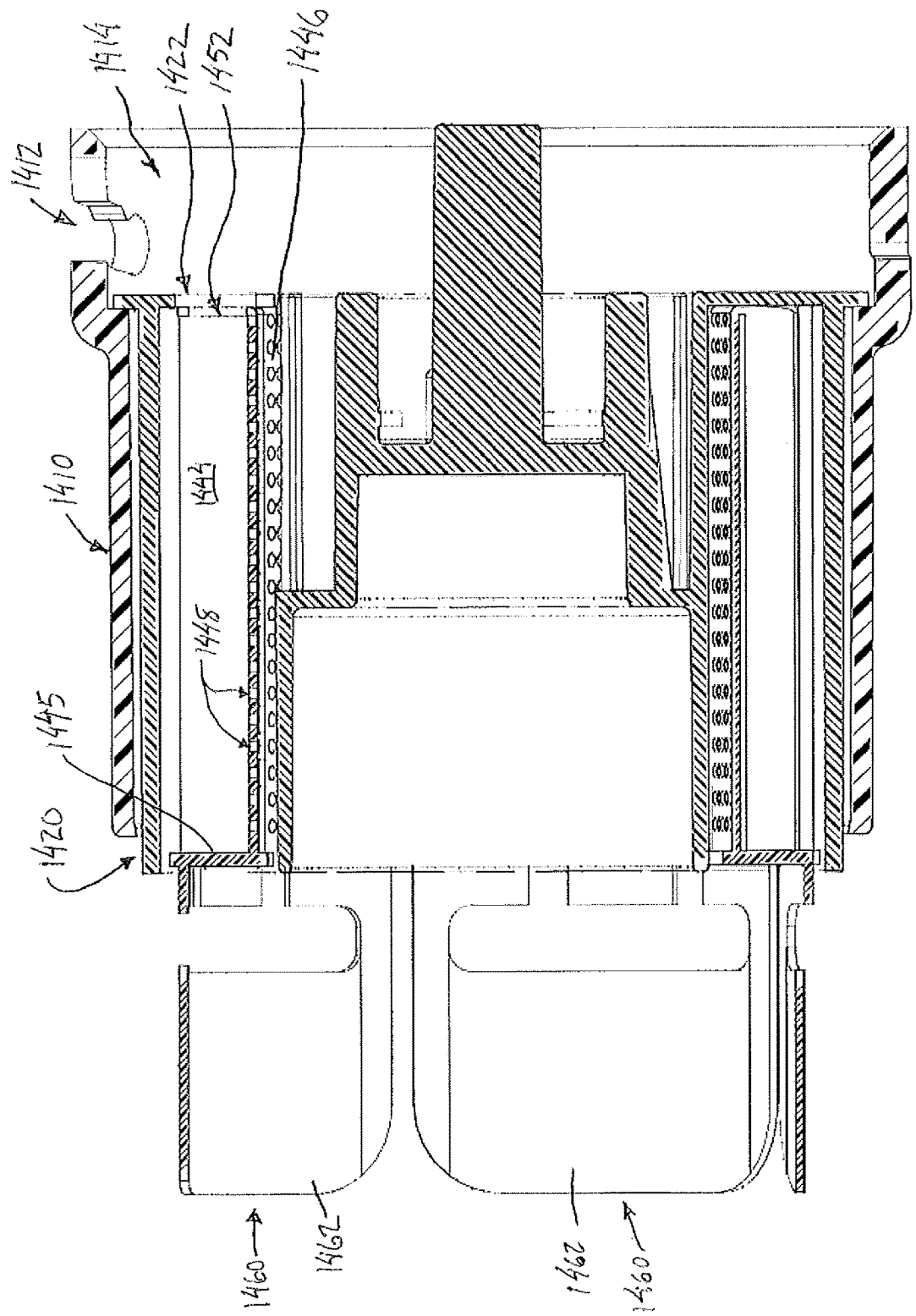
FIG. 48 depicts a side cross-sectional view of the tissue sample holder assembly of FIG. 42, the cross-section taken along line 48-48 of FIG. 42.

In an exemplary use, rotatable member (1420) is initially rotated to position a selected tissue sample strip (1442) into the twelve o'clock position relative to probe assembly (20) shown in FIG. 48. In this position, the corresponding tissue receiving chamber (1450) of the selected tissue sample strip (1442) is placed into communication with the cutter of needle (22). Accordingly, vacuum may be supplied to the distal end of rotatable member (1420). Vacuum may then enter rotatable member (1420) and pass through openings (1448) defined by floor (1446) of the selected tissue sample strip (1442). Vacuum can then pass through distal opening (1452) of the selected tissue sample strip (1442) and into the cutter of needle (22). This vacuum can then be applied to a severed tissue sample to transport the severed tissue sample through the cutter and into the tissue receiving chamber (1450) of the selected tissue sample strip (1442).

Once a tissue sample is collected, rotatable member (1420) can be rotated to a next successive tissue sample strip (1442). Another tissue sample can be collected as similarly described above. This process can then be repeated until all tissue sample strips (1442) of each tissue sample tray (1440) are filled. In some uses, this successive collection of tissue samples can be coordinated with rotation of rotatable member (1420) to permit tracking of the position within a patient where each tissue sample was taken. Alternatively, in some uses one or more tissue sample strips (1442) may be skipped such that not all tissue sample strips (1442) may be filled.

Regardless of particularly how tissue samples are collected, once a desired number of tissue samples have been collected by an operator, an operator may remove each tissue sample tray (1440) from rotatable member (1420) by pulling proximally on tab (1460). At this stage, if each tissue sample tray (1440) was not previously labeled before or during the biopsy procedure, each tissue sample tray (1440) can be labeled by applying a label or otherwise adding a label to labeling portion (1462).

Figure 49:
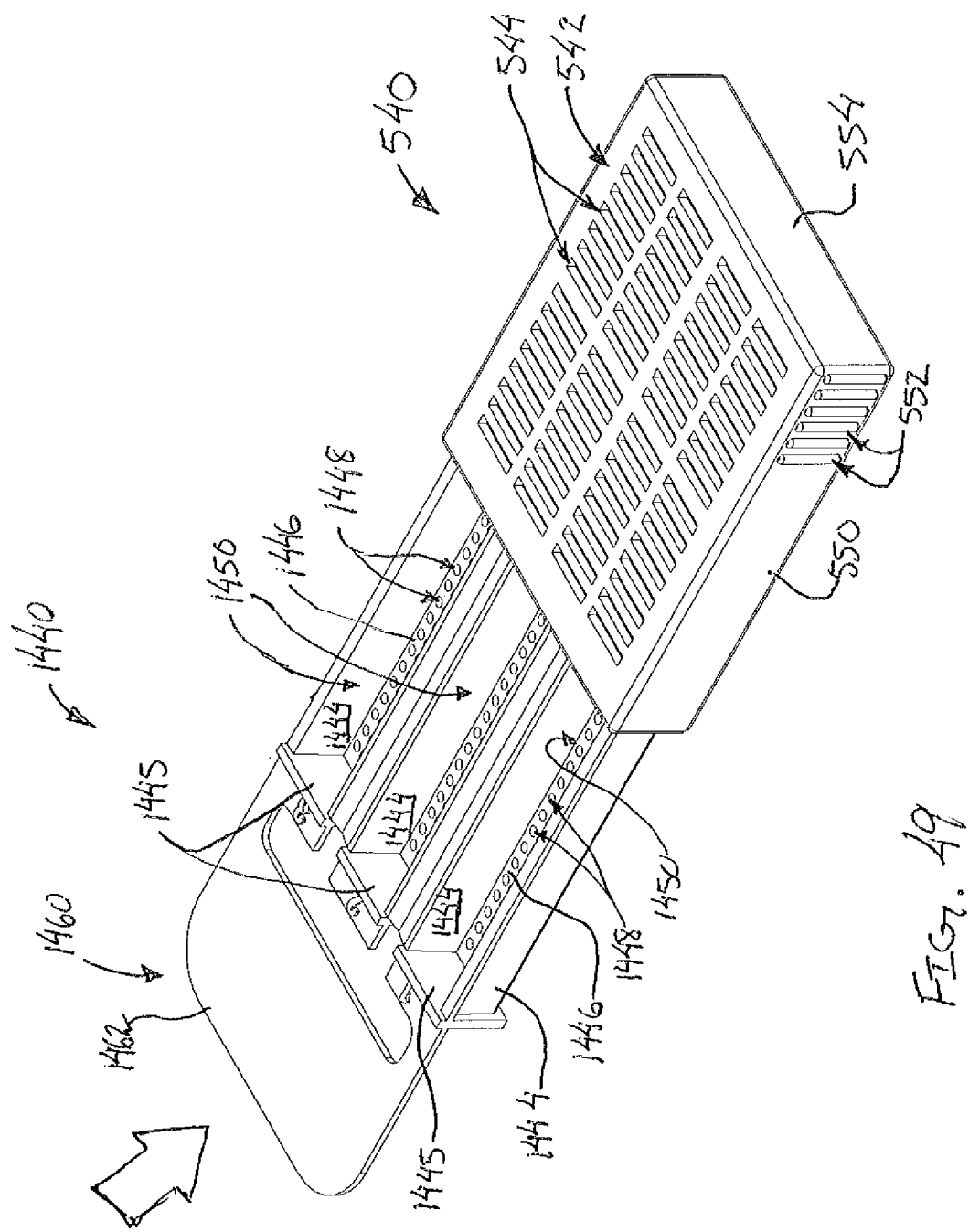
FIG. 49 depicts a perspective view of the tissue sample tray of FIG. 46 being inserted into the cover of FIG. 13.
Figure 50:
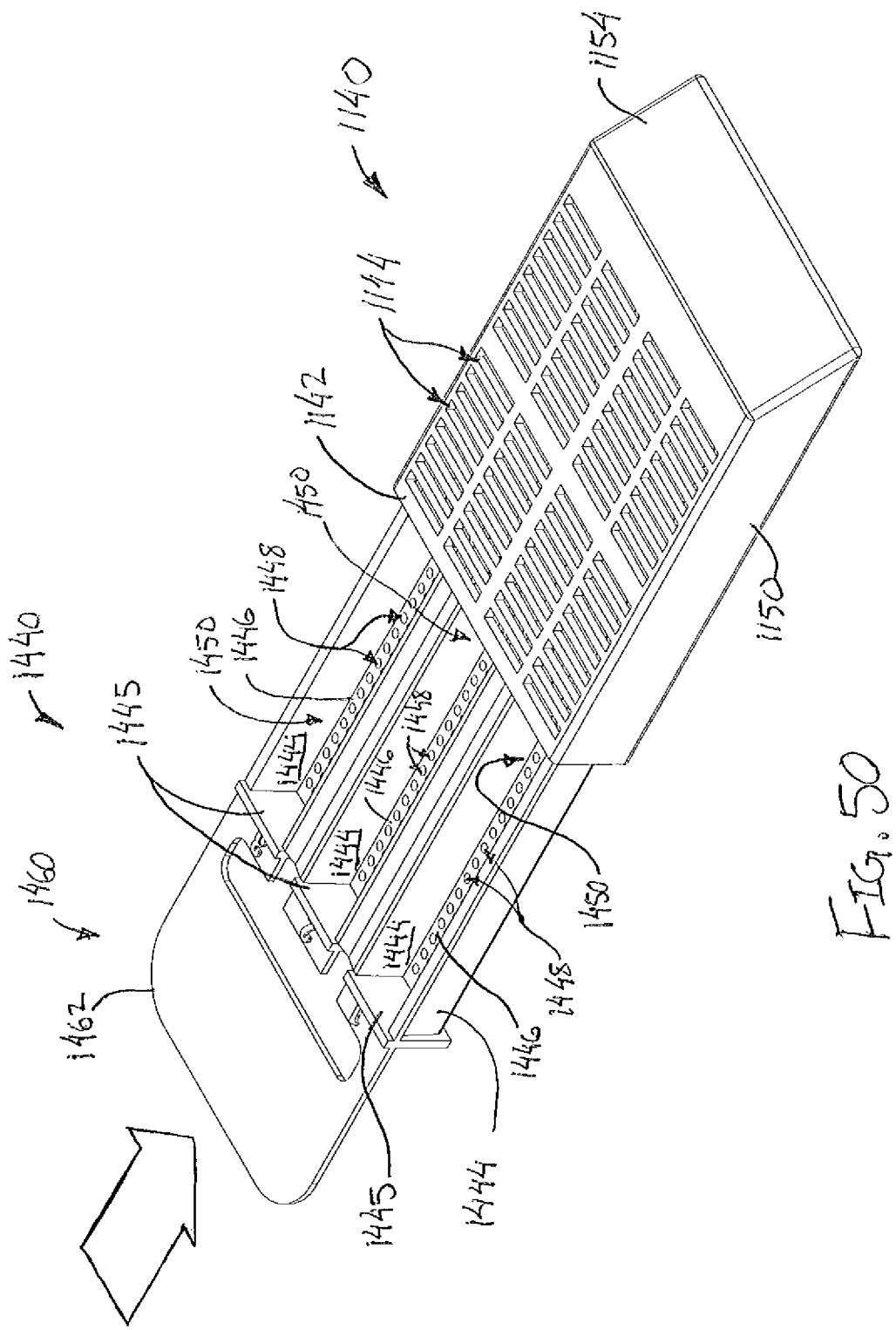
FIG. 50 depicts a perspective view of the tissue sample tray of FIG. 46 being inserted into the cover of FIG. 34.

After each tissue sample tray (1440) is removed from rotatable member (1420) and subjected to labeling, each tissue sample tray (1440) can be subjected to procedure room x-ray, if such analysis is desired. Once procedure room x-ray or any other preliminary analysis is complete, an operator may insert each tissue sample tray (1440) into cover (540) as shown in FIG. 49. Alternatively, an operator may insert each tissue sample tray (1440) into cover (1140) as shown in FIG. 50. It should be understood since cover (1140) also includes a labeling portion (1154), the use of cover (1140) shown in FIG. 50 may also include applying a label to labeling portion (1154).

Once each tissue sample tray (1440) is inserted into either cover (540) or cover (1140), the combination of tissue sample tray (1440) and cover (540) or cover (1140) can be transported to a pathology laboratory for further analysis. By way of example only, such further analysis may include the steps described above with respect to workflow (300) shown in FIG. 7.

VII. Exemplary Adaptor for Use with Cassette

In some circumstances, it may be desirable to use a cassette similar to cassette (200) described above exclusively during post-biopsy tissue sample analysis procedures. For instance, some clinicians may have established procedures with existing products and therefore may desire to maintain existing procedures with minimal alteration. Nonetheless, it may still be desirable to use such cassettes with components similar to tissue sample holder assembly (600) to fully integrate biopsy acquisition procedures with post-biopsy tissue sample analysis procedures. Accordingly, in some circumstances it may be desirable to use certain features in connection with components similar to tissue sample holder assembly (600) to adapt such components for use with cassettes similar to cassette (200). Although certain discrete components and configurations are described below, it should be understood that various features of such components may be readily combined with other components described herein. Moreover, other modifications may be made as will be apparent to those of ordinary skill in the art in view of the teachings herein.

Figure 51:
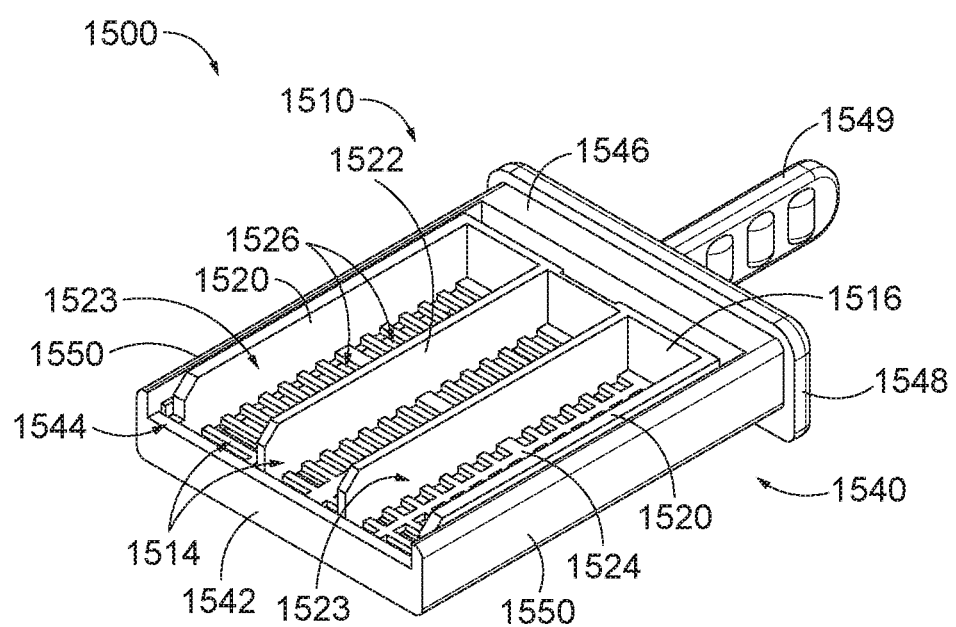
FIG. 51 depicts a perspective view of an exemplary cassette adaptor for use with the tissue sample holder assembly of FIG. 16 in lieu of the cassette tray of FIG. 11.
Figure 52:
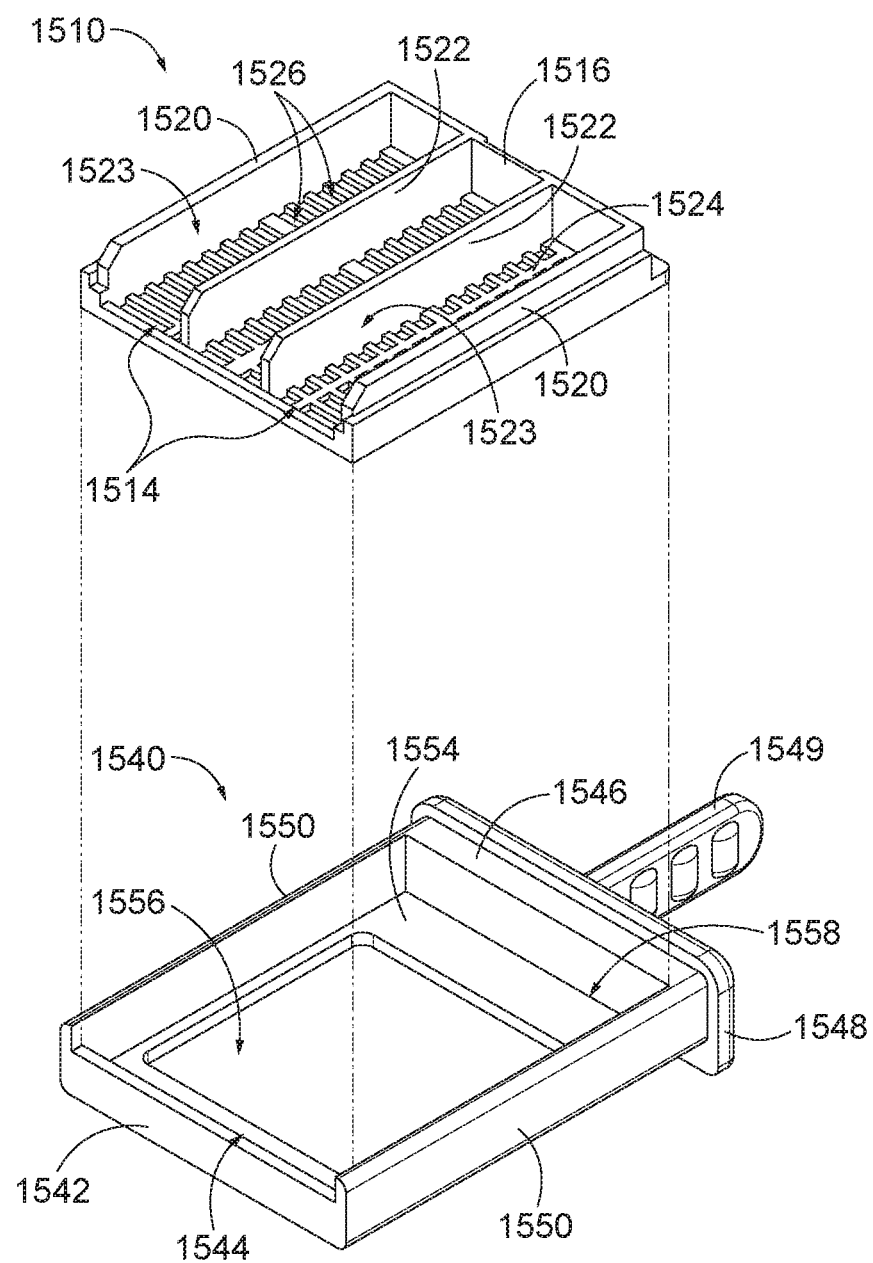
FIG. 52 depicts a perspective exploded view of the cassette adaptor of FIG. 51.

FIGS. 51-52 show an exemplary cassette assembly (1500) that may be readily used with tissue sample holder assembly (600) described above in lieu of components of cassette assembly (500). As will be described in greater detail below, certain components of cassette assembly (1500) are also readily usable with cassette (200) described above. Cassette assembly (1500) of the present example includes a cassette adaptor (1510) and an adaptor tray (1540). As will be described in greater detail below, cassette adaptor (1510) is generally configured to contain one or more tissue samples such that tissue samples may be initially collected within cassette adaptor (1510) using tissue sample holder assembly (600) and then later stored within cassette (200). As best seen in FIG. 52 Cassette adaptor (1510) comprises a proximal wall (1516), a pair of sidewalls (1520) extending from proximal wall (516), and a floor (1524) positioned below walls (1516, 1520). The distal end of cassette adaptor (1510) includes a plurality of openings (1514) evenly spaced laterally across the distal end of cassette adaptor (1510). As will be described in greater detail below, each opening (1514) is generally configured to receive a tissue sample. Although not shown, it should be understood that in some examples proximal wall (1516) includes a plurality of indicia on the upper surface of proximal wall (1516). In such examples, indicia can form a plurality of unique numerical identifiers that is visible under x-ray imaging.

Walls (1516, 1520) are interconnected to form the outer perimeter of cassette adaptor (1510). Internally, cassette adaptor (1510) includes a plurality of inner divider walls (1522) extending longitudinally from proximal wall (1516). Each inner divider wall (1522) is positioned parallel relative to sidewalls (1520) an equal distance apart to define a plurality of discrete sample chambers (1523). Each sample chamber (1523) is generally configured to hold a single tissue sample severed by biopsy device (10). Although the present example includes three discrete sample chambers (1523), it should be understood that in other examples any other suitable number of sample chambers (1523) can be used. In such examples, it should be understood that each sample chamber (1523) can be configured for receiving more than a single tissue sample as with sample chambers (1523) in the present example.

Floor (1524) is positioned below walls (1516, 1520, 1522). In the present example, each wall (1516, 1520, 1522) is integral with each wall. However, in other examples one or more of each wall (1516, 1520, 1522) can be separate from floor (1524) and attached with adhesive or some form of mechanical fastening. Floor (1524) includes a plurality of vents (1526). Vents (1526) are generally configured to promote the flow of fluid through floor (1524), yet maintain tissue samples within each sample chamber (1523). To facilitate this configuration, vents (1526) have a narrow rectangular form. In other examples, vents (1526) can be configured with a variety of alternative shapes such as round, oval-shaped, square, and/or etc. Although vents (1526) in the present example are arranged to uniformly occupy the entire surface of floor (1524), it should be understood that in other examples vents (1526) can be arranged in a variety of other ways. For instance, vents (1526) can be isolated to a specific region or multiple regions of floor (1524). Of course, other alternative arrangements for vents (1526) will be apparent to those of ordinary skill in the art in view of the teachings herein.

Although floor (1524) of the present example is shown as being a generally solid structure with vents (1526) extending therethrough, it should be understood that in other examples floor (1524) may include various alternative configurations. For instance, in some examples floor (1524) may take the form of a mesh or porous membrane. By way of example only, in some examples floor (1524) can be substantially the same as floor (1024) described above with respect to cassette tray (1010). Of course, other configurations for floor (1524) can be used as will be apparent to those of ordinary skill in the art in view of the teachings herein.

Floor (1524) is opposite to an open space above each sample chamber (1523). Thus, the upper portion of cassette adaptor (1510) is generally open. Because of this, tissue samples may be deposited into each sample chamber (1523) through openings (1514) in the distal end of cassette adaptor (1510) or through the open upper portion of cassette adaptor (1510). As will be described in greater detail below, tissue samples are generally contained within each sample chamber (1523) once cassette adaptor (1510) is received within cassette (200).

Adaptor tray (1540) is generally configured to receive cassette adaptor (1510). Adaptor tray (1540) is further generally configured to be received within manifold (640) of tissue sample holder assembly (600). As will be described in greater detail below, in the present configuration adaptor tray (1540) is thus configured to adapt cassette adaptor (1510) for use with tissue sample holder assembly (600). As best seen in FIG. 52, adaptor tray (1540) comprises a distal wall (1542), a proximal wall (1546), and a pair of sidewalls (1550) extending between distal wall (1542) and proximal wall (1546). Distal wall (1542) defines a generally transverse longitudinal opening (1544) or recess. As will be understood, opening (1544) is configured to expose openings (1514) of cassette adaptor (1510) such that tissue samples may be received within each opening (1514) via opening (1544) of distal wall (1542).

Proximal wall (1546) is generally solid and includes an oversized sealer (1548). As will be understood, sealer (1548) is generally configured to block the proximal end of manifold (640) when adaptor tray (1540) is received within tissue sample holder assembly (600). Although not shown, it should be understood that in some examples sealer (1548) may include certain sealing features such as rubber gaskets, or the like. Proximal wall (1546) further includes a pull tab (1549) extending proximally from sealer (1548). As will be understood, pull tab (1549) is generally configured to permit an operator to grip adaptor tray (1540) for removal from tissue sample holder assembly (600).

Walls (1542, 1546, 1550) are all integral with a floor (1554) disposed below each wall (1542, 1546, 1550). Floor (1554) generally defines an oversized opening (1556) therein. Opening (1556) is generally sized to permit unobstructed fluid flow through floor (1554). Yet, opening (1556) is also generally sized such that floor (1554) is large enough to generally support cassette adaptor (1510) so that cassette adaptor (1510) remains on top of floor (1554). As will be understood, this configuration permits adaptor tray (1540) to manipulate cassette adaptor (1510), while still permitting fluid flow through vents (1526) of cassette adaptor (1510).

Walls (1542, 1546, 1550) are also interconnected to thereby define a receiving chamber (1558) positioned above floor (1554). Receiving chamber (1558) is generally configured to receive cassette adaptor (1510). For receipt of cassette adaptor (1510) within receiving chamber (1558), the upper portion of adaptor tray (1540) is generally open such that adaptor tray (1540) is generally configured to receive cassette adaptor (1510) through the upper portion of adaptor tray (1540).

FIGS. 53A-54B show an exemplary use of cassette assembly (1500) in connection with tissue sample holder assembly (600) and cassette (200). It should be understood that although cassette assembly (1500) of the present example is described as being used with tissue sample holder assembly (600), in other contexts cassette assembly (1500) can be readily used with other components described herein. For instance, in some examples cassette assembly (1500) is readily useable with tissue sample holder assembly (1200, 1300) described above.

Figure 53A:
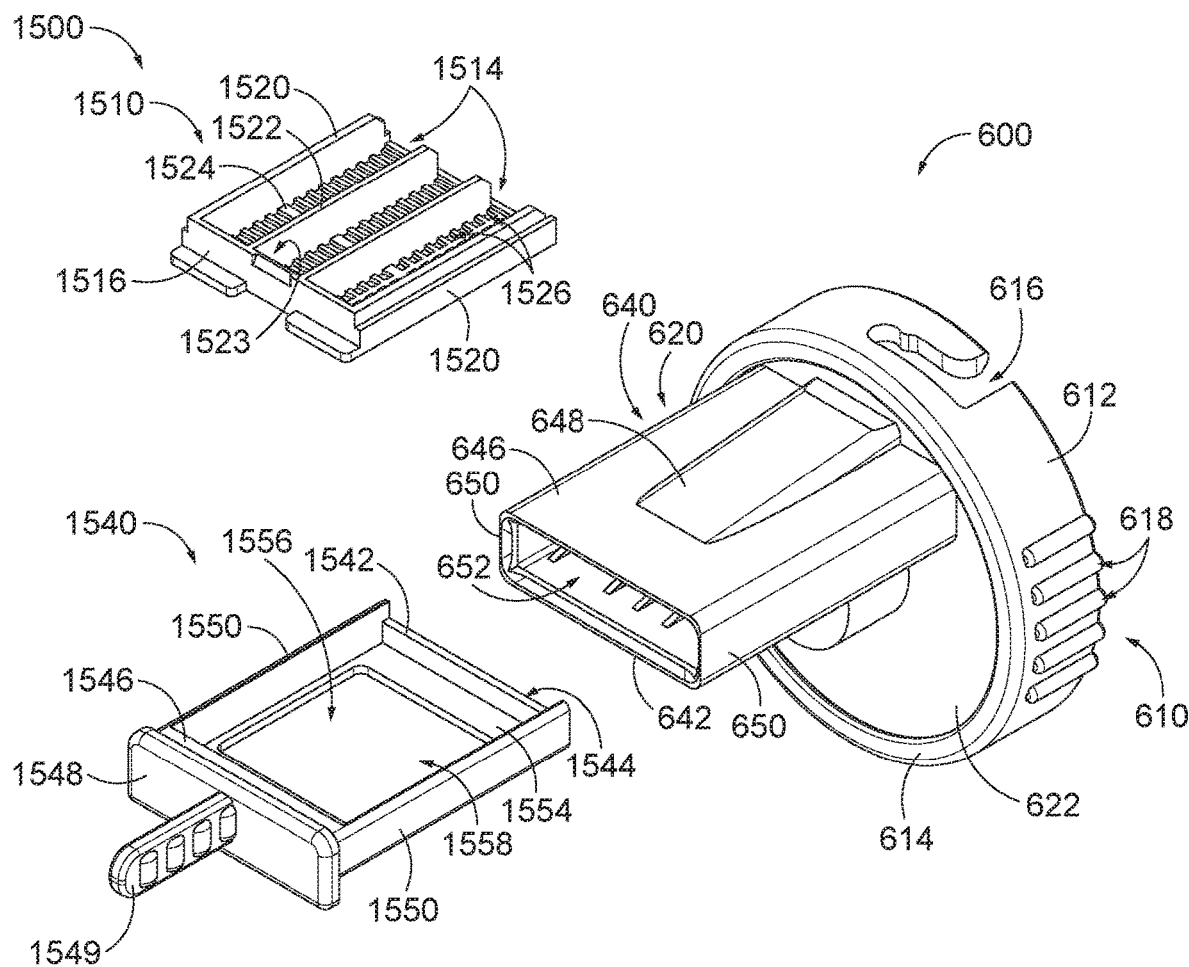
FIG. 53A depicts a perspective view of the tissue sample holder assembly of FIG. 16, with the cassette adaptor of FIG. 51 in a separated state adjacent to the tissue sample holder assembly.
Figure 533:
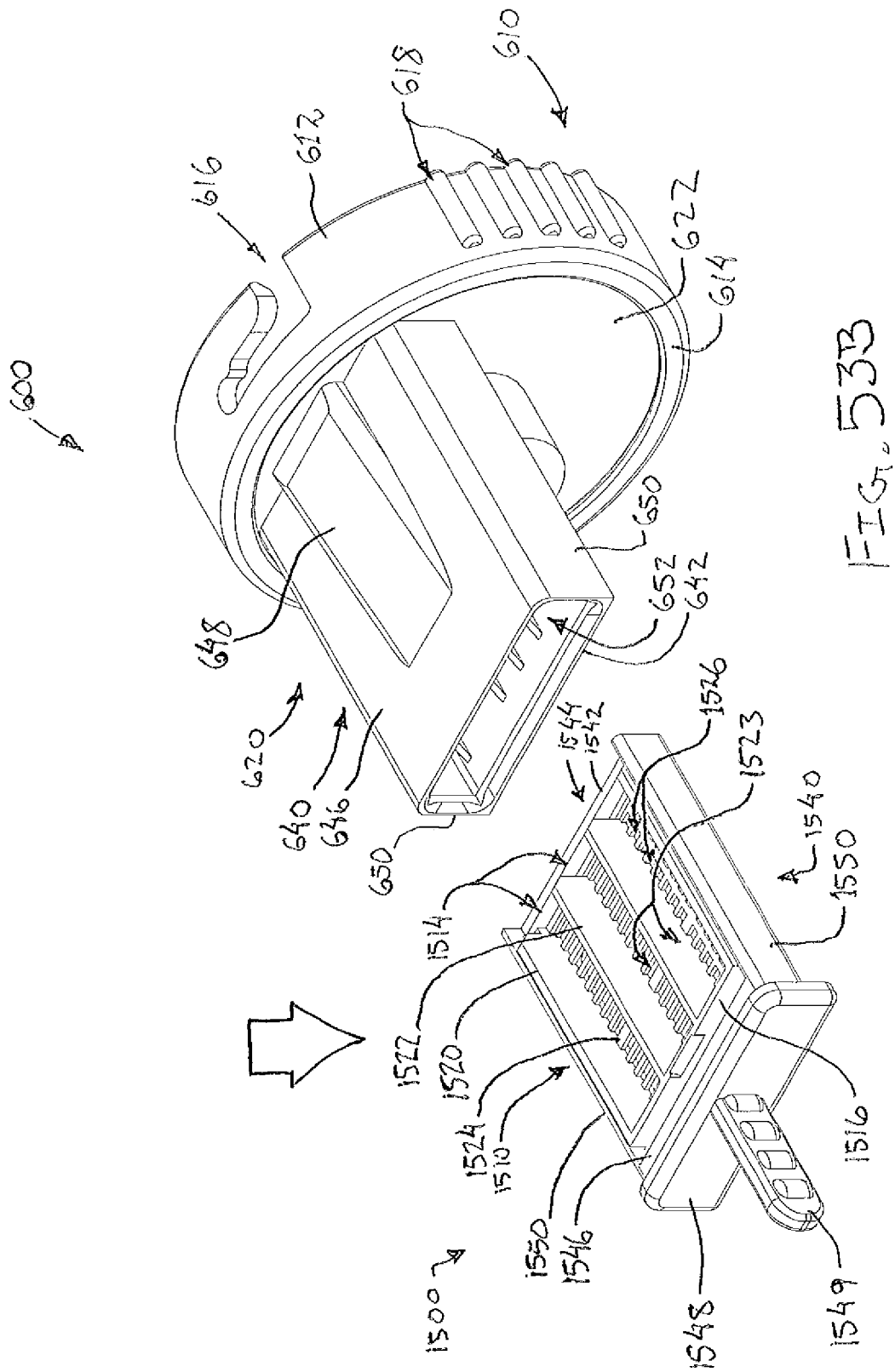

As best seen in FIG. 53A, cassette adaptor (1510) is initially separated from adaptor tray (1540) and adaptor tray (1540) is initially separated from manifold (640) tissue sample holder assembly (600). Thus, an operator may begin a biopsy procedure by inserting cassette adaptor (1510) into adaptor tray (1540) as shown in FIG. 53B.

Once cassette adaptor (1510) is inserted into adaptor tray (1540), the combination of cassette adaptor (1510) and adaptor tray (1540) shown in FIG. 53B can be inserted into manifold (640) of tissue sample holder assembly (600) as shown in FIG. 53C.

Once the combination of cassette adaptor (1510) and adaptor tray (1540) are inserted in to manifold (640) of tissue sample holder assembly (600), tissue sample holder assembly (600) may be used to collect tissue samples within cassette adaptor (1510) as similarly described above. Although not shown, it should be understood that in some examples tissue sample holder assembly (600) can include certain modifications to function with cassette adaptor (1510) and adaptor tray (1540). For instance, as described above, cassette adaptor (1510) includes three tissue sample chambers (1523) instead of four described above in connection with cassette tray (510). To accommodate this difference, rotatable member (620) can include differently configured sample openings (630, 632) and vacuum openings (634). Alternatively, the same configuration may be used with one or more tissue sample chambers (1523) being used to receive multiple tissue samples.

Once an operator has collected a desired number of tissue sample, an operator may conclude the biopsy procedure and subsequently remove the combination cassette adaptor (1510) and adaptor tray (1540) from manifold (640) of tissue sample holder assembly (600) as shown by reversing FIGS. 53C and 53B. Next, cassette adaptor (1510) is removed from adaptor tray (1540) as shown by the reverse of FIGS. 53B and 53A.

Once cassette adaptor (1510) is removed from adaptor tray (1540), cassette adaptor (1510) can be used to subject the collected tissue samples to procedure room x-ray. For instance, cassette adaptor (1510) may be placed directly into a procedure room x-ray machine. In addition, or in the alternative, the collected tissue samples may also be visually inspected while disposed within cassette adaptor (1510).

Figure 54A:
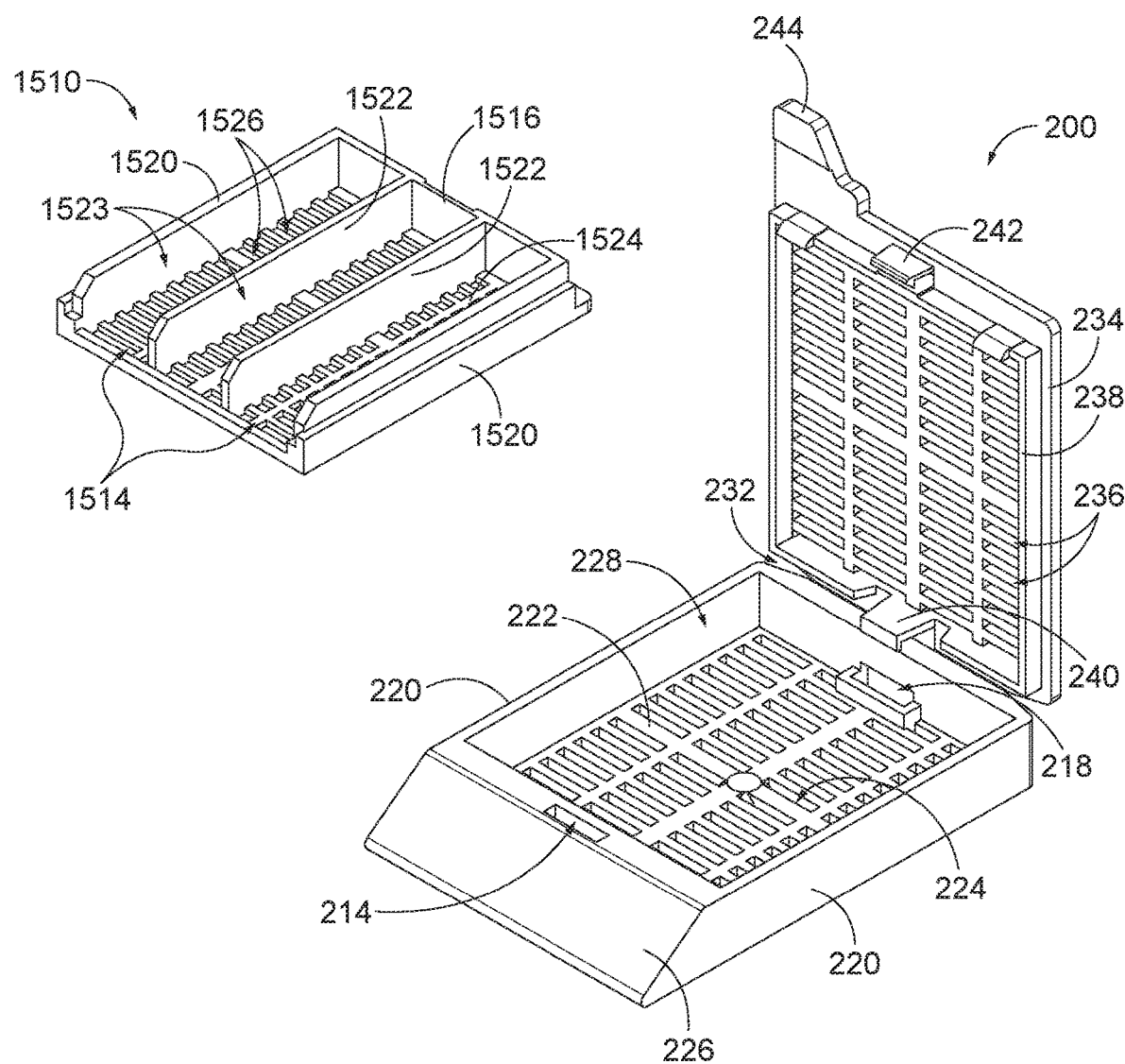
FIG. 54A depicts a perspective view of the cassette of FIG. 6, with the cassette in an open configuration for receipt of an adaptor tray of the cassette adaptor of FIG. 51.

Once the preliminary sample analysis procedures are optionally performed, an operator may desire to transfer the collected tissue samples to a pathology laboratory. At this stage, cassette adaptor (1510) may be loaded into cassette (200) as shown in FIGS. 54A-54B. The combination of cassette adaptor (1510) and cassette (200) is then transferred to a pathology laboratory, where the entire assembly can be subjected to one or more steps of the workflow (300) shown in FIG. 7.

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A cassette assembly for use with a biopsy device, the cassette assembly comprising: a cassette tray including a plurality of walls defining one or more sample chambers, and a labeling portion configured to present patient data to an operator; and a cover configured to receive the cassette tray and defining a plurality of vents configured to communicate fluid into the cassette tray when the cassette tray is disposed within the cover, wherein the labeling portion of the cassette tray is exposed relative to the cover when the cassette tray is disposed within the cover.

EXAMPLE 2

The cassette assembly of Example 1, wherein the further includes a floor including a plurality of vents, wherein the plurality of vents are configured to maintain one or more tissue samples within the one or more sample chambers defined by the plurality of walls.

EXAMPLE 3

The cassette assembly of Example 2, wherein the cover further defines a plurality of openings positioned opposite of the plurality of vents of the cover, wherein the plurality of openings are configured to expose the plurality of vents of the cassette tray relative to the exterior of the cover.

EXAMPLE 4

The cassette assembly of Example 3, wherein the cover further includes a support structure which defines at least a portion of the plurality of openings, wherein the support structure is configured to hold at least a portion of the cassette tray within the cover.

EXAMPLE 5

The cassette assembly of Example 4, wherein the floor of the cassette tray further includes one or more detents configured to engage the support structure of the cover to hold the cassette tray in a plurality of predetermined positions relative to the cover.

EXAMPLE 6

The cassette assembly of any one or more of Examples 1 through 5, wherein the plurality of walls of the cassette tray includes a distal wall defining one or more sample openings in communication with a respective sample chamber of the one or more sample chambers.

EXAMPLE 7

The cassette assembly of Example 6, wherein the sample openings of the cassette tray are configured to interface with the biopsy device to receive one or more tissue samples within each sample chamber of the one or more sample chambers.

EXAMPLE 8

The cassette assembly of any one or more of Examples 1 through 7, wherein the cassette tray further includes one or more indicia, wherein each indicia of the one or more indicia corresponds to a respective sample chamber.

EXAMPLE 9

The cassette assembly of Example 8, wherein the plurality of walls of the cassette tray includes a proximal wall, wherein the one or more indicia are disposed on the proximal wall.

EXAMPLE 10

The cassette assembly of Example 8, wherein the one or more indicia are configured to be visible under x-ray imaging.

EXAMPLE 11

A sample collection and analysis system for use with a biopsy device, wherein the system comprises: a tissue sample holder assembly including a rotatable member defining a manifold; a cassette tray defining a plurality of tissue sample chambers, wherein the cassette tray is configured for receipt within the manifold of the tissue sample holder assembly; a cover, wherein the cover is configured to receive the cassette tray; and a transport jar filled with a fixative, wherein the transport jar is configured to receive the cover after receipt of the cassette tray within the cover.

EXAMPLE 12

The system of Example 11, further including a sterile cover selectively securable to a surface of the cassette tray to seal at least a portion of the cassette tray relative to the exterior of the cassette tray.

EXAMPLE 13

The system of Example 12, wherein the sterile cover is configured to removably adhere to at least a portion of the cassette tray.

EXAMPLE 14

The system of any one or more of Examples 12 through 13, wherein the sterile cover is a flexible film.

EXAMPLE 15

The system of any one or more of Examples 12 through 13, wherein the sterile cover is a hard cover.

EXAMPLE 16

The system of any one or more of Examples 11 through 13, wherein the cassette tray defines a plurality of sample openings corresponding to each tissue sample chamber.

EXAMPLE 17

The system of Example 16, wherein the rotatable member further defines a plurality of sample openings, with each sample opening corresponding to a sample opening of the cassette tray, wherein the rotatable member is rotatable relative to the biopsy device to successively index each sample opening of the rotatable member with a cutter of the biopsy device.

EXAMPLE 18

The system of Example 16, wherein at least one sample opening defined by the rotatable member is laterally offset relative to another sample opening such that the plurality of sample openings of the rotatable member are arrange along an arched path.

EXAMPLE 19

The system of any one or more of Examples 11 through 17, wherein the cassette tray includes a coupling portion defining a coupler, wherein the cover includes a receiver configured to engage the coupler of the coupling portion to selectively secure the cassette tray to the cover.

EXAMPLE 20

The system of Example 19, wherein the manifold of the tissue sample holder assembly includes a receiver, wherein the receiver of the manifold is configured to engage the coupler of the coupling portion of the cassette tray to selectively secure the cassette tray to the manifold.

EXAMPLE 21

The system of any one or more of Examples 11 through 20, wherein the manifold defines a raised connector, wherein the raised connector is configured to deflect one or more tissue samples into the cassette tray when the cassette tray is disposed within the manifold.

EXAMPLE 22

A method for collecting and handling tissue samples, the method comprising: inserting a cassette tray into a manifold of a rotatable member associated with a biopsy device; collecting a first tissue sample within a first sample chamber defined by the cassette tray; collecting a second tissue sample within a second sample chamber defined by the cassette tray; collecting one or more subsequent tissue samples until a desired number of tissue samples have been collected; removing the cassette tray from the manifold of the rotatable member; inserting the cassette tray into a cover; inserting the cover into ajar filled with a fixation agent; transporting the jar to a pathology laboratory.

EXAMPLE 23

The method of Example 22, further comprising the step of performing one or more pathological tissue processing steps while the first and second tissue samples are disposed within the cassette tray.

EXAMPLE 24

The method of Example 23, wherein the one or more pathological tissue processing steps includes slicing sections using a microtome.

EXAMPLE 25

The method of any one or more of Examples 22 through 24, further comprising the step of performing a procedure room x-ray on the cassette tray while at least the first tissue sample is disposed within the cassette tray.

EXAMPLE 26

The method of any one or more of Examples 22 through 26, further comprising the step of applying a label to a label portion associated with the cassette tray.

EXAMPLE 27

The method of Example 26, wherein the label includes information related to a patient.

EXAMPLE 28

The method of Example 26, wherein the step of applying a label includes printing information onto a surface of the label portion.

EXAMPLE 29

The method of Example 25.26, wherein the label portion projects from a portion of the cassette tray.

EXAMPLE 30

The method of Example 26, wherein the step of applying a label includes inputting data into an RFID tag disposed within the label portion.

EXAMPLE 31

The method of any one or more of Examples 26 through 30, further comprising the step of confirming chain of custody of at least the first tissue sample at one or more stages of a biopsy and pathology procedure workflow by processing information associated with the label portion.

EXAMPLE 32

The method of Example 31, wherein the step of confirming chain of custody of at least the first tissue sample includes reading information printed on the label portion.

EXAMPLE 33

The method of Example 31, wherein the step of confirming chain of custody of at least the first tissue sample includes scanning information associated with the labeling portion.

EXAMPLE 34

The method of any one or more of Examples 26 through 33, further comprising the step of applying a sterile cover to the cassette tray prior to the step of applying a label.

EXAMPLE 35

The method of any one or more of Examples 26 through 34, wherein the step of applying a label is performed prior to a biopsy procedure.

EXAMPLE 36

The method of any one or more of Examples 26 through 33, wherein the step of applying a label is performed after a biopsy procedure.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A sample collection and processing apparatus comprising:
   a tissue processing cassette, the tissue processing cassette having at least one distal opening through which tissue samples are received and having a floor spanning the width of the cassette, the cassette having a plurality of openings aligned along a common plane; and
   a biopsy device for cutting tissue samples and having a cassette holder adapted to receive the tissue processing cassette while the plurality of openings of the cassette are aligned along the common plane, the cassette holder having a fluid path adapted to be coupled to a vacuum source and in fluid communication with the interior of the tissue processing cassette through the openings of the floor such that the vacuum from the vacuum source facilitates the transfer of the cut tissue samples into the received tissue processing cassette,
   the cassette holder defining a plurality of sample openings, the tissue processing cassette defining a plurality of distal openings with each distal opening corresponding to a sample opening of the cassette holder, the cassette holder being rotatable relative to a cutter of the biopsy device to successively index each sample opening with the cutter, and
   the cassette holder further including a plurality of vacuum openings, each vacuum opening being proximate to and corresponding to a respective sample opening of the plurality of sample openings.

2. The apparatus of claim 1, the tissue processing cassette including a plurality of distal openings.

3. The apparatus of claim 1, the tissue processing cassette including a plurality of distal openings, the cassette holder being movable relative to a cutter of the biopsy device to index each distal opening with the cutter.

4. The apparatus of claim 1, each sample opening of the cassette holder being laterally offset relative to another sample opening such that the plurality of sample openings are together arranged along an arched path.

5. The apparatus of claim 1, the cassette holder further including a plurality of vacuum channels configured to direct vacuum from each vacuum opening and through the floor of the tissue processing cassette.

6. The apparatus of claim 1, the cassette holder defining a raised connector, the raised connector being configured to deflect one or more tissue samples into the tissue processing cassette when the tissue processing cassette is disposed in the cassette holder.

7. The apparatus of claim 1, the cassette holder being configured to receive a plurality of tissue processing cassettes.

8. The apparatus of claim 1, the tissue processing cassette including an angled surface configured to receive identifying information thereon.

9. The apparatus of claim 1, the cassette holder further including an access port configured to receive a plug independently of receipt of the tissue processing cassette.

10. The apparatus of claim 1, the tissue processing cassette-including a plurality of interior walls, the interior walls defining a plurality of tissue sample chambers with each tissue sample chamber configured to receive a tissue sample.

11. The apparatus of claim 1, further comprising a coupler configured to couple the cassette holder to a proximal end of the biopsy device.

12. The apparatus of claim 1, the cassette holder including an open proximal end configured to receive the tissue processing cassette therethrough.

13. A sample collection and processing apparatus comprising:
   (a) a tissue processing cassette, the tissue processing cassette having a plurality of distal openings through which tissue samples are received and having a floor with a plurality of openings; and
   (b) a biopsy device for cutting tissue samples and having a cassette holder adapted to receive the tissue processing cassette, the cassette holder having a fluid path adapted to be coupled to a vacuum source and in fluid communication with the interior of the tissue processing cassette through the openings of the floor such that the vacuum from the vacuum source facilitates the transfer of the cut tissue samples into the received tissue processing cassette, the cassette holder having a plurality of sample openings, the sample openings of the cassette holder being arranged along an arch and being configured to communicate with the distal openings of the tissue processing cassette while the distal openings are arranged along a single axis, and
   the cassette holder further having a plurality of vacuum openings, each vacuum opening of the plurality of vacuum openings being arranged along a common axis.

14. The apparatus of claim 13, the cassette holder further having a raised connector including an angled portion configured to deflect tissue samples from one or more sample openings of the cassette holder into one or more distal openings of the tissue processing cassette.

15. The apparatus of claim 13, each vacuum opening of the plurality of vacuum openings defining a different shape relative to each other vacuum opening.

16. A sample collection and processing apparatus comprising:
   (a) a rigid tissue processing cassette, the tissue processing cassette having a plurality of distal openings through which tissue samples are received and having a flat floor with a plurality of openings; and
   (b) a biopsy device for cutting tissue samples and having a cassette holder adapted to receive the tissue processing cassette, the cassette holder having a fluid path adapted to be coupled to a vacuum source and in fluid communication with the interior of the tissue processing cassette through the openings of the floor such that the vacuum from the vacuum source facilitates the transfer of the cut tissue samples into the received tissue processing cassette, and the cassette holder including a sample deflector extending proximally along a portion of the cassette holder, the sample deflector being oriented at an angle relative to the floor of the tissue processing cassette such that the sample deflector is configured to deflect one or more of the tissue samples from the cassette holder and into the tissue processing cassette.

* * * * *